(12) United States Patent
Feldberg et al.

(10) Patent No.: US 12,171,753 B2
(45) Date of Patent: Dec. 24, 2024

(54) CRYSTALLINE FORMS OF ALDH2 MODULATORS

(71) Applicant: SOPHROSYNE PHARMACEUTICALS LIMITED, George Town (KY)

(72) Inventors: Lewis Feldberg, Montclair, NJ (US); Akram Sabouni, Cary, NC (US); Thomas R. Bailey, Phoenixville, PA (US); Vincent Wing-Fai Tai, San Diego, CA (US); Tom Leyssens, Jette (BE)

(73) Assignee: Sophrosyne Pharmaceuticals Limited, George Town (KY)

( * ) Notice: Subject to any disclaimer, the term of this patent is extended or adjusted under 35 U.S.C. 154(b) by 18 days.

(21) Appl. No.: 17/837,619

(22) Filed: Jun. 10, 2022

(65) Prior Publication Data

US 2023/0096245 A1     Mar. 30, 2023

Related U.S. Application Data

(60) Provisional application No. 63/202,423, filed on Jun. 10, 2021.

(51) Int. Cl.
*A61K 31/44*      (2006.01)
*A61K 45/06*      (2006.01)
*A61P 25/32*      (2006.01)
*C07D 211/60*     (2006.01)

(52) U.S. Cl.
CPC .............. *A61K 31/44* (2013.01); *A61K 45/06* (2013.01); *A61P 25/32* (2018.01); *C07D 211/60* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,896,169 A | 7/1975 | Tiles et al. | |
| 3,897,492 A | 7/1975 | Tiles et al. | |
| 3,975,180 A * | 8/1976 | Gozzo | A01N 47/28 |
| | | | 504/303 |
| 4,299,765 A | 11/1981 | Tilles | |
| 4,383,025 A | 5/1983 | Green et al. | |
| 7,250,401 B2 | 7/2007 | Schloss | |
| 11,746,089 B2 | 9/2023 | Feldberg et al. | |
| 2022/0169610 A1 | 6/2022 | Feldberg et al. | |

FOREIGN PATENT DOCUMENTS

| | | |
|---|---|---|
| DE | 2350475 A1 | 4/1974 |
| DE | 2350478 A1 | 4/1974 |
| EP | 0062876 A1 | 10/1982 |
| WO | 2022115742 A1 | 6/2022 |

OTHER PUBLICATIONS

Zhang et al. "ALDH2 in Alcoholic Heart Diseases: Molecular Mechanism and Clinical Implications", 2011, Pharmacology & Therapeutics, 132, pp. 86-95 (Year: 2011).*
Isenberg-Grzeda et al. "Wernicke-Korsakoff-Syndrome: Under-Recognized and Under-Treated", 2012, Psychosomatics, 53, pp. 507-516 (Year: 2012).*
Cook et al. "Associations of ALDH2 and ADH1B genotypes with response to alcohol in Asian Americans", 2005, Journal of Studies on Alcohol, 66, Abstract Only (Year: 2005).*
Karimi-Jafari et al. "Creating Cocrystals: A Review of Pharmaceutical Cocrystal Preparation Routes and Applications", 2018, Crystal Growth & Design, 18, pp. 6370-6387 (Year: 2018).*
Mizuno et al. "Solvent-assisted thiocarboxylation of amines and alcohols with carbon monoxide and sulfur under mild conditions", 2005, Tetrahedron, 61, pp. 9157-9163 (Year: 2005).*
Mays et al. "Inhibition of Recombinant Human Mitochondrial Aldehyde Dehydrogenase by Two Intermediate Metabolites of Disulfiram", 1998, Biochemical Pharmacology, 55, pp. 1099-1103 (Year: 1998).*
Higuchi et al. "Influence of Genetic Variations of Ethanol-Metabolizing Enzymes on Phenotypes of Alcohol-Related Disorders", 2004, Annals New York Academy of Sciences, 1025, pp. 472-480 (Year: 2004).*
Caito et al. "Dopaminergic neurotoxicity of S-ethyl N, N-dipropylthiocarbamate (EPTC), molinate, and S-methyl-N, N-diethylthiocarbamate (MeDETC) in Caenorhabditis elegans", 2013, Journal of Neurochemistry, 127, 837-851 (Year: 2013).*
Mays, et al., "Inhibition of Recombinant Human Mitochondrial Aldehyde Dehydrogenase by Two Intermediate Metabolites of Disulfiram," Biochemical Pharmacology, 1998, vol. 55, Elsevier Science Inc., pp. 1099-1103.
Fukte, et al., "Coformer Selection: An Important Tool in Cocrystal Formation," International Journal of Pharmacy and Pharmaceutical Sciences, vol. 6, Issue 7, 2014, pp. 9-14.
Yan et al., "Improving the Solubility of Agomelatine via Cocrystals", Crystal Growth & Decision, 2012, pp. 2226-2233.
International Search Report and Written Opinion Issued in PCT/US2021/061098 dated Apr. 13, 2022.
Notice of Allowance for U.S. Appl. No. 17/860,913 dated Sep. 15, 2022.
PUBCHEM 319089572 deposited Nov. 29, 2016, pp. 1-5.
PUBCHEM 431811781 deposited on Aug. 14, 2020, pp. 1-6.
Fukte et al., "Coformer Selection: An Important Tool in Cocrystal Formation", International Journal of Pharmacy and Pharmaceutical Sciences, 2014, vol. 6, Issue 7, pp. 9-14.
Mays et al., "Inhibition of Recombinant Human Mitochondrial Aldehyde Dehydrogenase by Two Intermediate Metabolites of Disulfiram", Biochemical Pharmacology, 1998, vol. 55, pp. 1099-1103.
International Search Report and Written Opinion Issued in PCT/US2022/33012 dated Nov. 13, 2022.

(Continued)

*Primary Examiner* — Jeffrey H Murray
*Assistant Examiner* — Madeline E Braun
(74) *Attorney, Agent, or Firm* — Goodwin Procter LLP

(57) ABSTRACT

Provided herein are novel crystalline forms of a compound that acts as an ALDH2 effector, processes for preparing the crystalline forms of the compound with or without coformer, and uses thereof.

21 Claims, 37 Drawing Sheets

(56) References Cited

OTHER PUBLICATIONS

Non-Final Office Action dated Jan. 20, 2023 in U.S. Appl. No. 17/538,250.
Braverman et al., "The rearrangement of allylic trichloromethanesulfenates," 6 Chem. Commn'cs. (London) 270-1 (1967) (Year: 1967).
International Preliminary Report on Patentabiltiy dated Nov. 21, 2023, which includes Written Opinion Issued in PCT/US2022/33012 dated Nov. 14, 2022. 8 pages.

\* cited by examiner

CRYSTALLINE FORMS OF ALDH2 MODULATORS

CROSS-REFERENCE TO RELATED APPLICATIONS

This application claims priority to U.S. Provisional Application No. 63/202,423, filed Jun. 10, 2021, which is hereby incorporated by reference in its entirety.

FIELD

The present disclosure describes novel crystalline forms of compounds with or without coformer that act as ALDH2 effectors, processes for preparing the crystalline forms of the compounds with or without the coformer, and uses thereof.

BACKGROUND

U.S. Patent Provisional Application No. 63/119,211 discloses compounds that act as modulators of Aldehyde dehydrogenase (ALDH2). For example, the compounds modulating the activity of ALDH2, such as ALDH2 inhibition, may be beneficial in the treatment of a variety of an alcohol-related disorder, such as alcohol use disorder, alcohol-induced disorder, alcohol abuse, alcohol dependence, alcohol intoxication, alcohol withdrawal, and the like. One particular compound is "S-methyl-N,N-diethylthiocarbamate sulfoxide." which has a formula of Formula I

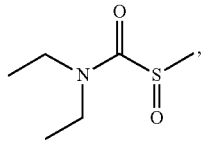

and its enantiomers are compounds having the respective formulae of

Formula I-a

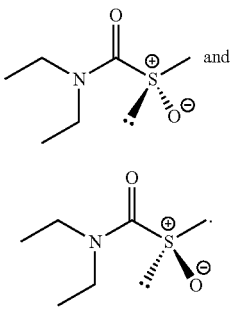

Formula I-b

Another example is a compound having a formula of

Formula IV-a

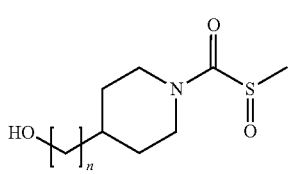

and its enantiomers are compounds having the respective formulae of

Formula IV-b

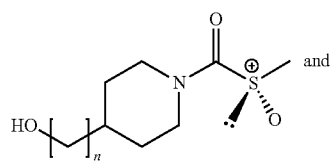

Formula IV-c

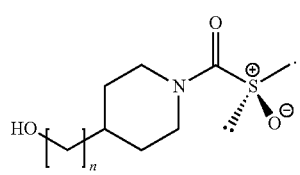

Another particular example is "(methylsulfinyl)(morpholino)methanone", which has a formula of Formula III

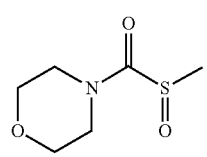

and its enantiomers are compounds having the respective formulae of

Formula III-a

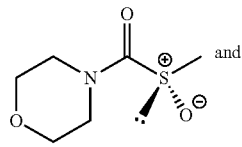

Formula III-b

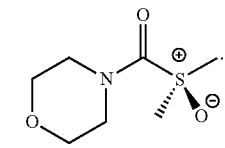

The compound of any one of the Formulae, as described or provided for herein, such as Formula I, Formula III, and Formula IV, the ability of the compound to affect ALDH activity, or the absence of such activity, methods for preparation of the compound of any one of the Formulae, as described or provided for herein, and other related compounds are disclosed in U.S. Patent Provisional Application No. 63/119,211, the contents of which are incorporated herein by reference in their entirety.

There remains a need in the art for improved forms of the compound of any one of the Formulae, as described or provided for herein, such as Formula I, Formula III, and Formula IV with improved properties. There also remains a need in the art for improved processes for preparing the compound of any one of the Formulae, as described or provided for herein, such as the compound of Formula I, Formula III, and Formula IV. The present embodiments described herein fulfill these needs and others.

SUMMARY

The present disclosure provides novel crystalline forms of a compound of any one of the Formulae, as described or provided for herein, such as Formula I, Formula III, and Formula IV with or without coformer, processes for preparing the crystalline forms of the compound, and optionally isolating such crystalline forms.

Surprisingly, the compound of any one of the Formulae, as described or provided for herein, such as Formula I, Formula III, and Formula IV can be co-crystallized with a coformer and is superior in properties. In some embodiments, co-crystalline forms of the compound of any one of the Formulae, as described or provided for herein, such as Formula I, Formula III, and Formula IV with coformer, are distinguished from the prior art by improved stability, processability and can also be used in pharmaceutical formulations. In some embodiments, co-crystalline forms of the compound of Formula I, Formula I-a, and Formula I-b with coformer are distinguished from the prior art by improved stability, processability and can also be used in pharmaceutical formulations. In some embodiments, co-crystalline forms of the compound of Formula IV-I, Formula IV-Ia, and Formula IV-Ib with coformer are distinguished from the prior art by improved stability, processability and can also be used in pharmaceutical formulations.

In some embodiments, co-crystalline forms of the compound of any one of the Formulae, as described or provided for herein, such as Formula I, Formula I-a, or Formula I-b with a coformer are provided. In some embodiments, co-crystalline forms of the compound of Formula I, Formula I-a, or Formula I-b with a coformer are provided. In some embodiments, co-crystalline forms of the compound of Formula I with a coformer are provided. In some embodiments, co-crystalline forms of the compound of Formula I-a with a coformer are provided. In some embodiments, co-crystalline forms of the compound of Formula I-b with a coformer are provided. In some embodiments, a co-crystalline Form I, Form II, Form III, Form IV, Form V, Form VI, or Form VII of the compound of Formula I-b with a coformer are provided. In some embodiments, the coformer is a coformer provided and described herein. In some embodiments, the coformer is urea, 3,5-dihydroxybenzoic acid, trimesic acid, ellagic acid, $MgCl_2$, or $CaCl_2$, or any combination thereof. In some embodiments, the coformer is urea. In some embodiments, the coformer is 3,5-dihydroxybenzoic acid. In some embodiments, the coformer is trimesic acid. In some embodiments, the coformer is ellagic acid.

In some embodiments, co-crystalline forms of the compound of any one of the Formulae, as described or provided for herein, such as Formula IV-I, Formula IV-I-a, or Formula IV-I-b with a coformer are provided. In some embodiments, co-crystalline forms of the compound of Formula IV-I, Formula IV-I-a, or Formula IV-I-b with a coformer are provided. In some embodiments, co-crystalline forms of the compound of Formula IV-I with a coformer are provided. In some embodiments, co-crystalline forms of the compound of Formula IV-I-a with a coformer are provided. In some embodiments, co-crystalline forms of the compound of Formula IV-I-b with a coformer are provided. In some embodiments, the coformer is a coformer provided and described herein. In some embodiments, the coformer is trifluorotriiodobenzene, 4-aminobenzoic acid, L-aspartic acid, paracetamol, ellagic acid, 2-aminobenzoic acid, or urea, or any combination thereof. In some embodiments, the coformer is trifluorotriiodobenzene. In some embodiments, the coformer is 4-aminobenzoic acid. In some embodiments, the coformer is L-aspartic acid. In some embodiments, the coformer is paracetamol. In some embodiments, the coformer is ellagic acid, 2-aminobenzoic acid. In some embodiments, the coformer is or urea.

In some embodiments, the co-crystalline Form I of the compound of Formula I, Formula I-a, or Formula I-b (hereinafter the "co-crystalline Form I") is provided. In some embodiments, the co-crystalline Form I is characterized by an X-ray powder diffraction pattern comprising one or more peaks at about 9.0±0.5 degrees 2θ, at about 11.7±0.5 degrees 2θ, at about 14.9±0.5 degrees 2θ, at about 17.0±0.5 degrees 2θ, at about 17.2±0.5 degrees 2θ, at about 17.8±0.5 degrees 2θ, at about 18.0±0.5 degrees 2θ, at about 18.6±0.5 degrees 2θ, at about 21.1±0.5 degrees 2θ, at about 21.5±0.5 degrees 2θ, at about 21.7±0.5 degrees 2θ, at about 23.4±0.5 degrees 2θ, at about 24.8±0.5 degrees 2θ, at about 25.1±0.5 degrees 2θ, at about 25.3±0.5 degrees 2θ, at about 25.9±0.5 degrees 2θ, at about 26.2±0.5 degrees 2θ, at about 27.7±0.5 degrees 2θ, at about 28.2±0.5 degrees 2θ, at about 29.3±0.5 degrees 2θ, at about 29.8±0.5 degrees 2θ, at about 31.7±0.5 degrees 2θ, at about 32.1±0.5 degrees 2θ, and at about 33.3±0.5 degrees 2θ. In some embodiments, the co-crystalline Form I characterized by an X-ray powder diffraction pattern comprising one or more d-spacing values at about 9.8±0.5 degrees angstroms, at about 7.6±0.5 degrees angstroms, at about 5.9±0.5 degrees angstroms, at about 5.2±0.5 degrees angstroms, at about 5.2±0.5 degrees angstroms, at about 5.0±0.5 degrees angstroms, at about 4.9±0.5 degrees angstroms, at about 4.8±0.5 degrees angstroms, at about 4.2±0.5 degrees angstroms, at about 4.1±0.5 degrees angstroms, at about 4.1±0.5 degrees angstroms, at about 3.8±0.5 degrees angstroms, at about 3.6±0.5 degrees angstroms, at about 3.6±0.5 degrees angstroms, at about 3.5±0.5 degrees angstroms, at about 3.4±0.5 degrees angstroms, at about 3.4±0.5 degrees angstroms, at about 3.2±0.5 degrees angstroms, at about 3.2±0.5 degrees angstroms, at about 3.1±0.5 degrees angstroms, at about 3.0±0.5 degrees angstroms, at about 2.8±0.5 degrees angstroms, and at about 2.7±0.5 degrees angstroms.

In some embodiments, the co-crystalline Form II of the compound of Formula I, Formula I-a, or Formula I-b (hereinafter the "co-crystalline Form II") is provided. In some embodiments, the co-crystalline Form II is characterized by an X-ray powder diffraction pattern comprising one or more peaks at about 5.3±0.5 degrees 2θ, at about 7.6±0.5 degrees 2θ, at about 9.1±0.5 degrees 2θ, at about 10.7±0.5 degrees 2θ, at about 12.0±0.5 degrees 2θ, at about 14.2±0.5 degrees 2θ, at about 14.5±0.5 degrees 2θ, at about 15.2±0.5 degrees 2θ, at about 15.7±0.5 degrees 2θ, at about 16.8±0.5 degrees 2θ, at about 17.1±0.5 degrees 2θ, at about 17.2±0.5 degrees 2θ, at about 17.6±0.5 degrees 2θ, at about 17.8±0.5 degrees 2θ, at about 18.3±0.5 degrees 2θ, at about 18.4±0.5 degrees 2θ, at about 18.7±0.5 degrees 2θ, at about 19.5±0.5 degrees 2θ, at about 20.0±0.5 degrees 2θ, at about 21.0±0.5 degrees 2θ, at about 22.1±0.5 degrees 2θ, at about 22.3±0.5 degrees 2θ, at about 23.0±0.5 degrees 2θ, at about 23.3±0.5 degrees 2θ, at about 24.0±0.5 degrees 2θ, at about 24.4±0.5 degrees 2θ, at about 25.4±0.5 degrees 2θ, at about 26.0±0.5 degrees 2θ, at about 26.6±0.5 degrees 2θ, at about 27.1±0.5 degrees 2θ, at about 27.3±0.5 degrees 2θ, and at about 27.6±0.5 degrees 2θ. In some embodiments, the co-crystalline Form II characterized by an X-ray powder diffraction pattern comprising one or more d-spacing values at about 16.6±0.5 degrees angstroms, at about 11.6±0.5 degrees angstroms, at about 9.7±0.5 degrees angstroms, at about 8.3±0.5 degrees angstroms, at about 7.4±0.5 degrees angstroms, at about 6.2±0.5 degrees angstroms, at about 6.1±0.5 degrees angstroms, at about 5.8±0.5 degrees angstroms, at about 5.6±0.5 degrees angstroms, at about 5.3±0.5 degrees angstroms, at about 5.2±0.5 degrees angstroms, at about 5.1±0.5 degrees angstroms, at about 5.0±0.5 degrees angstroms, at about 5.0±0.5 degrees angstroms, at about 4.8±0.5 degrees angstroms, at about 4.8±0.5 degrees angstroms, at about 4.7±0.5 degrees angstroms, at about 4.6±0.5 degrees angstroms, at about 4.4±0.5 degrees angstroms, at about 4.2±0.5 degrees angstroms, at about 4.0±0.5 degrees angstroms, at about 4.0±0.5 degrees angstroms, at about 3.9±0.5 degrees angstroms, at about 3.8±0.5 degrees angstroms, at about 3.7±0.5 degrees angstroms, at about 3.5±0.5 degrees angstroms, at about 3.4±0.5 degrees angstroms, at about 3.4±0.5 degrees angstroms, at about 3.3±0.5 degrees angstroms, at about 3.3±0.5 degrees angstroms, and at about 3.2 degrees angstroms.

In some embodiments, the co-crystalline Form III of the compound of Formula I, Formula I-a, or Formula I-b (hereinafter the "co-crystalline Form III") is provided. In some embodiments, the co-crystalline Form III is characterized by an X-ray powder diffraction pattern comprising one or more peaks at about 13.0±0.5 degrees 2θ, at about 13.7±0.5 degrees 2θ, at about 14.3±0.5 degrees 2θ, at about 26.3±0.5 degrees 2θ, at about 27.2±0.5 degrees 2θ, and at about 31.6±0.5 degrees 2θ. In some embodiments, the co-crystalline Form III characterized by an X-ray powder diffraction pattern comprising one or more d-spacing values at about 6.8±0.5 degrees angstroms, at about 6.5±0.5 degrees angstroms, at about 6.2±0.5 degrees angstroms, at about 3.4±0.5 degrees angstroms, at about 3.3±0.5 degrees angstroms, and at about 2.8 degrees angstroms.

In some embodiments, the co-crystalline Form IV of the compound of Formula I, Formula I-a, or Formula I-b (hereinafter the "co-crystalline Form IV") is provided. In some embodiments, the co-crystalline Form IV is characterized by an X-ray powder diffraction pattern comprising one or more peaks at about 7.6±0.5 degrees 2θ, at about 13.0±0.5 degrees 2θ, at about 13.3±0.5 degrees 2θ, at about 16.7±0.5 degrees 2θ, at about 17.2±0.5 degrees 2θ, at about 18.1±0.5 degrees 2θ, at about 19.7±0.5 degrees 2θ, at about 20.6±0.5 degrees 2θ, at about 21.4±0.5 degrees 2θ, at about 22.5±0.5 degrees 2θ, at about 26.5±0.5 degrees 2θ, and at about 31.3±0.5 degrees 2θ. In some embodiments, the co-crystalline Form IV characterized by an X-ray powder diffraction pattern comprising one or more d-spacing values at about 11.6±0.5 degrees angstroms, at about 6.8±0.5 degrees angstroms, at about 6.6±0.5 degrees angstroms, at about 5.3±0.5 degrees angstroms, at about 5.1±0.5 degrees angstroms, at about 4.9±0.5 degrees angstroms, at about 4.5±0.5 degrees angstroms, at about 4.3±0.5 degrees angstroms, at about 4.2±0.5 degrees angstroms, at about 4.0±0.5 degrees angstroms, at about 3.4±0.5 degrees angstroms, and at about 2.9 degrees angstroms.

In some embodiments, the co-crystalline Form V of the compound of Formula I, Formula I-a, or Formula I-b (hereinafter the "co-crystalline Form V") is provided. In some embodiments, the co-crystalline Form V is characterized by an X-ray powder diffraction pattern comprising one or more peaks at about 7.0±0.5 degrees 2θ, at about 10.7±0.5 degrees 2θ, at about 14.4±0.5 degrees 2θ, at about 21.3±0.5 degrees 2θ, at about 24.1±0.5 degrees 2θ, at about 26.1±0.5 degrees 2θ, at about 26.6±0.5 degrees 2θ, at about 28.5±0.5 degrees 2θ, and at about 29.6±0.5 degrees 2θ. In some embodiments, the co-crystalline Form V characterized by an X-ray powder diffraction pattern comprising one or more d-spacing values at about 12.6±0.5 degrees angstroms, at about 8.3±0.5 degrees angstroms, at about 6.2±0.5 degrees angstroms, at about 4.2±0.5 degrees angstroms, at about 3.7±0.5 degrees angstroms, at about 3.4±0.5 degrees angstroms, at about 3.4±0.5 degrees angstroms, at about 3.1±0.5 degrees angstroms, and at about 3.0 degrees angstroms.

In some embodiments, the co-crystalline Form VI of the compound of Formula I, Formula I-a, or Formula I-b (hereinafter the "co-crystalline Form VI") is provided. In some embodiments, the co-crystalline Form VI is characterized by an X-ray powder diffraction pattern comprising one or more peaks at about 16.3±0.5 degrees 2θ, at about 18.1±0.5 degrees 2θ, at about 20.2±0.5 degrees 2θ, at about 24.7±0.5 degrees 2θ, at about 25.2±0.5 degrees 2θ, at about 30.4±0.5 degrees 2θ, and at about 30.9±0.5 degrees 2θ. In some embodiments, the co-crystalline Form VI characterized by an X-ray powder diffraction pattern comprising one or more d-spacing values at about 5.5±0.5 degrees angstroms, at about 4.9±0.5 degrees angstroms, at about 4.4±0.5 degrees angstroms, at about 3.6±0.5 degrees angstroms, at about 3.5±0.5 degrees angstroms, at about 2.9±0.5 degrees angstroms, and at about 2.9 degrees angstroms.

In some embodiments, the co-crystalline Form VII of the compound of Formula I, Formula I-a, or Formula I-b (hereinafter the "co-crystalline Form VII") is provided. In some embodiments, the co-crystalline Form VII is characterized by an X-ray powder diffraction pattern comprising one or more peaks at about 7.6±0.5 degrees 2θ, at about 10.8±0.5 degrees 2θ, at about 14.0±0.5 degrees 2θ, at about 15.2±0.5 degrees 2θ, at about 21.9±0.5 degrees 2θ, at about 22.8±0.5 degrees 2θ, and at about 29.8±0.5 degrees 2θ. In some embodiments, the co-crystalline Form VII characterized by an X-ray powder diffraction pattern comprising one or more d-spacing values at about 11.6±0.5 degrees angstroms, at about 8.2±0.5 degrees angstroms, at about 6.3±0.5 degrees angstroms, at about 5.8±0.5 degrees angstroms, at about 4.1±0.5 degrees angstroms, at about 3.9±0.5 degrees angstroms, and at about 3.0 degrees angstroms.

In some embodiments, a pharmaceutical composition comprising a co-crystalline form of the compound of any one of the Formulae, as described or provided for herein, such as Formula I, Formula I-a, and Formula I-b is provided. In some embodiments, a pharmaceutical composition comprising the co-crystalline Form I, Form II, Form III, Form IV, Form V, Form VI, or Form VII of the compound of Formula I, Formula I-a, or Formula I-b is provided. In some embodiments, a pharmaceutical composition comprising the co-crystalline Form I of the compound of Formula I, Formula I-a, or Formula I-b is provided. In some embodiments, a pharmaceutical composition comprising the co-crystalline Form II of the compound of Formula I, Formula I-a, or Formula I-b is provided. In some embodiments, a pharmaceutical composition comprising the co-crystalline Form III, of the compound of Formula I, Formula I-a, or Formula I-b is provided. In some embodiments, a pharmaceutical composition comprising the co-crystalline Form VI of the compound of Formula I, Formula I-a, or Formula I-b is provided. In some embodiments, a pharmaceutical composition comprising the co-crystalline Form V of the compound of Formula I, Formula I-a, or Formula I-b is provided. In some embodiments, a pharmaceutical composition comprising the co-crystalline Form VI of the compound of Formula I, Formula I-a, or Formula I-b is provided. In some embodiments, a pharmaceutical composition comprising the co-crystalline Form VII of the compound of Formula I, Formula I-a, or Formula I-b is provided.

In some embodiments, the compound of any one of the Formulae, as described or provided for herein, such as Formula IV, Formula IV-I, Formula IV-Ia, and Formula IV-Ib, can be crystallized without a coformer.

In some embodiments, the crystalline Form VIII of the compound of Formula IV-I, Formula IV-Ia, and Formula IV-Ib (hereinafter the "crystalline Form VIII") is provided.

In some embodiments, the crystalline Form VIII is characterized by an X-ray powder diffraction pattern comprising one or more peaks at about 10.5±0.5 degrees 2θ, at about 11.1±0.5 degrees 2θ, at about 14.6±0.5 degrees 2θ, at about 15.1±0.5 degrees 2θ, at about 17.0±0.5 degrees 2θ, at about 17.9±0.5 degrees 2θ, at about 18.2±0.5 degrees 2θ, at about 21.1±0.5 degrees 2θ, at about 22.2±0.5 degrees 2θ, at about 23.5±0.5 degrees 2θ, at about 25.5±0.5 degrees 2θ, at about 26.6±0.5 degrees 2θ, at about 26.9±0.5 degrees 2θ, at about 27.8±0.5 degrees 2θ, and at about 28.3±0.5 degrees 2θ. In some embodiments, the crystalline Form VIII characterized by an X-ray powder diffraction pattern comprising d-spacing values at about 8.41±0.5 degrees angstroms, at about 7.99±0.5 degrees angstroms, at about 6.05±0.5 degrees angstroms, at about 5.86±0.5 degrees angstroms, at about 5.22±0.5 degrees angstroms, at about 4.96±0.5 degrees angstroms, at about 4.87±0.5 degrees angstroms, at about 4.21±0.5 degrees angstroms, at about 4.00±0.5 degrees angstroms, at about 3.78±0.5 degrees angstroms, at about 3.49±0.5 degrees angstroms, at about 3.35±0.5 degrees angstroms, at about 3.32±0.5 degrees angstroms, at about 3.21±0.5 degrees angstroms, and at about 3.15±0.5 degrees angstroms In some embodiments, the pharmaceutical composition comprises a co-crystalline form of Forms I-VII, a co-crystalline form of the compound of Formula IV-I or the crystalline Form VIII as described or provided herein. In some embodiments, the pharmaceutical composition comprises the crystalline Form VIII, further comprising an additional drug for the treatment of a variety of an alcohol-related disorders, such as alcohol use disorder, alcohol-induced disorder, alcohol abuse, alcohol dependence, alcohol intoxication, alcohol withdrawal, and the like. In some embodiments, the pharmaceutical composition comprises the co-crystalline Form I. In some embodiments, the pharmaceutical composition comprises the co-crystalline Form II. In some embodiments, the pharmaceutical composition comprises the co-crystalline Form III. In some embodiments, the pharmaceutical composition comprises the co-crystalline Form VI. In some embodiments, the pharmaceutical composition comprises the co-crystalline Form V. In some embodiments, the pharmaceutical composition comprises the co-crystalline Form VI. In some embodiments, the pharmaceutical composition comprises the co-crystalline Form VII. In some embodiments, the pharmaceutical composition comprises the co-crystalline form of the compound of Formula IV-I. In some embodiments, the pharmaceutical composition comprises the crystalline Form VIII.

In some embodiments, processes for preparing crystalline forms of the compound of any one of the Formulae with or without a coformer, as described or provided for herein, such as Formula I, Formula III, and Formula IV, comprising crystallizing the compound to form the co-crystalline form and optionally isolating the crystalline form is provided.

In some embodiments, methods of treating and/or preventing the conditions described herein are provided. In some embodiments, the condition is an alcohol-related disorder such as, but not limited to, alcohol use disorder, alcohol-induced disorder, alcohol abuse, alcohol dependence, alcohol intoxication, alcohol withdrawal, and the like comprising administering to a subject in need thereof, a crystalline form of the compound of any one of the Formulae, as described or provided for herein, such as Formula I, Formula III, and Formula IV is provided. In some embodiments, the subject is diagnosed with the alcohol-related disorder.

In some embodiments, methods of reducing the amount of alcohol consumed in a subject with alcohol use disorder are provided. In some embodiments, the method comprises administering a pharmaceutical composition comprising a compound, a crystalline form, or a co-crystalline form provided for herein.

In some embodiments, methods of reducing alcoholic cravings in a subject with alcohol use disorder are provided. In some embodiments, the method comprises administering a pharmaceutical composition comprising a compound, a crystalline form, or a co-crystalline form provided for herein.

In some embodiments, methods of increasing the percentage of no heavy drinking days for a subject with alcohol use disorder are provided. In some embodiments, the method comprises administering a pharmaceutical composition comprising a compound, a crystalline form, or a co-crystalline form provided for herein.

The details of one or more embodiments are set forth in the description below. Other features, objects, and advantages of the present teachings will be apparent from the description of examples and also from the appending claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
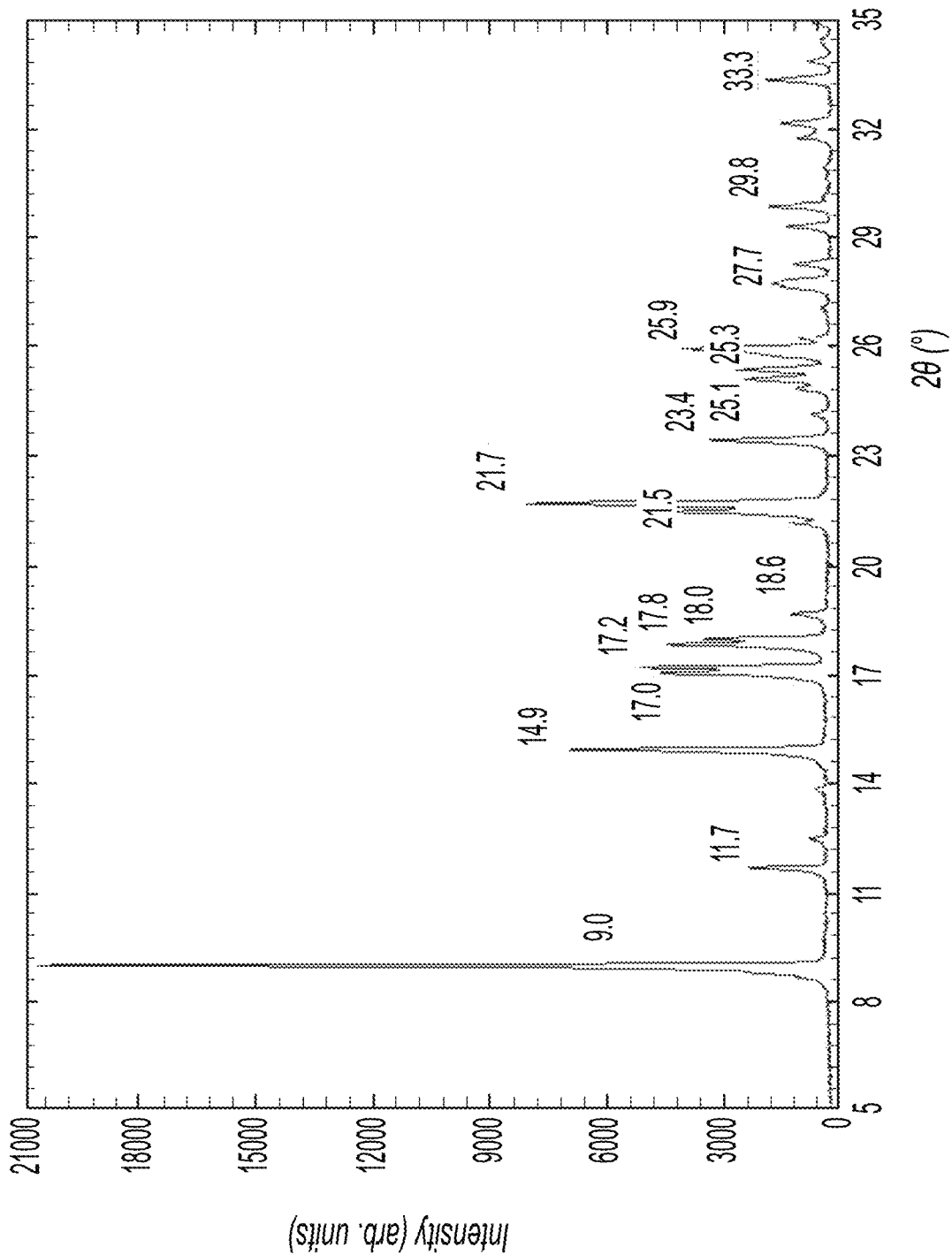
FIG. 1 shows X-ray powder diffraction pattern of the co-crystalline Form I of the compound of Formula I and urea.

The term "salt" or "salts" may refer to any acid addition salts, including addition salts of free acids or addition salts of free bases. All of these salts (or other similar salts) may be prepared by conventional means. All such salts are acceptable, provided that they are non-toxic and do not substantially interfere with the desired pharmacological activity.

The term "therapeutically effective amount" means the amount of a compound that, when administered to a mammal for treating a state, disorder or condition, is sufficient to effect a treatment (as defined below). The "therapeutically effective amount" will vary depending on the compound, the disease and its severity, the age, weight, physical condition and responsiveness of the mammal to be treated.

The term "pharmaceutically acceptable" means biologically or pharmacologically compatible for in vivo use in animals or humans, and preferably means approved by a regulatory agency of the Federal or a State government or listed in the U.S. Pharmacopeia or other generally recognized pharmacopeia for use in animals, and more particularly in humans.

As used herein, the terms "treat," "treated," or "treating" means both therapeutic treatment and prophylactic measures wherein the object is to slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of pain" or "treating pain" means an activity that alleviates or ameliorates any of the primary phenomena or secondary symptoms associated with the pain or other condition described herein.

The term "additive" is defined as the interaction of two or more agents so that their combined effect is the same as the sum of their individual effects. For example, if the effect of drug A alone in treating a disease is 25%, and the effect of drug B alone in treating a disease is 25%, but when the two drugs are combined, the effect in treating the disease is 50%, the effect of A and B is additive.

The term "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences. Mack Publishing Co. (A. R. Gennaro edit. 1985)) for use in animals, and more particularly in humans.

The term "about". "ca.", or "approximately" means plus or minus 5%. In some embodiments, the term "about". "ca.", or "approximately" means plus or minus 10%.

The present embodiments provide methods to crystallize a compound of any one of the Formulae with or without a coformer, as described or provided for herein.

In some embodiments, processes for preparing a co-crystalline form of the compound having a formula of

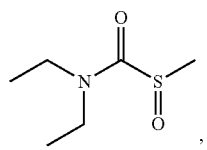

Formula I

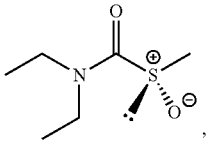

Formula I-a

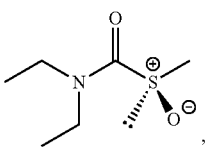

Formula I-b

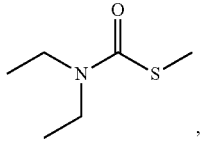

Formula II

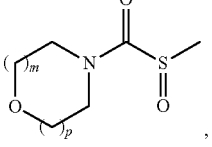

Formula III

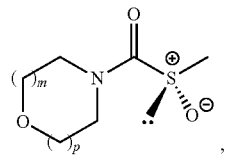

Formula III-a

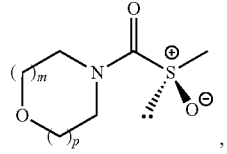

Formula III-b

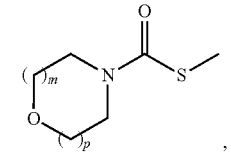

Formula VI

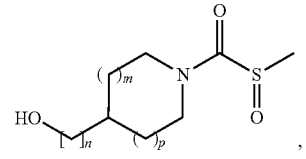

Formula IV

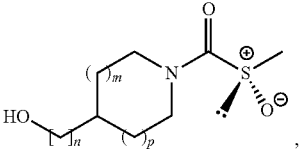

Formula IV-a

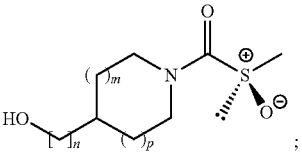

Formula IV-b

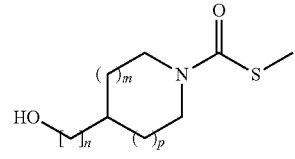

Formula V wherein n is 0-6, and a coformer as described or provided herein. In some embodiments, the process comprises co-crystallizing the compound and the coformer to form the co-crystalline form of the compound and the coformer and optionally isolating the co-crystalline form of the compound and the coformer. In some embodiments, the process comprises dry grinding the compound and the coformer to form the co-crystalline form therefrom. In some embodiments, the process comprises slurrying the compound and the coformer in an organic solvent to form the co-crystalline form therefrom. In some embodiments, the process further comprises washing the slurry with the organic solvent.

In some embodiments, the present embodiments provide methods to co-crystallize a compound having a formula of

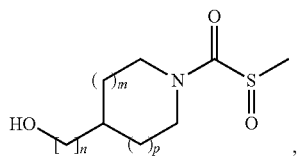

Formula IV

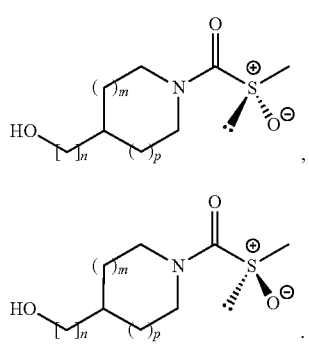

Formula IV-a

Formula IV-b

In some embodiments, n is 0-6. In some embodiments, n is 0-5. In some embodiments, n is 0-4. In some embodiments, n is 0-3. In some embodiments, n is 0-2. In some embodiments, n is 0 or 1. In some embodiments, n is 1-6. In some embodiments, n is 1-5. In some embodiments, n is 1-4. In some embodiments, n is 1-3. In some embodiments, n is 1 or 2. In some embodiments, n is 2-6. In some embodiments, n is 2-5. In some embodiments, n is 2-4. In some embodiments, n is 2 or 3. In some embodiments, n is 3-6. In some embodiments, n is 3-5. In some embodiments, n is 3 or 4. In some embodiments, n is 2 or 3. In some embodiments, n is 4-6. In some embodiments, n is 4 or 5. In some embodiments, n is 5 or 6. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, m is 0-6. In some embodiments, m is 0-5. In some embodiments, m is 0-4. In some embodiments, m is 0-3. In some embodiments, m is 0-2. In some embodiments, m is 0 or 1. In some embodiments, m is 1-6. In some embodiments, m is 1-5. In some embodiments, m is 1-4. In some embodiments, m is 1-3. In some embodiments, m is 1 or 2. In some embodiments, m is 2-6. In some embodiments, m is 2-5. In some embodiments, m is 2-4. In some embodiments, m is 2 or 3. In some embodiments, m is 3-6. In some embodiments, m is 3-5. In some embodiments, m is 3 or 4. In some embodiments, m is 2 or 3. In some embodiments, m is 4-6. In some embodiments, m is 4 or 5. In some embodiments, m is 5 or 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, p is 0-6. In some embodiments, p is 0-5. In some embodiments, p is 0-4. In some embodiments, p is 0-3. In some embodiments, p is 0-2. In some embodiments, p is 0 or 1. In some embodiments, p is 1-6. In some embodiments, p is 1-5. In some embodiments, p is 1-4. In some embodiments, p is 1-3. In some embodiments, p is 1 or 2. In some embodiments, p is 2-6. In some embodiments, p is 2-5. In some embodiments, p is 2-4. In some embodiments, p is 2 or 3. In some embodiments, p is 3-6. In some embodiments, p is 3-5. In some embodiments, p is 3 or 4. In some embodiments, p is 2 or 3. In some embodiments, p is 4-6. In some embodiments, p is 4 or 5. In some embodiments, p is 5 or 6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, the present embodiments provide methods to co-crystallize a compound having a formula of

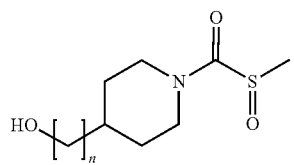

Formula IV and its enantiomers are compounds having the respective formulae of

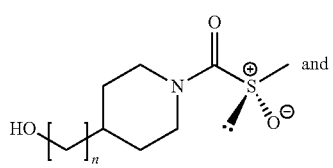

Formula IV-a

Formula IV-b

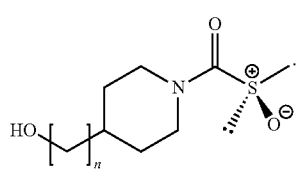

In some embodiments, n is 0-6. In some embodiments, n is 0-5. In some embodiments, n is 0-4. In some embodiments, n is 0-3. In some embodiments, n is 0-2. In some embodiments, n is 0 or 1. In some embodiments, n is 1-6. In some embodiments, n is 1-5. In some embodiments, n is 1-4. In some embodiments, n is 1-3. In some embodiments, n is 1 or 2. In some embodiments, n is 2-6. In some embodiments, n is 2-5. In some embodiments, n is 2-4. In some embodiments, n is 2 or 3. In some embodiments, n is 3-6. In some embodiments, n is 3-5. In some embodiments, n is 3 or 4. In some embodiments, n is 2 or 3. In some embodiments, n is 4-6. In some embodiments, n is 4 or 5. In some embodiments, n is 5 or 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, the present embodiments provide methods to co-crystallize a compound having a formula of

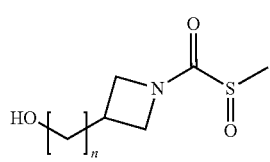

Formula VII and its enantiomers are compounds having the respective formulae of

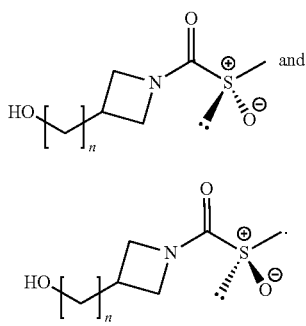

Formula VII-a

Formula VII-b

In some embodiments, n is 0-6. In some embodiments, n is 0-5. In some embodiments, n is 0-4. In some embodiments, n is 0-3. In some embodiments, n is 0-2. In some embodiments, n is 0 or 1. In some embodiments, n is 1-6. In some embodiments, n is 1-5. In some embodiments, n is 1-4. In some embodiments, n is 1-3. In some embodiments, n is 1 or 2. In some embodiments, n is 2-6. In some embodiments, n is 2-5. In some embodiments, n is 2-4. In some embodiments, n is 2 or 3. In some embodiments, n is 3-6. In some embodiments, n is 3-5. In some embodiments, n is 3 or 4. In some embodiments, n is 2 or 3. In some embodiments, n is 4-6. In some embodiments, n is 4 or 5. In some embodiments, n is 5 or 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, the present embodiments provide methods to co-crystallize a compound having a formula of

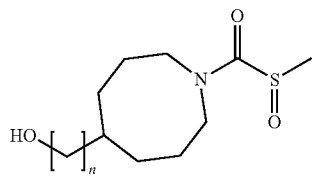

Formula VIII and its enantiomers are compounds having the respective formulae of

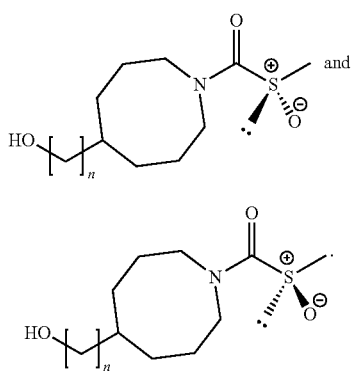

Formula VIII-a

Formula VIII-b

In some embodiments, n is 0-6. In some embodiments, n is 0-5. In some embodiments, n is 0-4. In some embodiments, n is 0-3. In some embodiments, n is 0-2. In some embodiments, n is 0 or 1. In some embodiments, n is 1-6. In some embodiments, n is 1-5. In some embodiments, n is 1-4. In some embodiments, n is 1-3. In some embodiments, n is 1 or 2. In some embodiments, n is 2-6. In some embodiments, n is 2-5. In some embodiments, n is 2-4. In some embodiments, n is 2 or 3. In some embodiments, n is 3-6. In some embodiments, n is 3-5. In some embodiments, n is 3 or 4. In some embodiments, n is 2 or 3. In some embodiments, n is 4-6. In some embodiments, n is 4 or 5. In some embodiments, n is 5 or 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, co-crystalline forms of the compound of Formula IV, Formula IV-a, or Formula IV-b with a coformer are provided. In some embodiments, co-crystalline forms of the compound of Formula IV with a coformer are provided. In some embodiments, co-crystalline forms of the compound of Formula IV-a with a coformer are provided. In some embodiments, co-crystalline forms of the compound of Formula IV-b with a coformer are provided.

In some embodiments, the present embodiments provide methods to co-crystallize a compound having a formula of

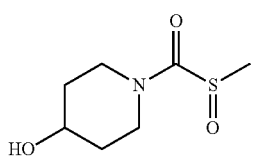

Formula IV-I and its enantiomers are compounds having the respective formulae of

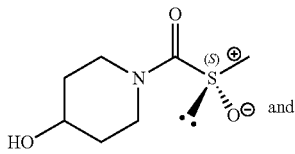

Formula IV-Ia

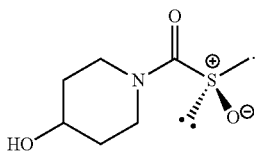

Formula IV-Ib

In some embodiments, the coformer is a coformer provided and described herein. In some embodiments, the coformer is trifluorotriiodobenzene, 4-aminobenzoic acid, L-aspartic acid, paracetamol, ellagic acid, 2-aminobenzoic acid, or urea, or any combination thereof. In some embodiments, the coformer is trifluorotriiodobenzene. In some embodiments, the coformer is 4-aminobenzoic acid. In some embodiments, the coformer is L-aspartic acid. In some embodiments, the coformer is paracetamol. In some embodiments, the coformer is ellagic acid, 2-aminobenzoic acid. In some embodiments, the coformer is or urea.

In some embodiments, co-crystalline forms of the compound of Formula III, Formula III-a, or Formula III-b with a coformer are provided. In some embodiments, co-crystalline forms of the compound of Formula III with a coformer are provided. In some embodiments, co-crystalline forms of the compound of Formula III-a with a coformer are provided. In some embodiments, co-crystalline forms of the compound of Formula III-b with a coformer are provided.

In some embodiments, the present embodiments provide methods to co-crystallize "(methylsulfinyl)(morpholino) methanone", which has a formula of

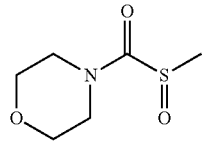

Formula III and its enantiomers are compounds having the respective formulae of

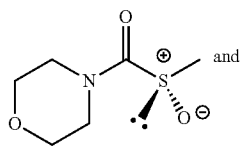

Formula III-a

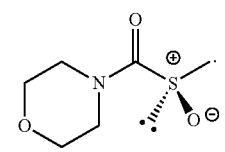

Formula III-b

In some embodiments, the present embodiments provide methods to co-crystallize "(methylsulfinyl)(morpholino) methanone", which has a formula of

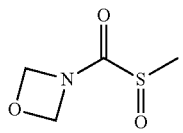

Formula IX and its enantiomers are compounds having the respective formulae of

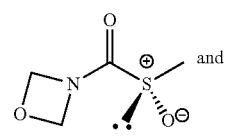

Formula IX-a

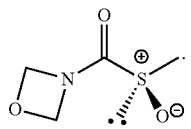

Formula IX-b

In some embodiments, the present embodiments provide methods to co-crystallize "(methylsulfinyl)(morpholino) methanone", which has a formula of

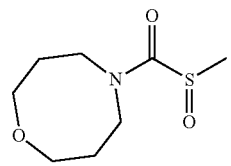

Formula X and its enantiomers are compounds having the respective formulae of

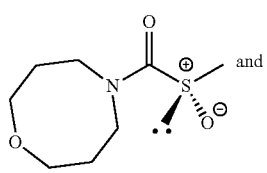

Formula X-a

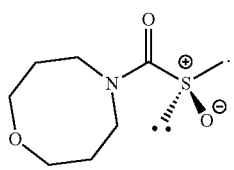

Formula X-b

In some embodiments, the present embodiments provide methods to co-crystallize a compound of Formula I can also be referred to as "S-methyl-N,N-diethylthiocarbamate sulfoxide", which has a formula of

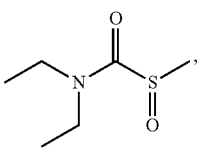

Formula I and a compound of Formula I-a or Formula I-b can be referred to a compound having a respective formulae of

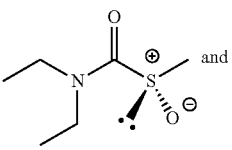

Formula I-a

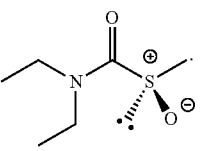

Formula I-b

In some embodiments, co-crystalline forms of the compound of Formula I, Formula I-a, or Formula I-b with a coformer are provided. In some embodiments, co-crystalline forms of the compound of Formula I with a coformer are provided. In some embodiments, co-crystalline forms of the compound of Formula I-a with a coformer are provided. In some embodiments, co-crystalline forms of the compound of Formula I-b with a coformer are provided. In some embodiments, the coformer is a coformer provided and described herein. In some embodiments, the coformer is urea, 3,5-dihydroxybenzoic acid, trimesic acid, ellagic acid, $MgCl_2$, or $CaCl_2$, or any combination thereof. In some embodiments, the coformer is urea. In some embodiments, the coformer is 3,5-dihydroxybenzoic acid. In some embodiments, the coformer is trimesic acid. In some embodiments, the coformer is ellagic acid. In some embodiments, the coformer is $MgCl_2$. In some embodiments, the coformer is or $CaCl_2$. In some embodiments, the coformer is a combination two or more of urea, 3,5-dihydroxybenzoic acid, trimesic acid, ellagic acid, $MgCl_2$, and $CaCl_2$.

A compound of any one of the Formulae, as described or provided for herein, or the pharmaceutically acceptable salt thereof, can be prepared according to the synthesis described in U.S. Patent Provisional Application No. 63/119,211, which is hereby incorporated by reference in its entirety or according to the synthesis as described or provided for herein. For example, in some embodiments, a compound of Formula I, Formula III, or Formula IV or the pharmaceutically acceptable salt thereof, can be prepared according to the synthesis described in U.S. Patent Provisional Application No. 63/119,211, which is hereby incorporated by reference in its entirety. For another example, in some embodiments, a compound of Formula IV, Formula IV-a, or Formula IV-b, or the pharmaceutically acceptable salt thereof, can be prepared according to the synthesis as described or provided for herein.

An oil form of the compound of Formula I, Formula I-a, or Formula I-b, or the pharmaceutically acceptable salt thereof, can be prepared according to the synthesis described in U.S. Patent Provisional Application No. 63/119,211, which is hereby incorporated by reference in its entirety. The oil form of the compound of Formula I. Formula I-a, or Formula I-b or the pharmaceutically acceptable salt thereof can then be isolated using silica gel chromatographs. Silica gel chromatographs may not be feasible for large-scale manufacturing of the compound for commercial production. Additionally, the oil form or the compound of Formula I, Formula I-a, or Formula I-b is difficult to work with and is not advantageous to use in pharmaceutical preparation. Therefore, a co-crystalline form is needed that can be better used in the manufacturing and use of pharmaceutical compositions. Although in some instances, preparing crystal forms of compounds can be straightforward, this was not the case for a compound of Formula I, Formula I-a, or Formula I-b. The present embodiments provide for the surprising and unexpected result of co-crystalline forms of Formula I. Formula I-a, or Formula I-b. In some embodiments, the co-crystalline form is Form I, Form II. Form III, Form IV, Form V. Form VI, or Form VII, as provided for herein. In some embodiments, the co-crystalline form is Form I, as provided for herein. In some embodiments, the co-crystalline form is Form II, as provided for herein. In some embodiments, the co-crystalline form is Form III, as provided for herein. In some embodiments, the co-crystalline form is Form VI, as provided for herein. In some embodiments, the co-crystalline form is Form V, as provided for herein. In some embodiments, the co-crystalline form is Form VI, as provided for herein. In some embodiments, the co-crystalline form is Form VII, as provided for herein.

In some embodiments, the co-crystalline Form I of the compound of Formula I. Formula I-a, or Formula I-b (hereinafter the "co-crystalline Form I") is provided.

In some embodiments, the co-crystalline Form I is characterized by an X-ray powder diffraction pattern substantially, as shown in FIG. 1. In some embodiments, the co-crystalline Form I is characterized by an X-ray powder diffraction pattern comprising one or more peaks, as provided in Table 4. In some embodiments, the co-crystalline Form I is characterized by an X-ray powder diffraction pattern comprising substantially all of, or all of, the peaks as provided in Table 4.

In some embodiments, the co-crystalline Form I is characterized by an X-ray powder diffraction pattern comprising a peak at about 9.0±0.5 degrees 2θ.

In some embodiments, the co-crystalline Form I is characterized by an X-ray powder diffraction pattern comprising a peak at about 11.7±0.5 degrees 2θ.

In some embodiments, the co-crystalline Form I is characterized by an X-ray powder diffraction pattern comprising a peak at about 14.9±0.5 degrees 2θ.

In some embodiments, the co-crystalline Form I is characterized by an X-ray powder diffraction pattern comprising a peak at about 17.0±0.5 degrees 2θ.

In some embodiments, the co-crystalline Form I is characterized by an X-ray powder diffraction pattern comprising a peak at about 17.2±0.5 degrees 2θ.

In some embodiments, the co-crystalline Form I is characterized by an X-ray powder diffraction pattern comprising a peak at about 17.8±0.5 degrees 2θ.

In some embodiments, the co-crystalline Form I is characterized by an X-ray powder diffraction pattern comprising a peak at about 18.0±0.5 degrees 2θ.

In some embodiments, the co-crystalline Form I is characterized by an X-ray powder diffraction pattern comprising a peak at about 18.6±0.5 degrees 2θ.

In some embodiments, the co-crystalline Form I is characterized by an X-ray powder diffraction pattern comprising a peak at about 21.1±0.5 degrees 2θ.

In some embodiments, the co-crystalline Form I is characterized by an X-ray powder diffraction pattern comprising a peak at about 21.5±0.5 degrees 2θ.

In some embodiments, the co-crystalline Form I is characterized by an X-ray powder diffraction pattern comprising a peak at about 21.7±0.5 degrees 2θ.

In some embodiments, the co-crystalline Form I is characterized by an X-ray powder diffraction pattern comprising a peak at about 23.4±0.5 degrees 2θ.

In some embodiments, the co-crystalline Form I is characterized by an X-ray powder diffraction pattern comprising a peak at about 24.8±0.5 degrees 2θ.

In some embodiments, the co-crystalline Form I is characterized by an X-ray powder diffraction pattern comprising a peak at about 25.1±0.5 degrees 2θ.

In some embodiments, the co-crystalline Form I is characterized by an X-ray powder diffraction pattern comprising a peak at about 25.3±0.5 degrees 2θ.

In some embodiments, the co-crystalline Form I is characterized by an X-ray powder diffraction pattern comprising a peak at about 25.9±0.5 degrees 2θ.

In some embodiments, the co-crystalline Form I is characterized by an X-ray powder diffraction pattern comprising a peak at about 26.2±0.5 degrees 2θ.

In some embodiments, the co-crystalline Form I is characterized by an X-ray powder diffraction pattern comprising a peak at about 27.7±0.5 degrees 2θ.

In some embodiments, the co-crystalline Form I is characterized by an X-ray powder diffraction pattern comprising a peak at about 28.2±0.5 degrees 2θ.

In some embodiments, the co-crystalline Form I is characterized by an X-ray powder diffraction pattern comprising a peak at about 29.3±0.5 degrees 2θ.

In some embodiments, the co-crystalline Form I is characterized by an X-ray powder diffraction pattern comprising a peak at about 29.8±0.5 degrees 2θ.

In some embodiments, the co-crystalline Form I is characterized by an X-ray powder diffraction pattern comprising a peak at about 31.7±0.5 degrees 2θ.

In some embodiments, the co-crystalline Form I is characterized by an X-ray powder diffraction pattern comprising a peak at about 32.1±0.5 degrees 2θ.

In some embodiments, the co-crystalline Form I is characterized by an X-ray powder diffraction pattern comprising a peak at about 33.3±0.5 degrees 2θ.

In some embodiments, the co-crystalline Form I is characterized by an X-ray powder diffraction pattern comprising peaks at about 9.0±0.5 degrees 2θ and at about 14.9±0.5 degrees 2θ.

In some embodiments, the co-crystalline Form I is characterized by an X-ray powder diffraction pattern comprising peaks at about 9.0±0.5 degrees 2θ and at about 21.7±0.5 degrees 2θ.

In some embodiments, the co-crystalline Form I is characterized by an X-ray powder diffraction pattern comprising peaks at about 14.9±0.5 degrees 2θ and at about 21.7±0.5 degrees 2θ.

In some embodiments, the co-crystalline Form I is characterized by an X-ray powder diffraction pattern comprising peaks at about 9.0±0.5 degrees 2θ, at about 14.9±0.5 degrees 2θ, and at about 21.7±0.5 degrees 2θ.

In some embodiments, the co-crystalline Form I is characterized by an X-ray powder diffraction pattern comprising peaks at about 9.0±0.5 degrees 2θ, at about 14.9±0.5 degrees 2θ, at about 17.0±0.5 degrees 2θ, at about 17.2±0.5 degrees 2θ, at about 17.8±0.5 degrees 2θ, at about 21.5±0.5 degrees 2θ, and at about 21.7±0.5 degrees 2θ.

In some embodiments, the co-crystalline Form I is characterized by an X-ray powder diffraction pattern comprising peaks at about 9.0±0.5 degrees 2θ, at about 14.9±0.5 degrees 2θ, at about 17.0±0.5 degrees 2θ, at about 17.2±0.5 degrees 2θ, at about 17.8±0.5 degrees 2θ, at about 21.5±0.5 degrees 2θ, at about 21.7±0.5 degrees 2θ, and at about 25.9±0.5 degrees 2θ.

In some embodiments, the co-crystalline Form I is characterized by an X-ray powder diffraction pattern comprising peaks at about 9.0±0.5 degrees 2θ, at about 11.7±0.5 degrees 2θ, at about 14.9±0.5 degrees 2θ, at about 17.0±0.5 degrees 2θ, at about 17.2±0.5 degrees 2θ, at about 17.8±0.5 degrees 2θ, at about 18.0±0.5 degrees 2θ, at about 21.5±0.5 degrees 2θ, at about 21.7±0.5 degrees 2θ, at about 23.4±0.5 degrees 2θ, at about 25.1±0.5 degrees 2θ, at about 25.3±0.5 degrees 2θ, at about 25.9±0.5 degrees 2θ, at about 27.7±0.5 degrees 2θ, at about 29.8±0.5 degrees 2θ, and 33.3±0.5 degrees 2θ.

In some embodiments, the co-crystalline Form I is characterized by an X-ray powder diffraction pattern comprising one or more peaks at about one or more peaks at about 9.0±0.5 degrees 2θ, at about 11.7±0.5 degrees 2θ, at about 14.9±0.5 degrees 2θ, at about 17.0±0.5 degrees 2θ, at about 17.2±0.5 degrees 2θ, at about 17.8±0.5 degrees 2θ, at about 18.0±0.5 degrees 2θ, at about 18.6±0.5 degrees 2θ, at about 21.1±0.5 degrees 2θ, at about 21.5±0.5 degrees 2θ, at about 21.7±0.5 degrees 2θ, at about 23.4±0.5 degrees 2θ, at about 24.8±0.5 degrees 2θ, at about 25.1±0.5 degrees 2θ, at about 25.3±0.5 degrees 2θ, at about 25.9±0.5 degrees 2θ, at about 26.2±0.5 degrees 2θ, at about 27.7±0.5 degrees 2θ, at about 28.2±0.5 degrees 2θ, at about 29.3±0.5 degrees 2θ, at about 29.8±0.5 degrees 2θ, at about 31.7±0.5 degrees 2θ, at about 32.1±0.5 degrees 2θ, and at about 33.3±0.5 degrees 2θ.

Figure 2:
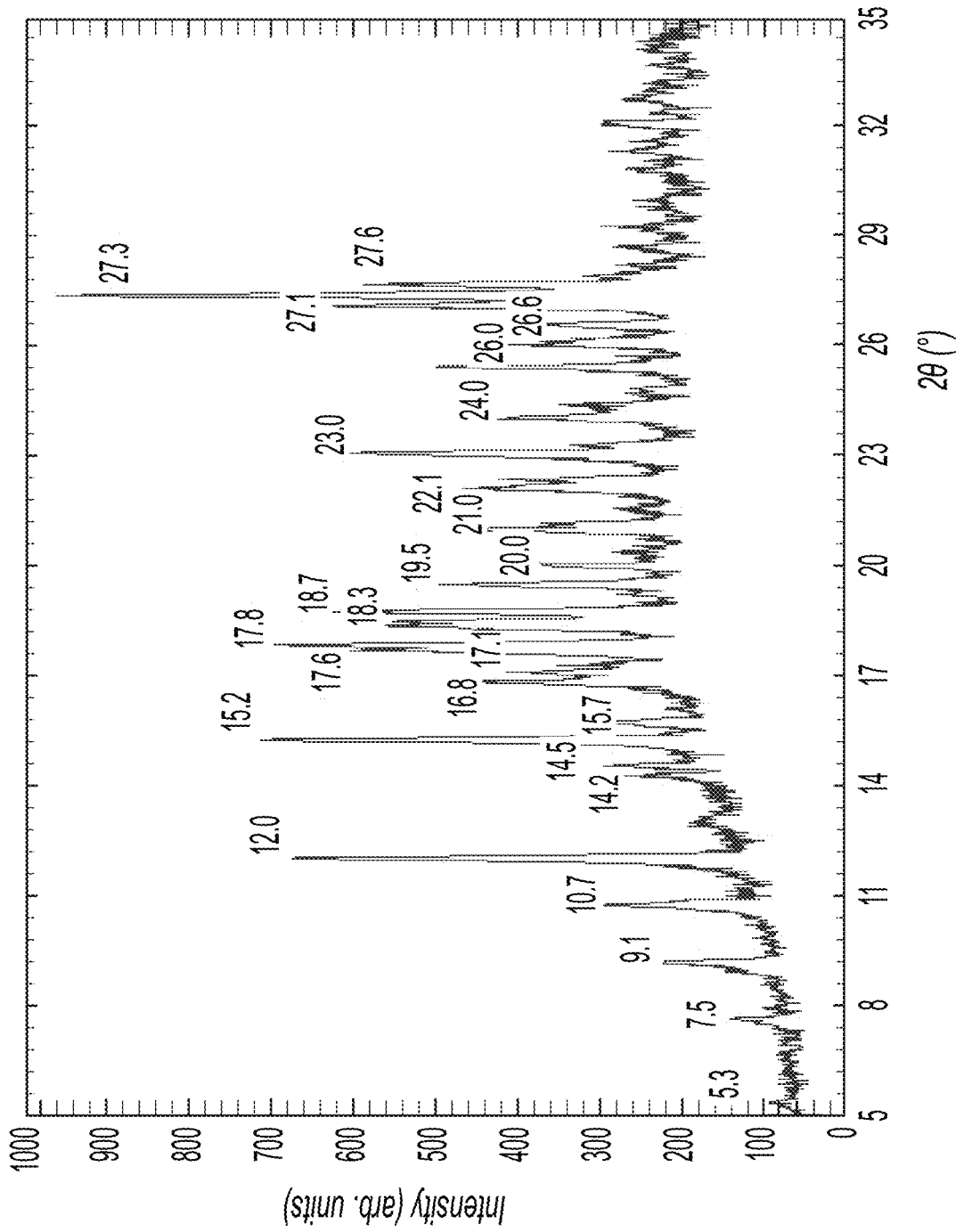
FIG. 2 shows X-ray powder diffraction pattern of the co-crystalline Form II of the compound of Formula I and trimesic acid.

In some embodiments, the co-crystalline Form II is characterized by an X-ray powder diffraction pattern substantially, as shown in FIG. 2. In some embodiments, the co-crystalline Form II is characterized by an X-ray powder diffraction pattern comprising one or more peaks, as provided in Table 5. In some embodiments, the co-crystalline Form II is characterized by an X-ray powder diffraction pattern comprising substantially all of, or all of, the peaks as provided in Table 5.

In some embodiments, the co-crystalline Form II is characterized by an X-ray powder diffraction pattern comprising a peak at about 9.1±0.5 degrees 2θ.

In some embodiments, the co-crystalline Form II is characterized by an X-ray powder diffraction pattern comprising a peak at about 10.7±0.5 degrees 2θ.

In some embodiments, the co-crystalline Form II is characterized by an X-ray powder diffraction pattern comprising a peak at about 12.0±0.5 degrees 2θ.

In some embodiments, the co-crystalline Form II is characterized by an X-ray powder diffraction pattern comprising a peak at about 15.2±0.5 degrees 2θ.

In some embodiments, the co-crystalline Form II is characterized by an X-ray powder diffraction pattern comprising a peak at about 17.6±0.5 degrees 2θ.

In some embodiments, the co-crystalline Form D is characterized by an X-ray powder diffraction pattern comprising a peak at about 17.8±0.5 degrees 2θ.

In some embodiments, the co-crystalline Form II is characterized by an X-ray powder diffraction pattern comprising a peak at about 18.3±0.5 degrees 2θ.

In some embodiments, the co-crystalline Form U is characterized by an X-ray powder diffraction pattern comprising a peak at about 18.4±0.5 degrees 2θ.

In some embodiments, the co-crystalline Form H is characterized by an X-ray powder diffraction pattern comprising a peak at about 18.7±0.5 degrees 2θ.

In some embodiments, the co-crystalline Form U is characterized by an X-ray powder diffraction pattern comprising a peak at about 19.5±0.5 degrees 2θ.

In some embodiments, the co-crystalline Form II is characterized by an X-ray powder diffraction pattern comprising a peak at about 22.1±0.5 degrees 2θ.

In some embodiments, the co-crystalline Form II is characterized by an X-ray powder diffraction pattern comprising a peak at about 23.0±0.5 degrees 2θ.

In some embodiments, the co-crystalline Form D is characterized by an X-ray powder diffraction pattern comprising a peak at about 24.0±0.5 degrees 2θ.

In some embodiments, the co-crystalline Form II is characterized by an X-ray powder diffraction pattern comprising a peak at about 25.4±0.5 degrees 2θ.

In some embodiments, the co-crystalline Form U is characterized by an X-ray powder diffraction pattern comprising a peak at about 27.1±0.5 degrees 2θ.

In some embodiments, the co-crystalline Form II is characterized by an X-ray powder diffraction pattern comprising a peak at about 27.3±0.5 degrees 2θ.

In some embodiments, the co-crystalline Form U is characterized by an X-ray powder diffraction pattern comprising a peak at about 27.6±0.5 degrees 2θ.

In some embodiments, the co-crystalline Form H is characterized by an X-ray powder diffraction pattern comprising peaks at about 12.0±0.5 degrees 2θ and at about 15.2±0.5 degrees 2θ.

In some embodiments, the co-crystalline Form II is characterized by an X-ray powder diffraction pattern comprising peaks at about 12.0±0.5 degrees 2θ and at about 17.8±0.5 degrees 2θ.

In some embodiments, the co-crystalline Form H is characterized by an X-ray powder diffraction pattern comprising peaks at about 12.0±0.5 degrees 2θ and at about 27.3±0.5 degrees 2θ.

In some embodiments, the co-crystalline Form U is characterized by an X-ray powder diffraction pattern comprising peaks at about 15.2±0.5 degrees 2θ and at about 17.8±0.5 degrees 2θ.

In some embodiments, the co-crystalline Form II is characterized by an X-ray powder diffraction pattern comprising peaks at about 15.2±0.5 degrees 2θ and at about 27.3±0.5 degrees 2θ.

In some embodiments, the co-crystalline Form II is characterized by an X-ray powder diffraction pattern comprising peaks at about 17.8±0.5 degrees 2θ and at about 27.3±0.5 degrees 2θ.

In some embodiments, the co-crystalline Form U is characterized by an X-ray powder diffraction pattern comprising peaks at about 12.0±0.5 degrees 2θ, at about 15.2±0.5 degrees 2θ, and at about 17.8±0.5 degrees 2θ.

In some embodiments, the co-crystalline Form II is characterized by an X-ray powder diffraction pattern comprising peaks at about 12.0±0.5 degrees 2θ, at about 15.2±0.5 degrees 2θ, and at about 27.3±0.5 degrees 2θ.

In some embodiments, the co-crystalline Form II is characterized by an X-ray powder diffraction pattern comprising peaks at about 12.0±0.5 degrees 2θ, at about 17.8±0.5 degrees 2θ, and at about 27.3±0.5 degrees 2θ.

In some embodiments, the co-crystalline Form U is characterized by an X-ray powder diffraction pattern comprising peaks at about 15.2±0.5 degrees 2θ, at about 17.8±0.5 degrees 2θ, and at about 27.3±0.5 degrees 2θ.

In some embodiments, the co-crystalline Form II is characterized by an X-ray powder diffraction pattern comprising peaks at about 12.0±0.5 degrees 2θ, at about 15.2±0.5 degrees 2θ, at about 17.8±0.5 degrees 2θ, and at about 27.3±0.5 degrees 2θ.

In some embodiments, the co-crystalline Form H is characterized by an X-ray powder diffraction pattern comprising peaks at about 12.0±0.5 degrees 2θ, at about 15.2±0.5 degrees 2θ, at about 17.8±0.5 degrees 2θ, at about 18.7±0.5 degrees 2θ, at about 23.0±0.5 degrees 2θ, at about 27.1±0.5 degrees 2θ, and at about 27.3±0.5 degrees 2θ.

In some embodiments, the co-crystalline Form II is characterized by an X-ray powder diffraction pattern comprising peaks at about 9.1±0.5 degrees 2θ, at about 10.7±0.5 degrees 2θ, at about 12.0±0.5 degrees 2θ, at about 15.2±0.5 degrees 2θ, at about 17.6±0.5 degrees 2θ, at about 17.8±0.5 degrees 2θ, at about 18.3±0.5 degrees 2θ, at about 18.4±0.5 degrees 2θ, at about 18.7±0.5 degrees 2θ, at about 19.5±0.5 degrees 2θ, at about 22.1±0.5 degrees 2θ, at about 23.0±0.5 degrees 2θ, at about 24.0±0.5 degrees 2θ, at about 25.4±0.5 degrees 2θ, at about 27.1±0.5 degrees 2θ, at about 27.3±0.5 degrees 2θ, and at about 27.6±0.5 degrees 2θ.

In some embodiments, the co-crystalline Form U is characterized by an X-ray powder diffraction pattern comprising one or more peaks at about 7.6±0.5 degrees 2θ, at about 9.1±0.5 degrees 2θ, at about 10.7±0.5 degrees 2θ, at about 12.0±0.5 degrees 2θ, at about 14.5±0.5 degrees 2θ, at about 15.2±0.5 degrees 2θ, at about 15.7±0.5 degrees 2θ, at about 16.8±0.5 degrees 2θ, at about 17.1±0.5 degrees 2θ, at about 17.6±0.5 degrees 2θ, at about 17.8±0.5 degrees 2θ, at about 18.3±0.5 degrees 2θ, at about 18.4±0.5 degrees 2θ, at about 18.7±0.5 degrees 2θ, at about 19.5±0.5 degrees 2θ, at about 20.0±0.5 degrees 2θ, at about 21.0±0.5 degrees 2θ, at about 22.1±0.5 degrees 2θ, at about 22.3±0.5 degrees 2θ, at about 23.0±0.5 degrees 2θ, at about 24.0±0.5 degrees 2θ, at about 25.4±0.5 degrees 2θ, at about 26.0±0.5 degrees 2θ, at about 26.6±0.5 degrees 2θ, at about 27.1±0.5 degrees 2θ, at about 27.3±0.5 degrees 2θ, and at about 27.6±0.5 degrees 2θ.

In some embodiments, the co-crystalline Form H is characterized by an X-ray powder diffraction pattern comprising one or more peaks at about 5.3±0.5 degrees 2θ, at about 7.6±0.5 degrees 2θ, at about 9.1±0.5 degrees 2θ, at about 10.7±0.5 degrees 2θ, at about 12.0±0.5 degrees 2θ, at about 14.2±0.5 degrees 2θ, at about 14.5±0.5 degrees 2θ, at about 15.2±0.5 degrees 2θ, at about 15.7±0.5 degrees 2θ, at about 16.8±0.5 degrees 2θ, at about 17.1±0.5 degrees 2θ, at about 17.2±0.5 degrees 2θ, at about 17.6±0.5 degrees 2θ, at about 17.8±0.5 degrees 2θ, at about 18.3±0.5 degrees 2θ, at about 18.4±0.5 degrees 2θ, at about 18.7±0.5 degrees 2θ, at about 19.5±0.5 degrees 2θ, at about 20.0±0.5 degrees 2θ, at about 21.0±0.5 degrees 2θ, at about 22.1±0.5 degrees 2θ, at about 22.3±0.5 degrees 2θ, at about 23.0±0.5 degrees 2θ, at about 23.3±0.5 degrees 2θ, at about 24.0±0.5 degrees 2θ, at about 24.4±0.5 degrees 2θ, at about 25.4±0.5 degrees 2θ, at about 26.0±0.5 degrees 2θ, at about 26.6±0.5 degrees 2θ, at about 27.1±0.5 degrees 2θ, at about 27.3±0.5 degrees 2θ, and at about 27.6±0.5 degrees 2θ.

In some embodiments, the co-crystalline Form II is characterized by an X-ray powder diffraction pattern comprising one or more peaks at about 5.3±0.5 degrees 2θ, at about 7.6±0.5 degrees 2θ, at about 9.1±0.5 degrees 2θ, at about 10.7±0.5 degrees 2θ, at about 12.0±0.5 degrees 2θ, at about 14.2±0.5 degrees 2θ, at about 14.5±0.5 degrees 2θ, at about 15.2±0.5 degrees 2θ, at about 15.7±0.5 degrees 2θ, at about 16.8±0.5 degrees 2θ, at about 17.1±0.5 degrees 2θ, at about 17.2±0.5 degrees 2θ, at about 17.6±0.5 degrees 2θ, at about 17.8±0.5 degrees 2θ, at about 18.3±0.5 degrees 2θ, at about 18.4±0.5 degrees 2θ, at about 18.7±0.5 degrees 2θ, at about 19.5±0.5 degrees 2θ, at about 20.0±0.5 degrees 2θ, at about 21.0±0.5 degrees 2θ, at about 22.1±0.5 degrees 2θ, at about 22.3±0.5 degrees 2θ, at about 23.0±0.5 degrees 2θ, at about 23.3±0.5 degrees 2θ, at about 24.0±0.5 degrees 2θ, at about 24.4±0.5 degrees 2θ, at about 25.4±0.5 degrees 2θ, at about 26.0±0.5 degrees 2θ, at about 26.6±0.5 degrees 2θ, at about 27.1±0.5 degrees 2θ, at about 27.3±0.5 degrees 2θ, and at about 27.6±0.5 degrees 2θ.

Figure 3:
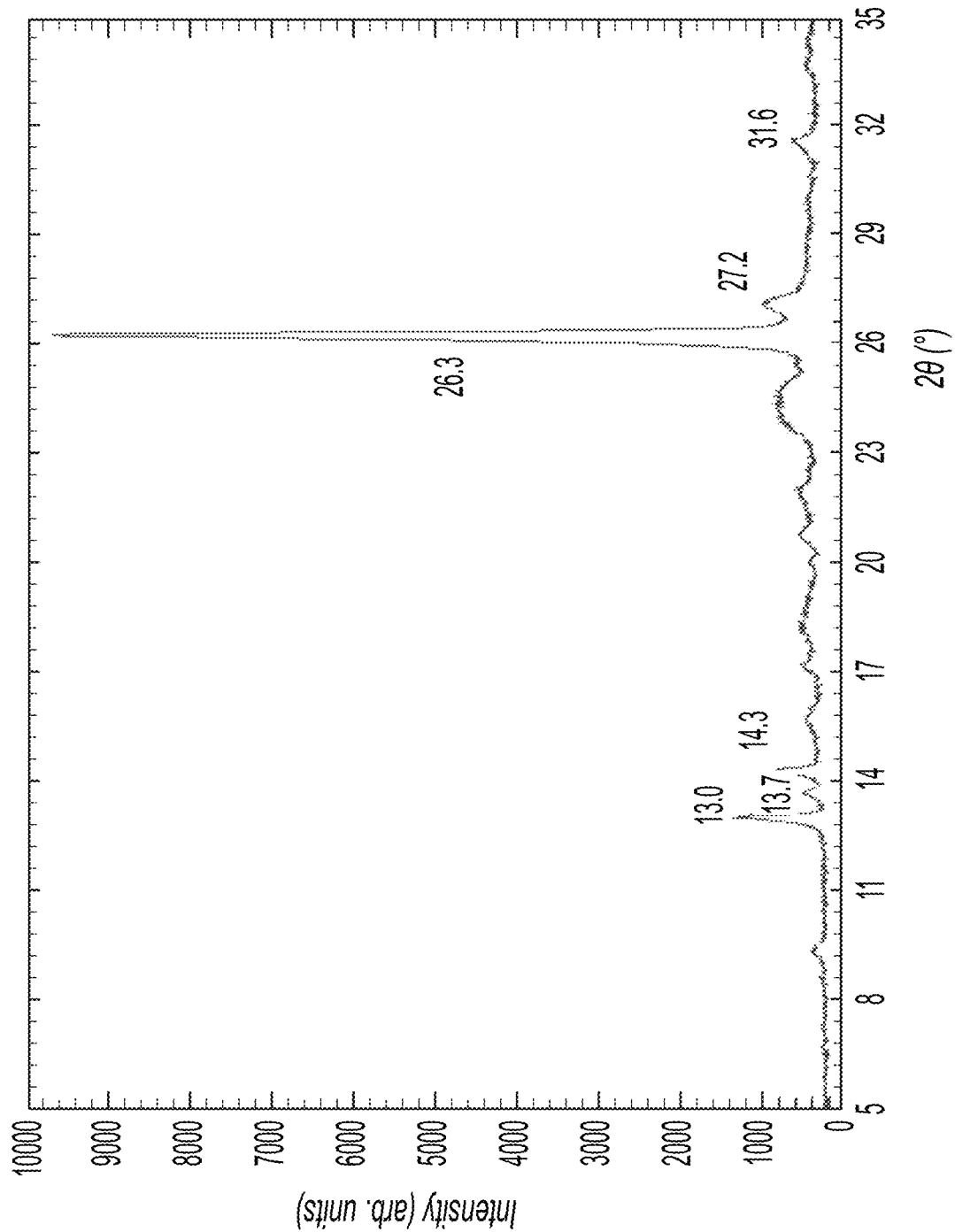
FIG. 3 shows X-ray powder diffraction pattern of the co-crystalline Form III of the compound of Formula I and 3,5-dihydroxybenzoic acid at a molar ratio of 1:2.

In some embodiments, the co-crystalline Form III is characterized by an X-ray powder diffraction pattern substantially, as shown in FIG. 3. In some embodiments, the co-crystalline Form III is characterized by an X-ray powder diffraction pattern comprising one or more peaks, as provided in Table 6. In some embodiments, the co-crystalline Form III is characterized by an X-ray powder diffraction pattern comprising substantially all of, or all of, the peaks as provided in Table 6.

In some embodiments, the co-crystalline Form III is characterized by an X-ray powder diffraction pattern comprising a peak at about 13.0±0.5 degrees 2θ.

In some embodiments, the co-crystalline Form III is characterized by an X-ray powder diffraction pattern comprising a peak at about 13.7±0.5 degrees 2θ.

In some embodiments, the co-crystalline Form III is characterized by an X-ray powder diffraction pattern comprising a peak at about 14.3±0.5 degrees 2θ

In some embodiments, the co-crystalline Form III is characterized by an X-ray powder diffraction pattern comprising a peak at about 26.3±0.5 degrees 2θ.

In some embodiments, the co-crystalline Form III is characterized by an X-ray powder diffraction pattern comprising a peak at about 27.2±0.5 degrees 2θ.

In some embodiments, the co-crystalline Form III is characterized by an X-ray powder diffraction pattern comprising a peak at about 31.6±0.5 degrees 2θ.

In some embodiments, the co-crystalline Form III is characterized by an X-ray powder diffraction pattern comprising peaks at about 13.0±0.5 degrees 2θ and at about 26.3±0.5 degrees 2θ.

In some embodiments, the co-crystalline Form III is characterized by an X-ray powder diffraction pattern comprising peaks at about 13.0±0.5 degrees 2θ, at about 14.3±0.5 degrees 2θ, at about 26.3±0.5 degrees 2θ, and at about 27.2±0.5 degrees 2θ.

In some embodiments, the co-crystalline Form III is characterized by an X-ray powder diffraction pattern comprising one or more peaks at about 13.0±0.5 degrees 2θ, at about 13.7±0.5 degrees 2θ, at about 14.3±0.5 degrees 2θ, at about 26.3±0.5 degrees 2θ, at about 27.2±0.5 degrees 2θ, and at about 31.6±0.5 degrees 2θ.

Figure 4:
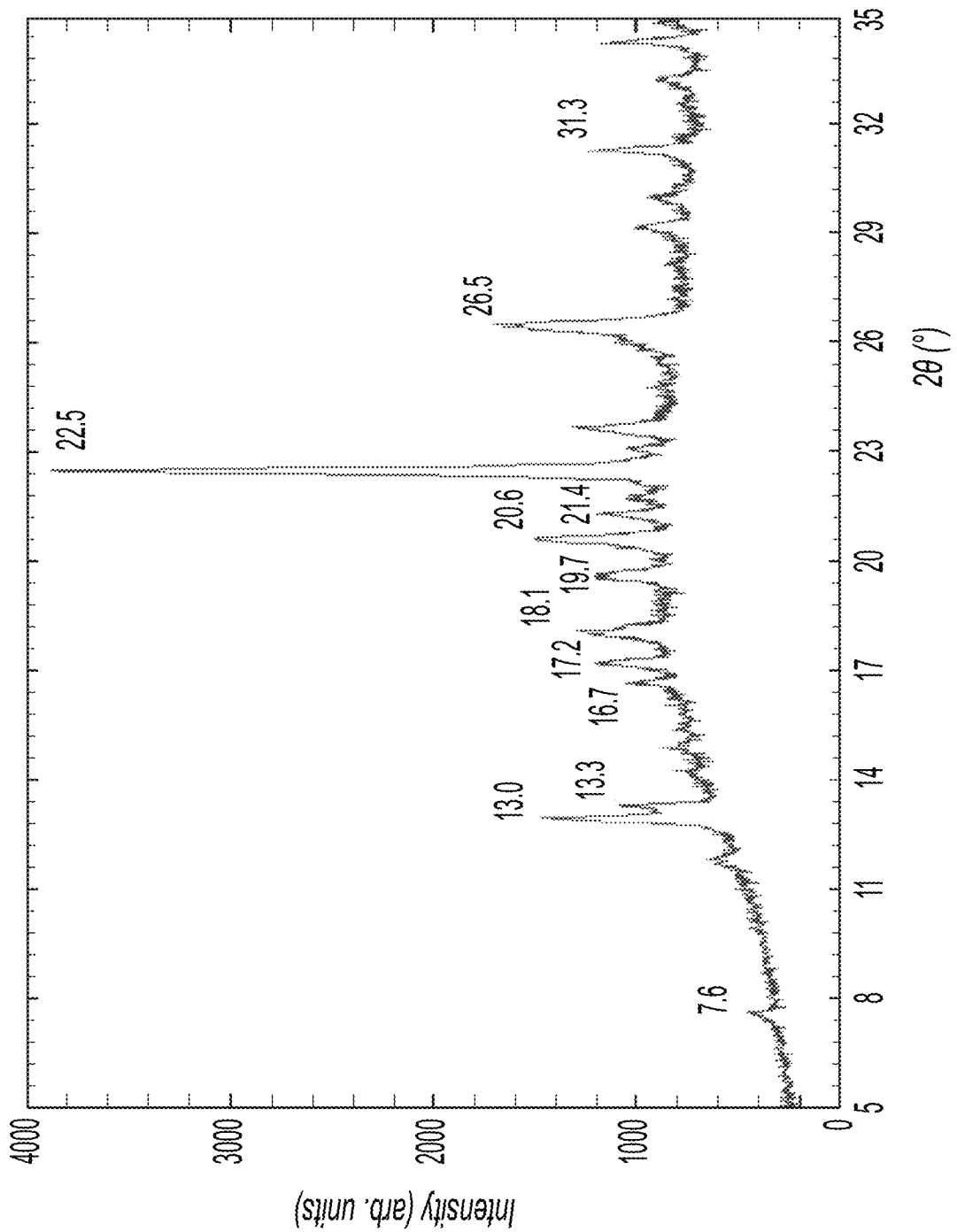
FIG. 4 shows X-ray powder diffraction pattern of the co-crystalline Form IV of the compound of Formula I and 3,5-dihydroxybenzoic acid at a molar ratio of 1:1.

In some embodiments, the co-crystalline Form IV is characterized by an X-ray powder diffraction pattern substantially, as shown in FIG. 4. In some embodiments, the co-crystalline Form IV is characterized by an X-ray powder diffraction pattern comprising one or more peaks, as provided in Table 7. In some embodiments, the co-crystalline Form IV is characterized by an X-ray powder diffraction pattern comprising substantially all of, or all of, the peaks as provided in Table 7.

In some embodiments, the co-crystalline Form IV is characterized by an X-ray powder diffraction pattern comprising a peak at about 13.0±0.5 degrees 2θ.

In some embodiments, the co-crystalline Form IV is characterized by an X-ray powder diffraction pattern comprising a peak at about 13.3±0.5 degrees 2θ.

In some embodiments, the co-crystalline Form IV is characterized by an X-ray powder diffraction pattern comprising a peak at about 17.2±0.5 degrees 2θ.

In some embodiments, the co-crystalline Form IV is characterized by an X-ray powder diffraction pattern comprising a peak at about 18.1±0.5 degrees 2θ.

In some embodiments, the co-crystalline Form IV is characterized by an X-ray powder diffraction pattern comprising a peak at about 20.6±0.5 degrees 2θ.

In some embodiments, the co-crystalline Form IV is characterized by an X-ray powder diffraction pattern comprising a peak at about 22.5±0.5 degrees 2θ.

In some embodiments, the co-crystalline Form IV is characterized by an X-ray powder diffraction pattern comprising a peak at about 26.5±0.5 degrees 2θ.

In some embodiments, the co-crystalline Form IV is characterized by an X-ray powder diffraction pattern comprising a peak at about 31.3±0.5 degrees 2θ.

In some embodiments, the co-crystalline Form IV is characterized by an X-ray powder diffraction pattern comprising peaks at about 13.0±0.5 degrees 2θ and at about 20.6±0.5 degrees 2θ.

In some embodiments, the co-crystalline Form IV is characterized by an X-ray powder diffraction pattern comprising peaks at about 13.0±0.5 degrees 2θ and at about 22.5±0.5 degrees 2θ.

In some embodiments, the co-crystalline Form IV is characterized by an X-ray powder diffraction pattern comprising peaks at about 13.0±0.5 degrees 2θ and at about 26.5±0.5 degrees 2θ.

In some embodiments, the co-crystalline Form IV is characterized by an X-ray powder diffraction pattern comprising peaks at about 20.6±0.5 degrees 2θ and at about 26.5±0.5 degrees 2θ.

In some embodiments, the co-crystalline Form IV is characterized by an X-ray powder diffraction pattern comprising peaks at about 13.0±0.5 degrees 2θ, at about 20.6±0.5 degrees 2θ, and at about 26.5±0.5 degrees 2θ.

In some embodiments, the co-crystalline Form IV is characterized by an X-ray powder diffraction pattern comprising peaks at about 13.0±0.5 degrees 2θ, at about 22.5±0.5 degrees 2θ, and at about 26.5±0.5 degrees 2θ.

In some embodiments, the co-crystalline Form IV is characterized by an X-ray powder diffraction pattern comprising peaks at about 20.6±0.5 degrees 2θ, at about 22.5±0.5 degrees 2θ, and at about 26.5±0.5 degrees 2θ.

In some embodiments, the co-crystalline Form IV is characterized by an X-ray powder diffraction pattern comprising peaks at about 13.0±0.5 degrees 2θ, at about 20.6±0.5 degrees 2θ, and at about 22.5±0.5 degrees 2θ.

In some embodiments, the co-crystalline Form IV is characterized by an X-ray powder diffraction pattern comprising peaks at about 13.0±0.5 degrees 2θ, at about 20.6±0.5 degrees 2θ, at about 22.5±0.5 degrees 2θ, and at about 26.5±0.5 degrees 2θ.

In some embodiments, the co-crystalline Form IV is characterized by an X-ray powder diffraction pattern comprising peaks at about 13.0±0.5 degrees 2θ, at about 20.6±0.5 degrees 2θ, at about 22.5±0.5 degrees 2θ, at about 26.5±0.5 degrees 2θ, and at about 31.3±0.5 degrees 2θ.

In some embodiments, the co-crystalline Form IV is characterized by an X-ray powder diffraction pattern comprising peaks at about 13.0±0.5 degrees 2θ, at about 13.3±0.5 degrees 2θ, at about 17.2±0.5 degrees 2θ, at about 18.1±0.5 degrees 2θ, at about 20.6±0.5 degrees 2θ, at about 22.5±0.5 degrees 2θ, at about 26.5±0.5 degrees 2θ, and at about 31.3±0.5 degrees 2θ.

In some embodiments, the co-crystalline Form IV is characterized by an X-ray powder diffraction pattern comprising one or more peaks at about 7.6±0.5 degrees 2θ, at about 13.0±0.5 degrees 2θ, at about 13.3±0.5 degrees 2θ, at about 16.7±0.5 degrees 2θ, at about 17.2±0.5 degrees 2θ, at about 18.1±0.5 degrees 2θ, at about 19.7±0.5 degrees 2θ, at about 20.6±0.5 degrees 2θ, at about 21.4±0.5 degrees 2θ, at about 22.5±0.5 degrees 2θ, at about 26.5±0.5 degrees 2θ, and at about 31.3±0.5 degrees 2θ.

Figure 5:
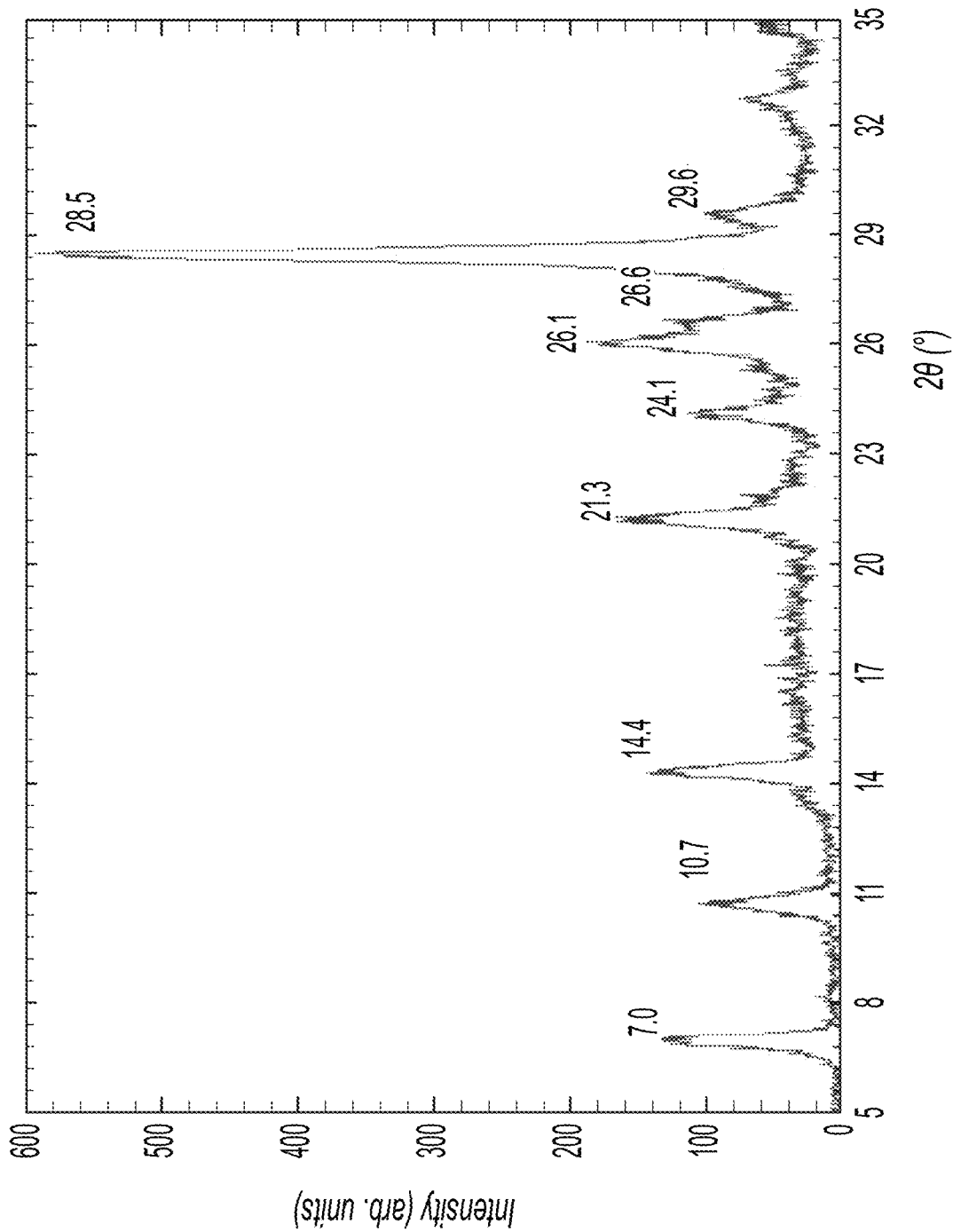
FIG. 5 shows X-ray powder diffraction pattern of the co-crystalline Form V of the compound of Formula I and ellagic acid.

In some embodiments, the co-crystalline Form V is characterized by an X-ray powder diffraction pattern substantially, as shown in FIG. 5. In some embodiments, the co-crystalline Form V is characterized by an X-ray powder diffraction pattern comprising one or more peaks, as provided in Table 8. In some embodiments, the co-crystalline Form V is characterized by an X-ray powder diffraction pattern comprising substantially all of, or all of, the peaks as provided in Table 8.

In some embodiments, the co-crystalline Form V is characterized by an X-ray powder diffraction pattern comprising a peak at about 7.0±0.5 degrees 2θ.

In some embodiments, the co-crystalline Form V is characterized by an X-ray powder diffraction pattern comprising a peak at about 10.7±0.5 degrees 2θ.

In some embodiments, the co-crystalline Form V is characterized by an X-ray powder diffraction pattern comprising a peak at about 14.4±0.5 degrees 2θ.

In some embodiments, the co-crystalline Form V is characterized by an X-ray powder diffraction pattern comprising a peak at about 21.3±0.5 degrees 2θ.

In some embodiments, the co-crystalline Form V is characterized by an X-ray powder diffraction pattern comprising a peak at about 24.1±0.5 degrees 2θ.

In some embodiments, the co-crystalline Form V is characterized by an X-ray powder diffraction pattern comprising a peak at about 26.1±0.5 degrees 2θ.

In some embodiments, the co-crystalline Form V is characterized by an X-ray powder diffraction pattern comprising a peak at about 26.6±0.5 degrees 2θ.

In some embodiments, the co-crystalline Form V is characterized by an X-ray powder diffraction pattern comprising a peak at about 28.5±0.5 degrees 2θ.

In some embodiments, the co-crystalline Form V is characterized by an X-ray powder diffraction pattern comprising a peak and at about 29.6±0.5 degrees 2θ.

In some embodiments, the co-crystalline Form V is characterized by an X-ray powder diffraction pattern comprising peaks at about 7.0±0.5 degrees 2θ and at about 14.4±0.5 degrees 2θ.

In some embodiments, the co-crystalline Form V is characterized by an X-ray powder diffraction pattern comprising peaks at about 7.0±0.5 degrees 2θ and at about 21.3±0.5 degrees 2θ.

In some embodiments, the co-crystalline Form V is characterized by an X-ray powder diffraction pattern comprising peaks at about 7.0±0.5 degrees 2θ and at about 26.1±0.5 degrees 2θ.

In some embodiments, the co-crystalline Form V is characterized by an X-ray powder diffraction pattern comprising peaks at about 7.0±0.5 degrees 2θ and at about 28.5±0.5 degrees 2θ.

In some embodiments, the co-crystalline Form V is characterized by an X-ray powder diffraction pattern comprising peaks at about 7.0±0.5 degrees 2θ, at about 14.4±0.5 degrees 2θ, at about 21.3±0.5 degrees 2θ, at about 26.1±0.5 degrees 2θ, and at about 28.5±0.5 degrees 2θ.

In some embodiments, the co-crystalline Form V is characterized by an X-ray powder diffraction pattern comprising peaks at about 14.4±0.5 degrees 2θ and at about 21.3±0.5 degrees 2θ.

In some embodiments, the co-crystalline Form V is characterized by an X-ray powder diffraction pattern comprising peaks at about 14.4±0.5 degrees 2θ and at about 26.1±0.5 degrees 2θ.

In some embodiments, the co-crystalline Form V is characterized by an X-ray powder diffraction pattern comprising at about 14.4±0.5 degrees 2θ and at about 28.5±0.5 degrees 2θ.

In some embodiments, the co-crystalline Form V is characterized by an X-ray powder diffraction pattern comprising peaks at about 21.3±0.5 degrees 2θ and at about 26.1±0.5 degrees 2θ, and at about 28.5±0.5 degrees 2θ.

In some embodiments, the co-crystalline Form V is characterized by an X-ray powder diffraction pattern comprising peaks at about 21.3±0.5 degrees 2θ and at about 28.5±0.5 degrees 2θ.

In some embodiments, the co-crystalline Form V is characterized by an X-ray powder diffraction pattern comprising peaks at about 26.1±0.5 degrees 2θ and at about 28.5±0.5 degrees 2θ.

In some embodiments, the co-crystalline Form V is characterized by an X-ray powder diffraction pattern comprising peaks at about 7.0±0.5 degrees 2θ, at about 10.7±0.5 degrees 2θ, at about 14.4±0.5 degrees 2θ, at about 21.3±0.5 degrees 2θ, at about 26.1±0.5 degrees 2θ, and at about 28.5±0.5 degrees 2θ.

In some embodiments, the co-crystalline Form V is characterized by an X-ray powder diffraction pattern comprising peaks at about 7.0±0.5 degrees 2θ, at about 10.7±0.5 degrees 2θ, at about 14.4±0.5 degrees 2θ, at about 21.3±0.5 degrees 2θ, at about 24.1±0.5 degrees 2θ, at about 26.1±0.5 degrees 2θ, and at about 28.5±0.5 degrees 2θ.

In some embodiments, the co-crystalline Form V is characterized by an X-ray powder diffraction pattern comprising one or more peaks at about 7.0±0.5 degrees 2θ, at about 10.7±0.5 degrees 2θ, at about 14.4±0.5 degrees 2θ, at about 21.3±0.5 degrees 2θ, at about 24.1±0.5 degrees 2θ, at about 26.1±0.5 degrees 2θ, at about 26.6±0.5 degrees 2θ, at about 28.5±0.5 degrees 2θ, and at about 29.6±0.5 degrees 2θ.

Figure 6:
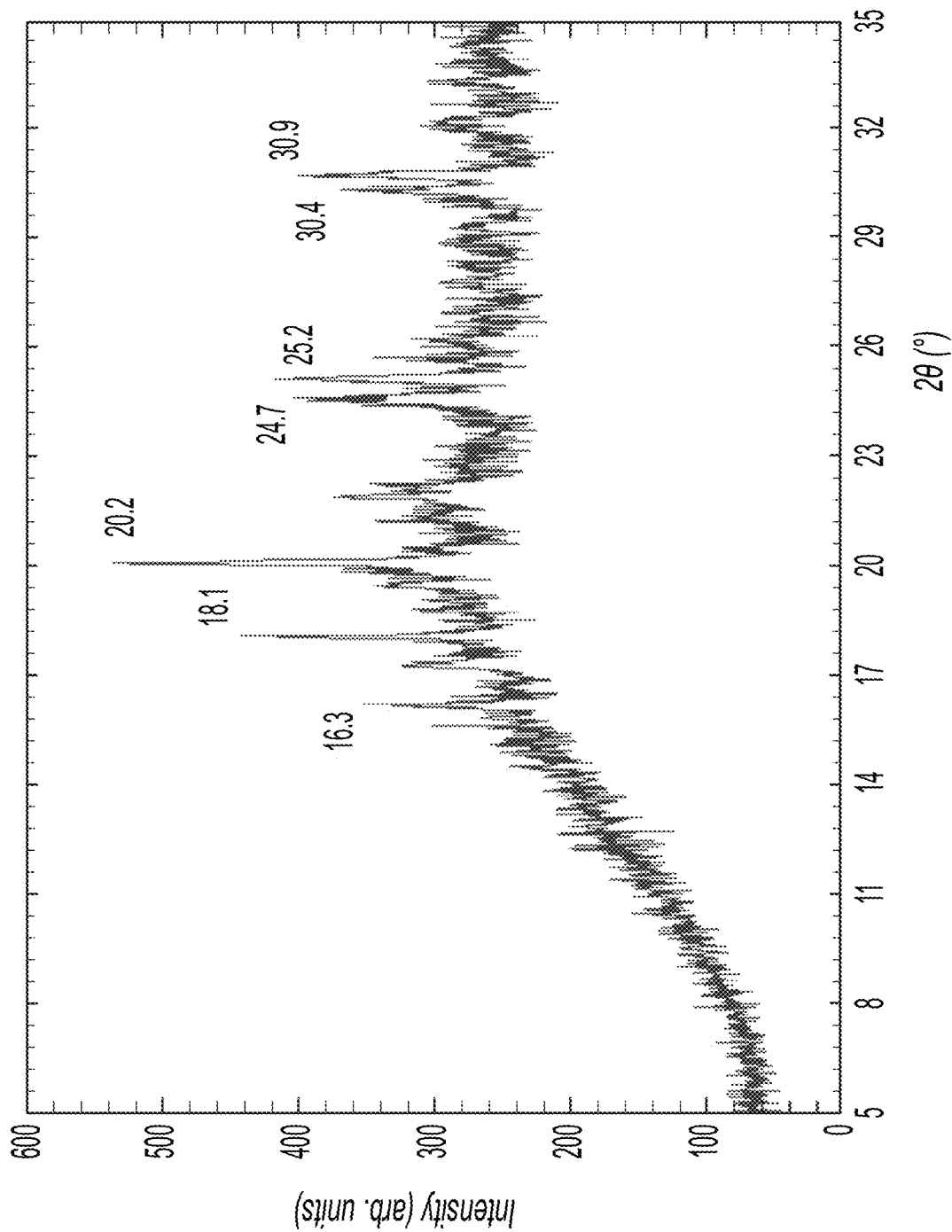
FIG. 6 shows X-ray powder diffraction pattern of the co-crystalline Form VI of the compound of Formula I and $MgCl_2$.

In some embodiments, the co-crystalline Form VI is characterized by an X-ray powder diffraction pattern substantially, as shown in FIG. 6. In some embodiments, the co-crystalline Form VI is characterized by an X-ray powder diffraction pattern comprising one or more peaks, as provided in Table 9. In some embodiments, the co-crystalline Form VI is characterized by an X-ray powder diffraction pattern comprising substantially all of, or all of, the peaks as provided in Table 9.

In some embodiments, the co-crystalline Form VI is characterized by an X-ray powder diffraction pattern comprising a peak at about 16.3±0.5 degrees 2θ.

In some embodiments, the co-crystalline Form VI is characterized by an X-ray powder diffraction pattern comprising a peak at about 18.1±0.5 degrees 2θ.

In some embodiments, the co-crystalline Form VI is characterized by an X-ray powder diffraction pattern comprising a peak at about 20.2±0.5 degrees 2θ.

In some embodiments, the co-crystalline Form VI is characterized by an X-ray powder diffraction pattern comprising a peak at about 24.7±0.5 degrees 2θ.

In some embodiments, the co-crystalline Form VI is characterized by an X-ray powder diffraction pattern comprising a peak at about 25.2±0.5 degrees 2θ.

In some embodiments, the co-crystalline Form VI is characterized by an X-ray powder diffraction pattern comprising a peak at about 30.4±0.5 degrees 2θ.

In some embodiments, the co-crystalline Form VI is characterized by an X-ray powder diffraction pattern comprising a peak at about 30.9±0.5 degrees 2θ.

In some embodiments, the co-crystalline Form VI is characterized by an X-ray powder diffraction pattern comprising peaks at about 18.1±0.5 degrees 2θ and at about 20.2±0.5 degrees 2θ.

In some embodiments and the co-crystalline Form VI is characterized by an X-ray powder diffraction pattern comprising peaks at about 18.1±0.5 degrees 2θ and at about 25.2±0.5 degrees 2θ.

In some embodiments and the co-crystalline Form VI is characterized by an X-ray powder diffraction pattern comprising peaks at about 18.1±0.5 degrees 2θ and at about 30.9±0.5 degrees 2θ.

In some embodiments and the co-crystalline Form VI is characterized by an X-ray powder diffraction pattern comprising peaks at about 20.2±0.5 degrees 2θ and at about 25.2±0.5 degrees 2θ.

In some embodiments and the co-crystalline Form VI is characterized by an X-ray powder diffraction pattern comprising peaks at about 20.2±0.5 degrees 2θ and at about 30.9±0.5 degrees 2θ.

In some embodiments and the co-crystalline Form VI is characterized by an X-ray powder diffraction pattern comprising peaks at about 25.2±0.5 degrees 2θ and at about 30.9±0.5 degrees 2θ.

In some embodiments, the co-crystalline Form VI is characterized by an X-ray powder diffraction pattern comprising one or more peaks at about 18.1±0.5 degrees 2θ, at about 25.2±0.5 degrees 2θ, and at about 30.9±0.5 degrees 2θ.

In some embodiments, the co-crystalline Form VI is characterized by an X-ray powder diffraction pattern comprising one or more peaks at about 18.1±0.5 degrees 2θ, at about 20.2±0.5 degrees 2θ, and at about 30.9±0.5 degrees 2θ.

In some embodiments, the co-crystalline Form VI is characterized by an X-ray powder diffraction pattern comprising one or more peaks at about 20.2±0.5 degrees 2θ, at about 25.2±0.5 degrees 2θ, and at about 30.9±0.5 degrees 2θ.

In some embodiments, the co-crystalline Form VI is characterized by an X-ray powder diffraction pattern comprising one or more peaks at about 18.1±0.5 degrees 2θ, at about 20.2±0.5 degrees 2θ, and at about 25.2±0.5 degrees 2θ.

In some embodiments, the co-crystalline Form VI is characterized by an X-ray powder diffraction pattern comprising one or more peaks at about 18.1±0.5 degrees 2θ, at about 20.2±0.5 degrees 2θ, at about 25.2±0.5 degrees 2θ, and at about 30.9±0.5 degrees 2θ.

In some embodiments, the co-crystalline Form VI is characterized by an X-ray powder diffraction pattern comprising one or more peaks at about 18.1±0.5 degrees 2θ, at about 20.2±0.5 degrees 2θ, at about 24.7±0.5 degrees 2θ, at about 25.2±0.5 degrees 2θ, at about 30.4±0.5 degrees 2θ, and at about 30.9±0.5 degrees 2θ.

In some embodiments, the co-crystalline Form VI is characterized by an X-ray powder diffraction pattern comprising one or more peaks at about 16.3±0.5 degrees 2θ, at about 18.1±0.5 degrees 2θ, at about 20.2±0.5 degrees 2θ, at about 24.7±0.5 degrees 2θ, at about 25.2±0.5 degrees 2θ, at about 30.4±0.5 degrees 2θ, and at about 30.9±0.5 degrees 2θ.

Figure 7:
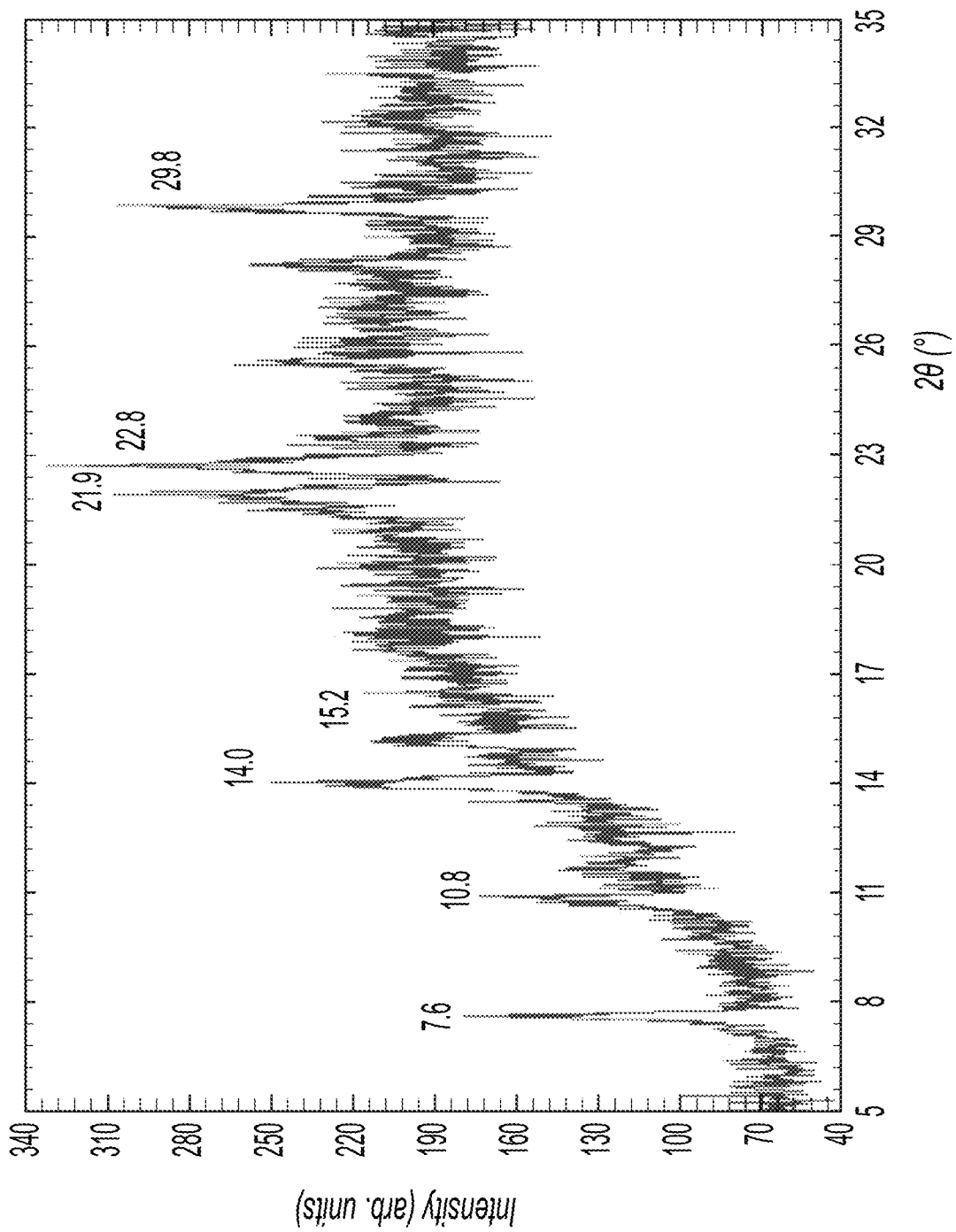
FIG. 7 shows X-ray powder diffraction pattern of the co-crystalline Form VII of the compound of Formula I and $CaCl_2$.

In some embodiments, the co-crystalline Form VII is characterized by an X-ray powder diffraction pattern substantially, as shown in FIG. 7. In some embodiments, the co-crystalline Form VII is characterized by an X-ray powder diffraction pattern comprising one or more peaks, as provided in Table 10. In some embodiments, the co-crystalline Form VII is characterized by an X-ray powder diffraction pattern comprising substantially all of, or all of, the peaks as provided in Table 10.

In some embodiments, the co-crystalline Form VII is characterized by an X-ray powder diffraction pattern comprising a peak at about 7.6±0.5 degrees 2θ.

In some embodiments, the co-crystalline Form VII is characterized by an X-ray powder diffraction pattern comprising a peak at about 10.8±0.5 degrees 2θ.

In some embodiments, the co-crystalline Form VII is characterized by an X-ray powder diffraction pattern comprising a peak at about 14.0±0.5 degrees 2θ.

In some embodiments, the co-crystalline Form VII is characterized by an X-ray powder diffraction pattern comprising a peak at about 15.2±0.5 degrees 2θ.

In some embodiments, the co-crystalline Form VII is characterized by an X-ray powder diffraction pattern comprising a peak at about 21.9±0.5 degrees 2θ.

In some embodiments, the co-crystalline Form VII is characterized by an X-ray powder diffraction pattern comprising a peak at about 22.8±0.5 degrees 2θ.

In some embodiments, the co-crystalline Form VII is characterized by an X-ray powder diffraction pattern comprising a peak at about 29.8±0.5 degrees 2θ.

In some embodiments, the co-crystalline Form VII is characterized by an X-ray powder diffraction pattern comprising peaks at about 7.6±0.5 degrees 2θ, at about 14.0±0.5 degrees 2θ, at about 21.9±0.5 degrees 2θ, at about 22.8±0.5 degrees 2θ, and at about 29.8±0.5 degrees 2θ.

In some embodiments and the co-crystalline Form VII is characterized by an X-ray powder diffraction pattern comprising peaks at about 7.6±0.5 degrees 2θ and at about 14.0±0.5 degrees 2θ.

In some embodiments and the co-crystalline Form VII is characterized by an X-ray powder diffraction pattern comprising peaks at about 7.6±0.5 degrees 2θ and at about 21.9±0.5 degrees 2θ.

In some embodiments and the co-crystalline Form VII is characterized by an X-ray powder diffraction pattern comprising peaks at about 7.6±0.5 degrees 2θ and at about 22.8±0.5 degrees 2θ.

In some embodiments and the co-crystalline Form VII is characterized by an X-ray powder diffraction pattern comprising peaks at about 7.6±0.5 degrees 2θ and at about 29.8±0.5 degrees 2θ.

In some embodiments and the co-crystalline Form VII is characterized by an X-ray powder diffraction pattern comprising peaks at about 14.0±0.5 degrees 2θ and at about 21.9±0.5 degrees 2θ.

In some embodiments and the co-crystalline Form VII is characterized by an X-ray powder diffraction pattern comprising peaks at about 14.0±0.5 degrees 2θ and at about 22.8±0.5 degrees 2θ.

In some embodiments and the co-crystalline Form VII is characterized by an X-ray powder diffraction pattern comprising peaks at about 14.0±0.5 degrees 2θ and at about 29.8±0.5 degrees 2θ.

In some embodiments and the co-crystalline Form VII is characterized by an X-ray powder diffraction pattern comprising peaks at about 21.9±0.5 degrees 2θ and at about 22.8±0.5 degrees 2θ.

In some embodiments and the co-crystalline Form VII is characterized by an X-ray powder diffraction pattern comprising peaks at about 21.9±0.5 degrees 2θ and at about 29.8±0.5 degrees 2θ.

In some embodiments, the co-crystalline Form VII is characterized by an X-ray powder diffraction pattern comprising peaks at about 22.8±0.5 degrees 2θ and at about 29.8±0.5 degrees 2θ.

In some embodiments, the co-crystalline Form VII is characterized by an X-ray powder diffraction pattern comprising peaks at about 7.6±0.5 degrees 2θ, at about 21.9±0.5 degrees 2θ, at about 22.8±0.5 degrees 2θ, and at about 29.8±0.5 degrees 2θ.

In some embodiments, the co-crystalline Form VII is characterized by an X-ray powder diffraction pattern comprising peaks at about 7.6±0.5 degrees 2θ, at about 14.0±0.5 degrees 2θ, at about 22.8±0.5 degrees 2θ, and at about 29.8±0.5 degrees 2θ.

In some embodiments, the co-crystalline Form VII is characterized by an X-ray powder diffraction pattern comprising peaks at about 7.6±0.5 degrees 2θ, at about 14.0±0.5 degrees 2θ, at about 21.9±0.5 degrees 2θ, and at about 29.8±0.5 degrees 2θ.

In some embodiments, the co-crystalline Form VII is characterized by an X-ray powder diffraction pattern comprising peaks at about 7.6±0.5 degrees 2θ, at about 14.0±0.5 degrees 2θ, at about 21.9±0.5 degrees 2θ, and at about 22.8±0.5 degrees 2θ.

In some embodiments, the co-crystalline Form VII is characterized by an X-ray powder diffraction pattern comprising peaks at about 14.0±0.5 degrees 2θ, at about 21.9±0.5 degrees 2θ, at about 22.8±0.5 degrees 2θ, and at about 29.8±0.5 degrees 2θ.

In some embodiments, the co-crystalline Form VII is characterized by an X-ray powder diffraction pattern comprising peaks at about 7.6±0.5 degrees 2θ, at about 14.0±0.5 degrees 2θ, at about 21.9±0.5 degrees 2θ, at about 22.8±0.5 degrees 2θ, and at about 29.8±0.5 degrees 2θ.

In some embodiments, the co-crystalline Form VII is characterized by an X-ray powder diffraction pattern comprising one or more peaks at about 7.6±0.5 degrees 2θ, at about 10.8±0.5 degrees 2θ, at about 14.0±0.5 degrees 2θ, at about 15.2±0.5 degrees 2θ, at about 21.9±0.5 degrees 2θ, at about 22.8±0.5 degrees 2θ, and at about 29.8±0.5 degrees 2θ.

In some embodiments, co-crystalline forms of the compound of any one of the Formulae, as described or provided for herein, such as Formula IV-I, Formula IV-I-a, or Formula IV-I-b with a coformer are provided. In some embodiments, co-crystalline forms of the compound of Formula IV-I, Formula IV-Ia, or Formula IV-Ib with a coformer are provided. In some embodiments, co-crystalline forms of the compound of Formula IV-I with a coformer are provided. In some embodiments, co-crystalline forms of the compound of Formula IV-Ia with a coformer are provided. In some embodiments, co-crystalline forms of the compound of Formula IV-Ib with a coformer are provided. In some embodiments, the coformer is a coformer provided and described herein. In some embodiments, the coformer is trifluorotriiodobenzene, 4-aminobenzoic acid, L-aspartic acid, paracetamol, ellagic acid, 2-aminobenzoic acid, or urea, or any combination thereof. In some embodiments, the coformer is trifluorotriiodobenzene. In some embodiments, the coformer is 4-aminobenzoic acid. In some embodiments, the coformer is L-aspartic acid. In some embodiments, the coformer is paracetamol. In some embodiments, the coformer is ellagic acid, 2-aminobenzoic acid. In some embodiments, the coformer is or urea.

In some embodiments, the present embodiments provide methods of crystallizing the compound of any one of the Formulae, as described or provided for herein, such as Formula IV, Formula IV-I, Formula IV-Ia, and Formula IV-Ib, without a coformer.

In some embodiments, crystalline forms of the compound of any one of the Formulae, as described or provided for herein, such as Formula IV, Formula IV-I, Formula IV-Ia, and Formula IV-Ib, without a coformer are provided. In some embodiments, crystalline forms of the compound of Formula IV, as described or provided for herein, without a coformer are provided. In some embodiments, crystalline forms of the compound of Formula IV, Formula IV-I, Formula IV-Ia, and Formula IV-Ib, as described or provided for herein, such as, without a coformer are provided.

In some embodiments, the crystalline Form VIII of the compound of Formula IV-I, Formula IV-Ia, and Formula IV-Ib (hereinafter the "crystalline Form VIII") is provided.

Figure 26:
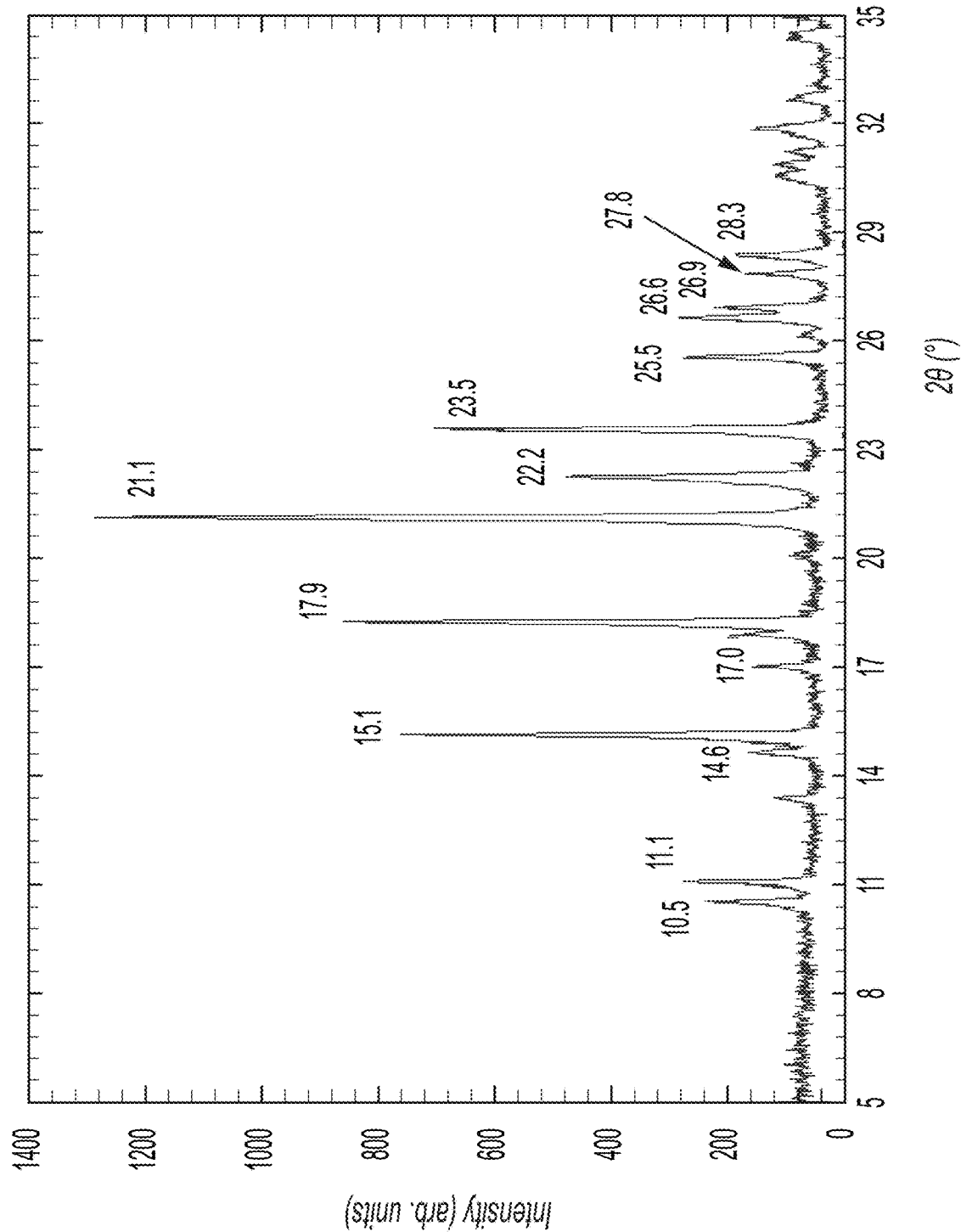
FIG. 26 shows X-ray powder diffraction pattern of the crystalline Form VIII of the compound of Formula IV-I.

In some embodiments, the crystalline Form VIII is characterized by an X-ray powder diffraction pattern substantially, as shown in FIG. 26. In some embodiments, the crystalline Form VIII is characterized by an X-ray powder diffraction pattern comprising one or more peaks, as provided in Table 11.

In some embodiments, the crystalline Form VIII is characterized by an X-ray powder diffraction pattern comprising a peak at about 10.5±0.5 degrees 2θ.

In some embodiments, the crystalline Form VIII is characterized by an X-ray powder diffraction pattern comprising a peak at about 11.1±0.5 degrees 2θ.

In some embodiments, the crystalline Form VIII is characterized by an X-ray powder diffraction pattern comprising a peak at about 14.6±0.5 degrees 2θ.

In some embodiments, the crystalline Form VIII is characterized by an X-ray powder diffraction pattern comprising a peak at about 15.1±0.5 degrees 2θ.

In some embodiments, the crystalline Form VIII is characterized by an X-ray powder diffraction pattern comprising a peak at about 17.0±0.5 degrees 2θ.

In some embodiments, the crystalline Form VIII is characterized by an X-ray powder diffraction pattern comprising a peak at about 17.9±0.5 degrees 2θ.

In some embodiments, the crystalline Form VIII is characterized by an X-ray powder diffraction pattern comprising a peak at about 18.2±0.5 degrees 2θ.

In some embodiments, the crystalline Form VIII is characterized by an X-ray powder diffraction pattern comprising a peak at about 21.1±0.5 degrees 2θ.

In some embodiments, the crystalline Form VIII is characterized by an X-ray powder diffraction pattern comprising a peak at about 22.2±0.5 degrees 2θ.

In some embodiments, the crystalline Form VIII is characterized by an X-ray powder diffraction pattern comprising a peak at about 23.5±0.5 degrees 2θ.

In some embodiments, the crystalline Form VIII is characterized by an X-ray powder diffraction pattern comprising a peak at about 25.5±0.5 degrees 2θ.

In some embodiments, the crystalline Form VIII is characterized by an X-ray powder diffraction pattern comprising a peak at about 26.6±0.5 degrees 2θ.

In some embodiments, the crystalline Form VIII is characterized by an X-ray powder diffraction pattern comprising a peak at about 26.9±0.5 degrees 2θ.

In some embodiments, the crystalline Form Viii is characterized by an X-ray powder diffraction pattern comprising a peak at about 27.8±0.5 degrees 2θ.

In some embodiments, the crystalline Form VIII is characterized by an X-ray powder diffraction pattern comprising a peak at about 28.3±0.5 degrees 2θ.

In some embodiments, the crystalline Form VIII is characterized by an X-ray powder diffraction pattern comprising peaks at about 15.1±0.5 degrees 2θ and at about 17.9±0.5 degrees 2θ.

In some embodiments, the crystalline Form VIII is characterized by an X-ray powder diffraction pattern comprising peaks at about 15.1±0.5 degrees 2θ and at about 17.9±0.5 degrees 2θ.

In some embodiments, the crystalline Form VIII is characterized by an X-ray powder diffraction pattern comprising peaks at about 15.1±0.5 degrees 2θ and at about 21.1±0.5 degrees 2θ.

In some embodiments, the crystalline Form VIII is characterized by an X-ray powder diffraction pattern comprising peaks at about 15.1±0.5 degrees 2θ and at about 23.5±0.5 degrees 2θ.

In some embodiments, the crystalline Form VIII is characterized by an X-ray powder diffraction pattern comprising peaks at about 17.9±0.5 degrees 2θ and at about 21.1±0.5 degrees 2θ.

In some embodiments, the crystalline Form VIII is characterized by an X-ray powder diffraction pattern comprising peaks at about 17.9±0.5 degrees 2θ, and at about 23.5±0.5 degrees 2θ

In some embodiments, the crystalline Form VIII is characterized by an X-ray powder diffraction pattern comprising peaks at about 21.1±0.5 degrees 2θ and at about 23.5±0.5 degrees 2θ.

In some embodiments, the crystalline Form VIII is characterized by an X-ray powder diffraction pattern comprising peaks at about 15.1±0.5 degrees 2θ, at about 21.1±0.5 degrees 2θ, and at about 23.5±0.5 degrees 2θ.

In some embodiments, the crystalline Form VIII is characterized by an X-ray powder diffraction pattern comprising peaks at about 15.1±0.5 degrees 2θ, at about 17.9±0.5 degrees 2θ, and at about 23.5±0.5 degrees 2θ.

In some embodiments, the crystalline Form VIII is characterized by an X-ray powder diffraction pattern comprising peaks at about 17.9±0.5 degrees 2θ, at about 21.1±0.5 degrees 2θ, and at about 23.5±0.5 degrees 2θ.

In some embodiments, the crystalline Form VIII is characterized by an X-ray powder diffraction pattern comprising peaks at about 15.1±0.5 degrees 2θ, at about 17.9±0.5 degrees 2θ, and at about 21.1±0.5 degrees 2θ.

In some embodiments, the crystalline Form VIII is characterized by an X-ray powder diffraction pattern comprising peaks at about 15.1±0.5 degrees 2θ, at about 17.9±0.5 degrees 2θ, at about 21.1±0.5 degrees 2θ, and at about 23.5±0.5 degrees 2θ.

In some embodiments, the crystalline Form VIII is characterized by an X-ray powder diffraction pattern comprising peaks at about 15.1±0.5 degrees 2θ, at about 17.9±0.5 degrees 2θ, at about 21.1±0.5 degrees 2θ, at about 22.2±0.5 degrees 2θ, and at about 23.5±0.5 degrees 2θ.

In some embodiments, the crystalline Form VIII is characterized by an X-ray powder diffraction pattern comprising one or more at about 15.1±0.5 degrees 2θ, at about 17.9±0.5 degrees 2θ, at about 21.1±0.5 degrees 2θ, at about 22.2±0.5 degrees 2θ, at about 23.5±0.5 degrees 2θ, at about 25.5±0.5 degrees 2θ, at about 26.6±0.5 degrees 2θ, and at about 26.9±0.5 degrees 2θ.

In some embodiments, the crystalline Form VIII is characterized by an X-ray powder diffraction pattern comprising one or more peaks at about 10.5±0.5 degrees 2θ, at about 11.1±0.5 degrees 2θ, at about 15.1±0.5 degrees 2θ, at about 17.9±0.5 degrees 2θ, at about 21.1±0.5 degrees 2θ, at about 22.2±0.5 degrees 2θ, at about 23.5±0.5 degrees 2θ, at about 25.5±0.5 degrees 2θ, at about 26.6±0.5 degrees 2θ, at about 26.9±0.5 degrees 2θ, at about 27.8±0.5 degrees 2θ, and at about 28.3±0.5 degrees 2θ.

In some embodiments, the crystalline Form VIII is characterized by an X-ray powder diffraction pattern comprising one or more peaks at about 10.5±0.5 degrees 2θ, at about 11.1±0.5 degrees 2θ, at about 14.6±0.5 degrees 2θ, at about 15.1±0.5 degrees 2θ, at about 17.0±0.5 degrees 2θ, at about 17.9±0.5 degrees 2θ, at about 18.2±0.5 degrees 2θ, at about 21.1±0.5 degrees 2θ, at about 22.2±0.5 degrees 2θ, at about 23.5±0.5 degrees 2θ, at about 25.5±0.5 degrees 2θ, at about 26.6±0.5 degrees 2θ, at about 26.9±0.5 degrees 2θ, at about 27.8±0.5 degrees 2θ, and at about 28.3±0.5 degrees 2θ.

As used herein, unless otherwise indicated, the phrase "one or more peaks" should be understood to be inclusive of (i) crystalline and co-crystalline forms that have XRD peaks at every peak value recited after this phrase. (ii) crystalline and co-crystalline forms that have an XRD peak at only one of the peak values recited after this phrase, as well as (iii) crystalline and co-crystalline forms that have XRD peaks at two or more (e.g., three or more, four or more, five or more, six or more, or even seven or more) of the peak values recited after this phrase.

Figure 16:
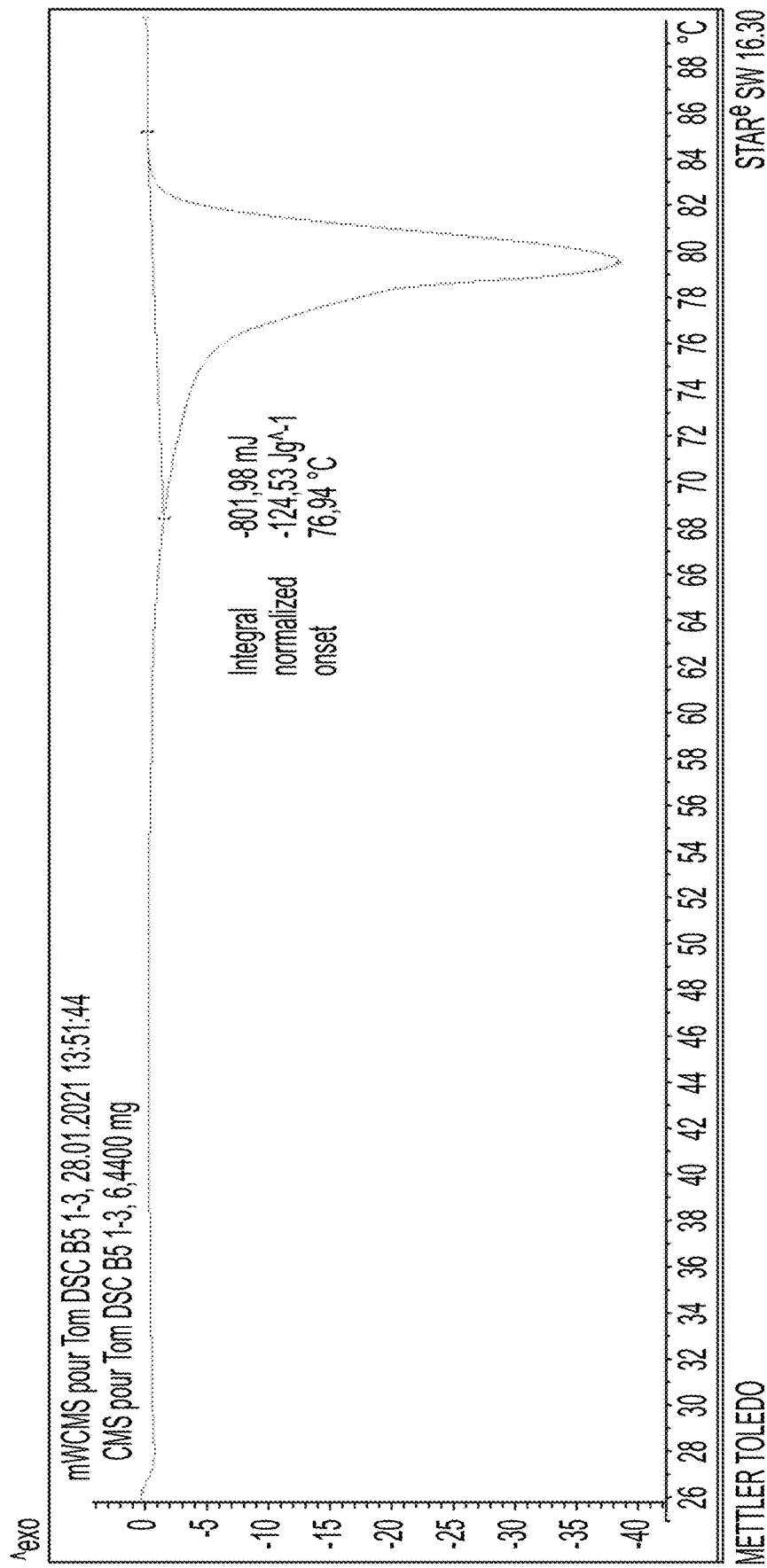
FIG. 16 shows a Differential Scanning Calorimetry (DSC) thermogram of the co-crystalline Form I.
Figure 21:
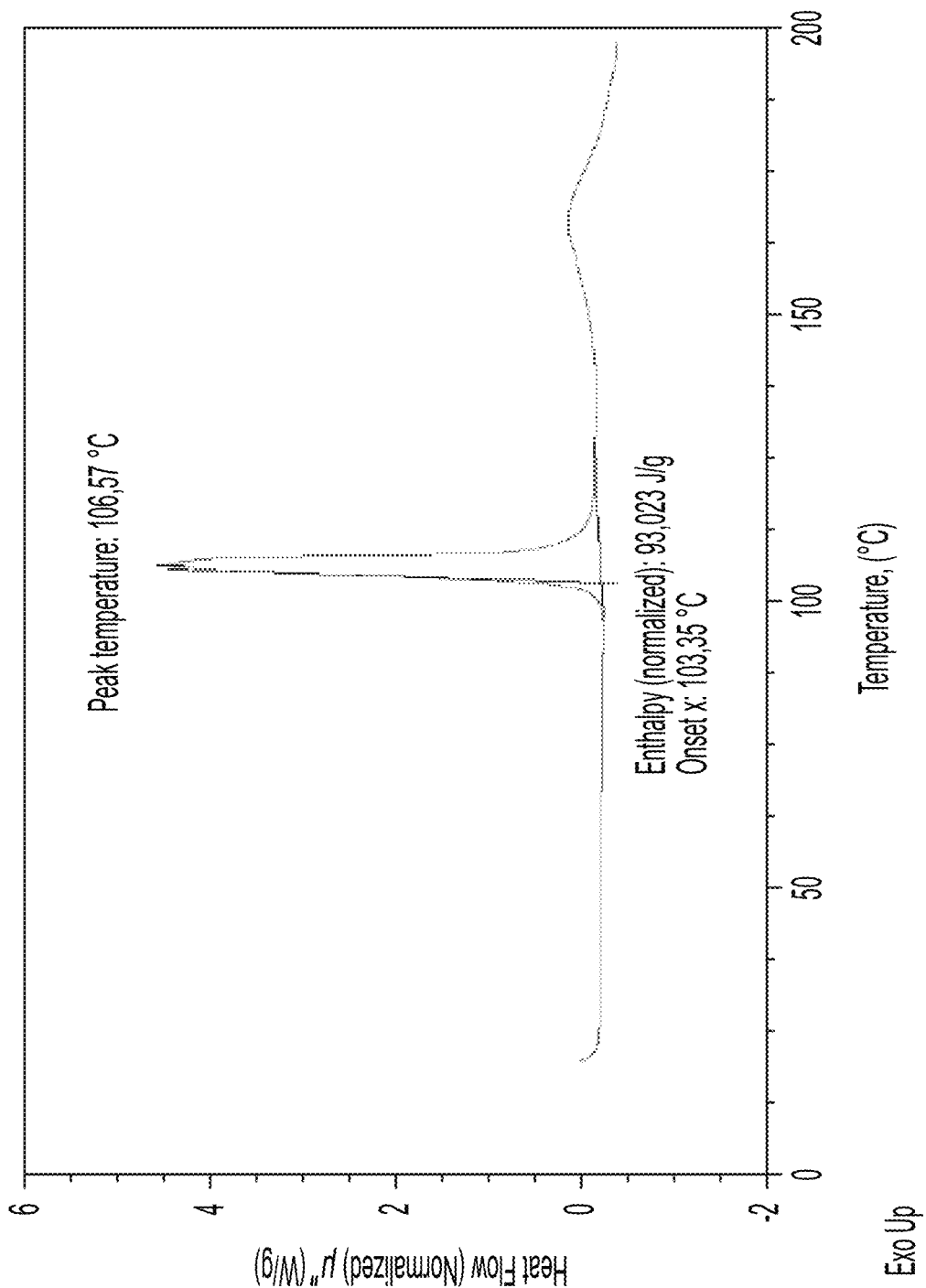
FIG. 21 shows a Differential Scanning Calorimetry (DSC) thermogram of the co-crystalline Form II.
Figure 23:
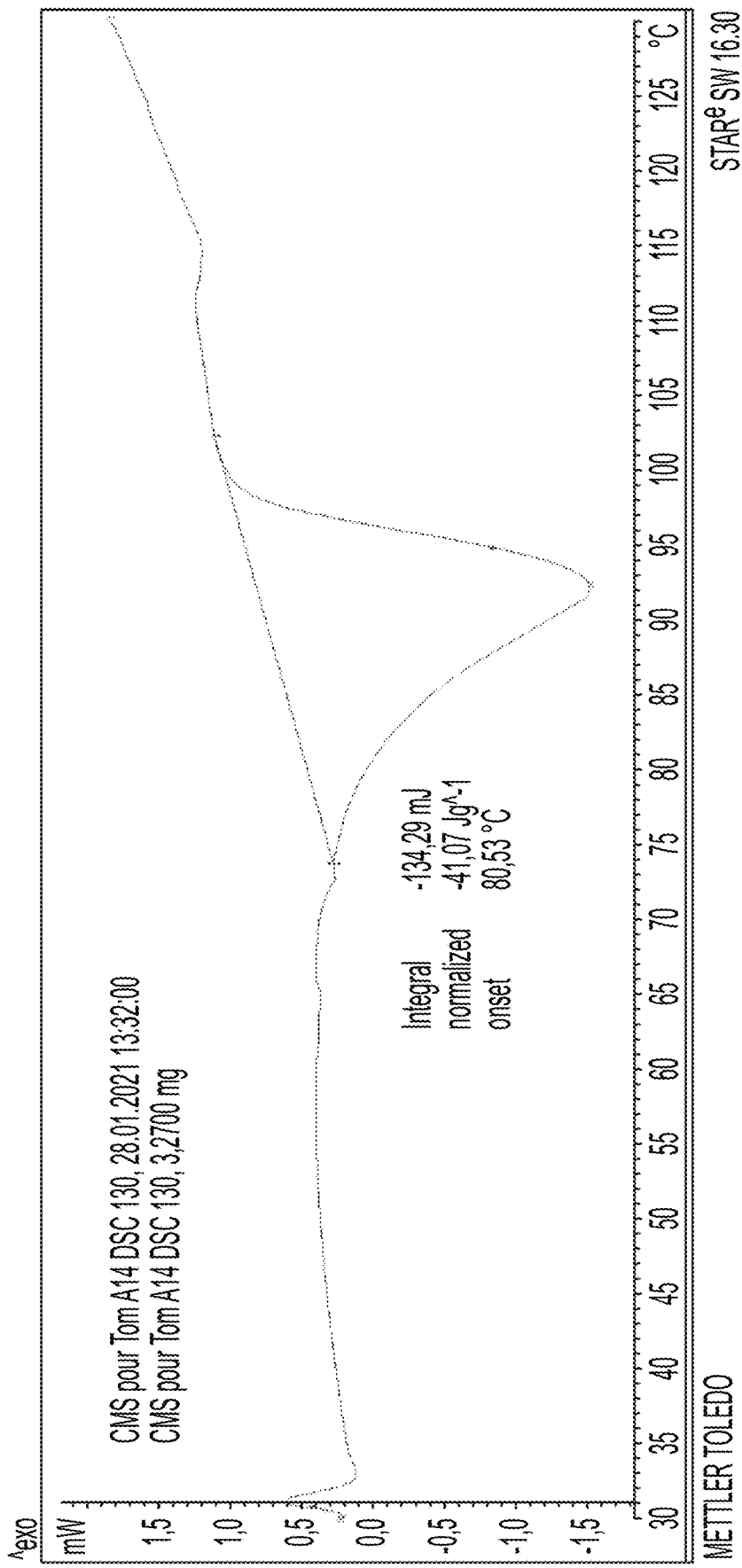
FIG. 23 shows a Differential Scanning Calorimetry (DSC) thermogram of the co-crystalline Form III.

In some embodiments, the co-crystalline Forms I-VII are characterized by a DSC thermogram. For example, the co-crystalline Form I to Form III are characterized by a DSC thermogram as shown in FIGS. 16, 21, and 23 respectively.

In some embodiments, the co-crystalline Forms I-VII and the crystalline Form VIII are characterized by any combination of the above data.

In some embodiments, the X-ray powder diffraction peaks recited herein for particular embodiments can vary by ±0.4 degrees 2θ, by ±0.3 degrees 2θ, by ±0.2 degrees 2θ, or by ±0.1 degrees 2θ.

In some embodiments, the co-crystalline Form I is characterized by an X-ray powder diffraction pattern comprising a d-spacing value substantially as shown in Table 4.

In some embodiments, the co-crystalline Form I characterized by an X-ray powder diffraction pattern comprising a d-spacing value at about 9.8±0.5 degrees angstroms.

In some embodiments, the co-crystalline Form I characterized by an X-ray powder diffraction pattern comprising a d-spacing value at about 7.6±0.5 degrees angstroms.

In some embodiments, the co-crystalline Form I characterized by an X-ray powder diffraction pattern comprising a d-spacing value at about 5.9±0.5 degrees angstroms.

In some embodiments, the co-crystalline Form I characterized by an X-ray powder diffraction pattern comprising a d-spacing value at about 5.2±0.5 degrees angstroms.

In some embodiments, the co-crystalline Form I characterized by an X-ray powder diffraction pattern comprising a d-spacing value at about 5.1±0.5 degrees angstroms.

In some embodiments, the co-crystalline Form I characterized by an X-ray powder diffraction pattern comprising a d-spacing value at about 5.0±0.5 degrees angstroms.

In some embodiments, the co-crystalline Form I characterized by an X-ray powder diffraction pattern comprising a d-spacing value at about 4.9±0.5 degrees angstroms.

In some embodiments, the co-crystalline Form I characterized by an X-ray powder diffraction pattern comprising a d-spacing value at about 4.8±0.5 degrees angstroms.

In some embodiments, the co-crystalline Form I characterized by an X-ray powder diffraction pattern comprising a d-spacing value at about 4.2±0.5 degrees angstroms.

In some embodiments, the co-crystalline Form I characterized by an X-ray powder diffraction pattern comprising a d-spacing value at about 4.1±0.5 degrees angstroms.

In some embodiments, the co-crystalline Form I characterized by an X-ray powder diffraction pattern comprising a d-spacing value at about 4.1±0.5 degrees angstroms.

In some embodiments, the co-crystalline Form I characterized by an X-ray powder diffraction pattern comprising a d-spacing value at about 3.8±0.5 degrees angstroms.

In some embodiments, the co-crystalline Form I characterized by an X-ray powder diffraction pattern comprising a d-spacing value at about 3.6±0.5 degrees angstroms.

In some embodiments, the co-crystalline Form I characterized by an X-ray powder diffraction pattern comprising a d-spacing value at about 3.6±0.5 degrees angstroms.

In some embodiments, the co-crystalline Form I characterized by an X-ray powder diffraction pattern comprising a d-spacing value at about 3.5±0.5 degrees angstroms.

In some embodiments, the co-crystalline Form I characterized by an X-ray powder diffraction pattern comprising a d-spacing value at about 3.4±0.5 degrees angstroms.

In some embodiments, the co-crystalline Form I characterized by an X-ray powder diffraction pattern comprising a d-spacing value at about 3.4±0.5 degrees angstroms.

In some embodiments, the co-crystalline Form I characterized by an X-ray powder diffraction pattern comprising a d-spacing value at about 3.2±0.5 degrees angstroms.

In some embodiments, the co-crystalline Form I characterized by an X-ray powder diffraction pattern comprising a d-spacing value at about 3.2±0.5 degrees angstroms.

In some embodiments, the co-crystalline Form I characterized by an X-ray powder diffraction pattern comprising a d-spacing value at about 3.1±0.5 degrees angstroms.

In some embodiments, the co-crystalline Form I characterized by an X-ray powder diffraction pattern comprising a d-spacing value at about 3.0±0.5 degrees angstroms.

In some embodiments, the co-crystalline Form I characterized by an X-ray powder diffraction pattern comprising a d-spacing value at about 2.8±0.5 degrees angstroms.

In some embodiments, the co-crystalline Form I characterized by an X-ray powder diffraction pattern comprising a d-spacing value at about 2.7±0.5 degrees angstroms.

In some embodiments, the co-crystalline Form I characterized by an X-ray powder diffraction pattern comprising one or more d-spacing values at about 9.8±0.5 degrees angstroms, at about 7.6±0.5 degrees angstroms, at about 5.9±0.5 degrees angstroms, at about 5.2±0.5 degrees angstroms, at about 5.1±0.5 degrees angstroms, at about 5.0±0.5 degrees angstroms, at about 4.9±0.5 degrees angstroms, at about 4.8±0.5 degrees angstroms, at about 4.2±0.5 degrees angstroms, at about 4.1±0.5 degrees angstroms, at about 4.1±0.5 degrees angstroms, at about 3.8±0.5 degrees angstroms, at about 3.6±0.5 degrees angstroms, at about 3.6±0.5 degrees angstroms, at about 3.5±0.5 degrees angstroms, at about 3.4±0.5 degrees angstroms, at about 3.4±0.5 degrees angstroms, at about 3.2±0.5 degrees angstroms, at about 3.2±0.5 degrees angstroms, at about 3.1±0.5 degrees angstroms, at about 3.0±0.5 degrees angstroms, at about 2.8±0.5 degrees angstroms, and at about 2.7±0.5 degrees angstroms.

In some embodiments, the co-crystalline Form U is characterized by an X-ray powder diffraction pattern comprising a d-spacing value substantially as shown in Table 5.

In some embodiments, the co-crystalline Form U is characterized by an X-ray powder diffraction pattern comprising a d-spacing value at about 16.6±0.5 degrees angstroms.

In some embodiments, the co-crystalline Form U is characterized by an X-ray powder diffraction pattern comprising a d-spacing value at about 11.6±0.5 degrees angstroms.

In some embodiments, the co-crystalline Form U is characterized by an X-ray powder diffraction pattern comprising a d-spacing value at about 9.7±0.5 degrees angstroms.

In some embodiments, the co-crystalline Form U is characterized by an X-ray powder diffraction pattern comprising a d-spacing value at about 8.3±0.5 degrees angstroms.

In some embodiments, the co-crystalline Form U is characterized by an X-ray powder diffraction pattern comprising a d-spacing value at about 7.4±0.5 degrees angstroms.

In some embodiments, the co-crystalline Form U is characterized by an X-ray powder diffraction pattern comprising a d-spacing value at about 6.2±0.5 degrees angstroms.

In some embodiments, the co-crystalline Form U is characterized by an X-ray powder diffraction pattern comprising a d-spacing value at about 6.1±0.5 degrees angstroms.

In some embodiments, the co-crystalline Form U is characterized by an X-ray powder diffraction pattern comprising a d-spacing value at about 5.8±0.5 degrees angstroms.

In some embodiments, the co-crystalline Form U is characterized by an X-ray powder diffraction pattern comprising a d-spacing value at about 5.6±0.5 degrees angstroms.

In some embodiments, the co-crystalline Form U is characterized by an X-ray powder diffraction pattern comprising a d-spacing value at about 5.3±0.5 degrees angstroms.

In some embodiments, the co-crystalline Form II is characterized by an X-ray powder diffraction pattern comprising a d-spacing value at about 5.2±0.5 degrees angstroms.

In some embodiments, the co-crystalline Form II is characterized by an X-ray powder diffraction pattern comprising a d-spacing value at about 5.1±0.5 degrees angstroms.

In some embodiments, the co-crystalline Form II is characterized by an X-ray powder diffraction pattern comprising a d-spacing value at about 5.0±0.5 degrees angstroms.

In some embodiments, the co-crystalline Form II is characterized by an X-ray powder diffraction pattern comprising a d-spacing value at about 5.0±0.5 degrees angstroms.

In some embodiments, the co-crystalline Form II is characterized by an X-ray powder diffraction pattern comprising a d-spacing value at about 4.8±0.5 degrees angstroms.

In some embodiments, the co-crystalline Form II is characterized by an X-ray powder diffraction pattern comprising a d-spacing value at about 4.8±0.5 degrees angstroms.

In some embodiments, the co-crystalline Form II is characterized by an X-ray powder diffraction pattern comprising a d-spacing value at about 4.7±0.5 degrees angstroms.

In some embodiments, the co-crystalline Form II is characterized by an X-ray powder diffraction pattern comprising a d-spacing value at about 4.6±0.5 degrees angstroms.

In some embodiments, the co-crystalline Form II is characterized by an X-ray powder diffraction pattern comprising a d-spacing value at about 4.4±0.5 degrees angstroms.

In some embodiments, the co-crystalline Form II is characterized by an X-ray powder diffraction pattern comprising a d-spacing value at about 4.2±0.5 degrees angstroms.

In some embodiments, the co-crystalline Form II is characterized by an X-ray powder diffraction pattern comprising a d-spacing value at about 4.0±0.5 degrees angstroms.

In some embodiments, the co-crystalline Form II is characterized by an X-ray powder diffraction pattern comprising a d-spacing value at about 4.0±0.5 degrees angstroms.

In some embodiments, the co-crystalline Form II is characterized by an X-ray powder diffraction pattern comprising a d-spacing value at about 3.9±0.5 degrees angstroms.

In some embodiments, the co-crystalline Form II is characterized by an X-ray powder diffraction pattern comprising a d-spacing value at about 3.8±0.5 degrees angstroms.

In some embodiments, the co-crystalline Form II is characterized by an X-ray powder diffraction pattern comprising a d-spacing value at about 3.7±0.5 degrees angstroms.

In some embodiments, the co-crystalline Form II is characterized by an X-ray powder diffraction pattern comprising a d-spacing value at about 3.7±0.5 degrees angstroms.

In some embodiments, the co-crystalline Form II is characterized by an X-ray powder diffraction pattern comprising a d-spacing value at about 3.5±0.5 degrees angstroms.

In some embodiments, the co-crystalline Form II is characterized by an X-ray powder diffraction pattern comprising a d-spacing value at about 3.4±0.5 degrees angstroms.

In some embodiments, the co-crystalline Form II is characterized by an X-ray powder diffraction pattern comprising a d-spacing value at about 3.4±0.5 degrees angstroms.

In some embodiments, the co-crystalline Form II is characterized by an X-ray powder diffraction pattern comprising a d-spacing value at about 3.3±0.5 degrees angstroms.

In some embodiments, the co-crystalline Form II is characterized by an X-ray powder diffraction pattern comprising a d-spacing value at about 3.3±0.5 degrees angstroms.

In some embodiments, the co-crystalline Form II is characterized by an X-ray powder diffraction pattern comprising a d-spacing value at about 3.2 degrees angstroms.

In some embodiments, the co-crystalline Form II is characterized by an X-ray powder diffraction pattern comprising one or more d-spacing values at about 16.6±0.5 degrees angstroms, at about 11.6±0.5 degrees angstroms, at about 9.7±0.5 degrees angstroms, at about 8.3±0.5 degrees angstroms, at about 7.4±0.5 degrees angstroms, at about 6.2±0.5 degrees angstroms, at about 6.1±0.5 degrees angstroms, at about 5.8±0.5 degrees angstroms, at about 5.6±0.5 degrees angstroms, at about 5.3±0.5 degrees angstroms, at about 5.2±0.5 degrees angstroms, at about 5.1±0.5 degrees angstroms, at about 5.0±0.5 degrees angstroms, at about 5.0±0.5 degrees angstroms, at about 4.8±0.5 degrees angstroms, at about 4.8±0.5 degrees angstroms, at about 4.7±0.5 degrees angstroms, at about 4.6±0.5 degrees angstroms, at about 4.4±0.5 degrees angstroms, at about 4.2±0.5 degrees angstroms, at about 4.0±0.5 degrees angstroms, at about 4.0±0.5 degrees angstroms, at about 3.9±0.5 degrees angstroms, at about 3.8±0.5 degrees angstroms, at about 3.7±0.5 degrees angstroms, at about 3.5±0.5 degrees angstroms, at about 3.4±0.5 degrees angstroms, at about 3.4±0.5 degrees angstroms, at about 3.3±0.5 degrees angstroms, at about 3.3±0.5 degrees angstroms, and at about 3.2 degrees angstroms.

In some embodiments, the co-crystalline Form III is characterized by an X-ray powder diffraction pattern comprising a d-spacing value substantially as shown in Table 6.

In some embodiments, the co-crystalline Form III is characterized by an X-ray powder diffraction pattern comprising a d-spacing value at about 6.8±0.5 degrees angstroms.

In some embodiments, the co-crystalline Form III is characterized by an X-ray powder diffraction pattern comprising a d-spacing value at about 6.5±0.5 degrees angstroms.

In some embodiments, the co-crystalline Form III is characterized by an X-ray powder diffraction pattern comprising a d-spacing value at about 6.2±0.5 degrees angstroms.

In some embodiments, the co-crystalline Form III is characterized by an X-ray powder diffraction pattern comprising a d-spacing value at about 3.4±0.5 degrees angstroms.

In some embodiments, the co-crystalline Form III is characterized by an X-ray powder diffraction pattern comprising a d-spacing value at about 3.3±0.5 degrees angstroms.

In some embodiments, the co-crystalline Form III is characterized by an X-ray powder diffraction pattern comprising a d-spacing value at about 2.8 degrees angstroms.

In some embodiments, the co-crystalline Form III is characterized by an X-ray powder diffraction pattern comprising one or more d-spacing values at about 6.8±0.5 degrees angstroms, at about 6.5±0.5 degrees angstroms, at about 6.2±0.5 degrees angstroms, at about 3.4±0.5 degrees angstroms, at about 3.3±0.5 degrees angstroms, and at about 2.8 degrees angstroms.

In some embodiments, the co-crystalline Form IV is characterized by an X-ray powder diffraction pattern comprising a d-spacing value substantially as shown in Table 7.

In some embodiments, the co-crystalline Form IV is characterized by an X-ray powder diffraction pattern comprising a d-spacing value at about 11.6±0.5 degrees angstroms.

In some embodiments, the co-crystalline Form IV is characterized by an X-ray powder diffraction pattern comprising a d-spacing value at about 6.8±0.5 degrees angstroms.

In some embodiments, the co-crystalline Form IV is characterized by an X-ray powder diffraction pattern comprising a d-spacing value at about 6.6±0.5 degrees angstroms.

In some embodiments, the co-crystalline Form IV is characterized by an X-ray powder diffraction pattern comprising a d-spacing value at about 5.3±0.5 degrees angstroms.

In some embodiments, the co-crystalline Form IV is characterized by an X-ray powder diffraction pattern comprising a d-spacing value at about 5.1±0.5 degrees angstroms.

In some embodiments, the co-crystalline Form IV is characterized by an X-ray powder diffraction pattern comprising a d-spacing value at about 4.9±0.5 degrees angstroms.

In some embodiments, the co-crystalline Form IV is characterized by an X-ray powder diffraction pattern comprising a d-spacing value at about 4.5±0.5 degrees angstroms.

In some embodiments, the co-crystalline Form IV is characterized by an X-ray powder diffraction pattern comprising a d-spacing value at about 4.3±0.5 degrees angstroms.

In some embodiments, the co-crystalline Form IV is characterized by an X-ray powder diffraction pattern comprising a d-spacing value at about 4.2±0.5 degrees angstroms.

In some embodiments, the co-crystalline Form IV is characterized by an X-ray powder diffraction pattern comprising a d-spacing value at about 4.0±0.5 degrees angstroms.

In some embodiments, the co-crystalline Form IV is characterized by an X-ray powder diffraction pattern comprising a d-spacing value at about 3.4±0.5 degrees angstroms.

In some embodiments, the co-crystalline Form IV is characterized by an X-ray powder diffraction pattern comprising a d-spacing value at about 2.9 degrees angstroms.

In some embodiments, the co-crystalline Form IV is characterized by an X-ray powder diffraction pattern comprising one or more d-spacing values at about 11.6±0.5 degrees angstroms, at about 6.8±0.5 degrees angstroms, at about 6.6±0.5 degrees angstroms, at about 5.3±0.5 degrees angstroms, at about 5.1±0.5 degrees angstroms, at about 4.9±0.5 degrees angstroms, at about 4.5±0.5 degrees angstroms, at about 4.3±0.5 degrees angstroms, at about 4.2±0.5 degrees angstroms, at about 4.0±0.5 degrees angstroms, at about 3.4±0.5 degrees angstroms, and at about 2.9 degrees angstroms.

In some embodiments, the co-crystalline Form V is characterized by an X-ray powder diffraction pattern comprising a d-spacing value substantially as shown in Table 8.

In some embodiments, the co-crystalline Form V is characterized by an X-ray powder diffraction pattern comprising a d-spacing value at about 12.6±0.5 degrees angstroms.

In some embodiments, the co-crystalline Form V is characterized by an X-ray powder diffraction pattern comprising a d-spacing value at about 8.3±0.5 degrees angstroms.

In some embodiments, the co-crystalline Form V is characterized by an X-ray powder diffraction pattern comprising a d-spacing value at about 6.2±0.5 degrees angstroms.

In some embodiments, the co-crystalline Form V is characterized by an X-ray powder diffraction pattern comprising a d-spacing value at about 4.2±0.5 degrees angstroms.

In some embodiments, the co-crystalline Form V is characterized by an X-ray powder diffraction pattern comprising a d-spacing value at about 3.7±0.5 degrees angstroms.

In some embodiments, the co-crystalline Form V is characterized by an X-ray powder diffraction pattern comprising a d-spacing value at about 3.4±0.5 degrees angstroms.

In some embodiments, the co-crystalline Form V is characterized by an X-ray powder diffraction pattern comprising a d-spacing value at about 3.4±0.5 degrees angstroms.

In some embodiments, the co-crystalline Form V is characterized by an X-ray powder diffraction pattern comprising a d-spacing value at about 3.1±0.5 degrees angstroms.

In some embodiments, the co-crystalline Form V is characterized by an X-ray powder diffraction pattern comprising a d-spacing value at about 3.0 degrees angstroms.

In some embodiments, the co-crystalline Form V is characterized by an X-ray powder diffraction pattern comprising one or more d-spacing values at about 12.6±0.5 degrees angstroms, at about 8.3±0.5 degrees angstroms, at about 6.2±0.5 degrees angstroms, at about 4.2±0.5 degrees angstroms, at about 3.7±0.5 degrees angstroms, at about 3.4±0.5 degrees angstroms, at about 3.4±0.5 degrees angstroms, at about 3.1±0.5 degrees angstroms, and at about 3.0 degrees angstroms.

In some embodiments, the co-crystalline Form VI is characterized by an X-ray powder diffraction pattern comprising a d-spacing value substantially as shown in Table 9.

In some embodiments, the co-crystalline Form VI is characterized by an X-ray powder diffraction pattern comprising a d-spacing value at about 5.5±0.5 degrees angstroms.

In some embodiments, the co-crystalline Form VI is characterized by an X-ray powder diffraction pattern comprising a d-spacing value at about 4.9±0.5 degrees angstroms.

In some embodiments, the co-crystalline Form VI is characterized by an X-ray powder diffraction pattern comprising a d-spacing value at about 4.4±0.5 degrees angstroms.

In some embodiments, the co-crystalline Form VI is characterized by an X-ray powder diffraction pattern comprising a d-spacing value at about 3.6±0.5 degrees angstroms.

In some embodiments, the co-crystalline Form VI is characterized by an X-ray powder diffraction pattern comprising a d-spacing value at about 3.5±0.5 degrees angstroms.

In some embodiments, the co-crystalline Form VI is characterized by an X-ray powder diffraction pattern comprising a d-spacing value at about 2.9±0.5 degrees angstroms.

In some embodiments, the co-crystalline Form VI is characterized by an X-ray powder diffraction pattern comprising a d-spacing value at about 2.9 degrees angstroms.

In some embodiments, the co-crystalline Form VI is characterized by an X-ray powder diffraction pattern comprising one or more d-spacing values at about 5.5±0.5 degrees angstroms, at about 4.9±0.5 degrees angstroms, at about 4.4±0.5 degrees angstroms, at about 3.6±0.5 degrees angstroms, at about 3.5±0.5 degrees angstroms, at about 2.9±0.5 degrees angstroms, and at about 2.9 degrees angstroms.

In some embodiments, the co-crystalline Form VII is characterized by an X-ray powder diffraction pattern comprising a d-spacing value substantially as shown in Table 10.

In some embodiments, the co-crystalline Form VII is characterized by an X-ray powder diffraction pattern comprising a d-spacing value at about 11.6±0.5 degrees angstroms.

In some embodiments, the co-crystalline Form VII is characterized by an X-ray powder diffraction pattern comprising a d-spacing value at about 8.2±0.5 degrees angstroms.

In some embodiments, the co-crystalline Form VII is characterized by an X-ray powder diffraction pattern comprising a d-spacing value at about 6.3±0.5 degrees angstroms.

In some embodiments, the co-crystalline Form VII is characterized by an X-ray powder diffraction pattern comprising a d-spacing value at about 5.8±0.5 degrees angstroms.

In some embodiments, the co-crystalline Form VII is characterized by an X-ray powder diffraction pattern comprising a d-spacing value at about 4.1±0.5 degrees angstroms.

In some embodiments, the co-crystalline Form VII is characterized by an X-ray powder diffraction pattern comprising a d-spacing value at about 3.9±0.5 degrees angstroms.

In some embodiments, the co-crystalline Form VII is characterized by an X-ray powder diffraction pattern comprising a d-spacing value at about 3.0 degrees angstroms.

In some embodiments, the co-crystalline Form VII is characterized by an X-ray powder diffraction pattern comprising one or more d-spacing values at about 11.6±0.5 degrees angstroms, at about 8.2±0.5 degrees angstroms, at about 6.3±0.5 degrees angstroms, at about 5.8±0.5 degrees angstroms, at about 4.1±0.5 degrees angstroms, at about 3.9±0.5 degrees angstroms, and at about 3.0 degrees angstroms.

In some embodiments, the crystalline Form VIII is characterized by an X-ray powder diffraction pattern comprising a d-spacing value substantially as shown in Table 11.

In some embodiments, at about the crystalline Form VIII is characterized by an X-ray powder diffraction pattern comprising d-spacing values at about 8.41±0.5 degrees angstroms, at about 7.99±0.5 degrees angstroms, at about 6.05±0.5 degrees angstroms, at about 5.86±0.5 degrees angstroms, at about 5.22±0.5 degrees angstroms, at about 4.96±0.5 degrees angstroms, at about 4.87±0.5 degrees angstroms, at about 4.21±0.5 degrees angstroms, at about 4.00±0.5 degrees angstroms, at about 3.78±0.5 degrees angstroms, at about 3.49±0.5 degrees angstroms, at about 3.35±0.5 degrees angstroms, at about 3.32±0.5 degrees angstroms, at about 3.21±0.5 degrees angstroms, and at about 3.15±0.5 degrees angstroms.

In some embodiments, the X-ray powder diffraction peaks recited herein for particular embodiments having d-spacing values can vary by ±4% nm, by ±3% nm, by ±2% nm, or by ±1% nm or by ±4% angstroms, by ±3% angstroms, by ±2% angstroms, or by ±1% angstroms.

One skilled in the art will understand that the relative intensities and positions of the peaks obtained by X-ray powder diffraction may vary depending upon, inter alia, the sample preparation technique, the sample mounting procedure, and the particular instrument employed. For example, in some embodiments, the listed X-ray powder diffraction pattern peaks for any of the co-crystalline Forms I-VII, or the crystalline Form VIII are about ±0.2 degrees 2θ.

In some embodiments, the co-crystalline Forms I-VII, the co-crystalline forms of the compound of Formula IV-I, and the crystalline Form VIII are characterized using Proton Nuclear Magnetic Resonance Spectroscopy ($^1$H NMR). For example, FIGS. 9, 20, 18, and 22 show Proton Nuclear Magnetic Resonance Spectroscopy ($^1$H NMR) analysis of the co-crystalline Form I, Form II. Form III, and Form IV, respectively. Other methods for characterizing the co-crystalline Forms I-VII and the crystalline Form VIII could also be used.

The co-crystalline Forms I-VII and the crystalline Form VIII can have any desired degree of purity relative to other substances or components in the preparation. In some embodiments, any form of the co-crystalline Forms I-VII is provided such that it is substantially pure, such as, for example, having greater than 30%, greater than 40%, greater than 50%, greater than 60%, greater than 70%, greater than 80%, greater than 85%, greater than 90%, greater than 95%, greater than 96%, greater than 97%, greater than 98%, greater than 99%, greater than 99.2%, greater than 99.4%, greater than 99.5%, greater than 99.6%, greater than 99.7%, or greater than 99.9% purity, relative to other substances or components in the preparation.

In exemplary embodiments, any one of the crystalline forms as described or provided herein, such as the co-crystalline Forms I-VII, the co-crystalline forms of the compound of Formula IV-I, and the crystalline Form VIII is about 45% to 95% pure, such as, for example, about 50% to 95% pure, about 55% to 90% pure, about 60% to 95% pure, or about 70% to 99% pure, relative to other substances or components in the preparation. In some embodiments, the co-crystalline Form I, Form II. Form III, Form IV. Form V. Form VI, or Form VII is about 95% to 99% pure. In some embodiments, the crystalline form is about 90% to 95% pure. In some embodiments, the crystalline form is about 85% to 90% pure. In some embodiments, the crystalline form is about 80% to 85% pure. In some embodiments, the crystalline form is about 75% to 80% pure. In some embodiments, the co-crystalline Form I is about 70% to 75% pure. In certain embodiments, the crystalline form is about 65% to 70% pure. In some embodiments, the crystalline form is about 60% to 65% pure. In other embodiments, the crystalline form is about 55% to 60% pure. In yet other embodiments, the co-crystalline Form I is about 50% to 55% pure. In some embodiments, the crystalline form is about 45% to 50% pure.

In some embodiments, any one of the crystalline forms as described or provided herein, such as the co-crystalline Forms I-VII, the co-crystalline forms of the compound of Formula IV-I. and the crystalline Form VIII may comprise one or more impurities and/or a degradation product, such as a hydrolysis product, acetylation product, a formylation product, an oxidation product, a water-mediated degradation product, and/or a deamidation product. In some embodiments, a composition comprising any one of the crystalline forms as described or provided herein, such as the co-crystalline Forms I-VII, the co-crystalline forms of the compound of Formula IV-1, and the crystalline Form VIII may comprise one or more impurities and/or a degradation product, such as a hydrolysis product, acetylation product, a formylation product, an oxidation product, a water-mediated degradation product, and/or a deamidation product. In some embodiments, one or more impurities may be biologically active.

In some embodiments, any one of the crystalline forms as described or provided herein, such as the co-crystalline Forms I-VII, the co-crystalline forms of the compound of Formula IV-I, and the crystalline Form VIII and/or the composition thereof comprising any one of the crystalline forms as described or provided herein, such as the co-crystalline Forms I-VII, the co-crystalline forms of the compound of Formula IV-I. and the crystalline Form VIII can contain any desired purity relative to hydrolysis product(s). In some embodiments, the composition comprises less than about 10% by weight of hydrolysis product(s), relative to the total weight of any one of the crystalline forms as described or provided herein and/or the composition thereof, such as, for example, less than about 7.5 wt. %, less than about 5 wt. %, or less than about 2 wt. % of hydrolysis product(s). In some embodiments, any one of the crystalline forms as described or provided herein, such as the co-crystalline Forms I-VII, the co-crystalline forms of the compound of Formula IV-I. and the crystalline Form VIII and/or the composition thereof comprises from about 0.05% to about 5% by weight of hydrolysis product(s). In some embodiments, any one of the crystalline forms as described or provided herein, such as the co-crystalline Forms I-VII, the co-crystalline forms of the compound of Formula IV-I. and the crystalline Form VIII and/or the composition thereof comprises from about 0.05% to about 2% by weight of the hydrolysis product(s). In some embodiments, any one of the crystalline forms as described or provided herein, such as the co-crystalline Forms I-VII, the co-crystalline forms of the compound of Formula IV-I, and the crystalline Form VIII and/or the composition thereof comprises from about 0.1% to about 2% by weight of the hydrolysis product(s). In some embodiments, any one of the crystalline forms as described or provided herein, such as the co-crystalline Forms I-VII, the co-crystalline forms of the compound of Formula IV-I, and the crystalline Form VIII and/or the composition thereof comprises from about 0.01% to about 2% by weight of the hydrolysis product(s).

Alternatively. or in addition, any one of the crystalline forms as described or provided herein, such as the co-crystalline Forms I-VII, the co-crystalline forms of the compound of Formula IV-I, and the crystalline Form VIII and/or the composition thereof comprising any one of the crystalline forms as described or provided herein, such as the co-crystalline Forms I-VII, the co-crystalline forms of the compound of Formula IV-I. and the crystalline Form VIII can contain any desired purity relative to acetylation product(s). In some embodiments, the acetylation product may comprise less than 10% by weight of any one of the crystalline forms as described or provided herein, such as the co-crystalline Forms I-VI, the co-crystalline forms of the compound of Formula IV-I, and the crystalline Form VIII and/or the compositions thereof. In some embodiments, the acetylation product may comprise less than 7.5% by weight of any one of the crystalline forms as described or provided herein, such as the co-crystalline Forms I-VII, the co-crystalline forms of the compound of Formula IV-I, and the crystalline Form VIII and/or the composition thereof. In some embodiments, the acetylation product may comprise less than 5% by weight of any one of the crystalline forms as described or provided herein, such as the co-crystalline Forms I-VII, the co-crystalline forms of the compound of Formula IV-I, and the crystalline Form VIII and/or the composition thereof. In some embodiments, the acetylation product may comprise less than 2% by weight of any one of the crystalline forms as described or provided herein, such as the co-crystalline Forms I-VII, the co-crystalline forms of the compound of Formula IV-I. and the crystalline Form VIII and/or the composition thereof. In some embodiments, the acetylation product may comprise less than 1% by weight of any one of the crystalline forms as described or provided herein, such as the co-crystalline Forms I-VII, the co-crystalline forms of the compound of Formula IV-I, and the crystalline Form VIII and/or the composition thereof. In some embodiments, the acetylation product may comprise less than 0.5% by weight of any one of the crystalline forms as described or provided herein and/or the composition thereof. In some embodiments, the acetylation product may comprise from about 0.05% to about 5% by weight of any one of the crystalline forms as described or provided herein and/or the composition thereof. In some embodiments, the acetylation product may comprise from about 0.05% to about 2% by weight of any one of the crystalline forms as described or provided herein and/or the composition thereof. In some embodiments, the acetylation product may comprise from about 0.1% to about 2% by weight of any one of the crystalline forms as described or provided herein and/or the composition thereof. In some embodiments, the acetylation product may comprise from about 0.01% to about 2% by weight of the composition.

Alternatively, or in addition, any one of the crystalline forms as described or provided herein, such as the co-crystalline Forms I-VII, the co-crystalline forms of the compound of Formula IV-I, and the crystalline Form VIII and/or the composition thereof comprising any one of the crystalline forms as described or provided herein, such as the co-crystalline Forms I-VII, the co-crystalline forms of the compound of Formula IV-I, and the crystalline Form VIII can contain any desired purity relative to formylation product(s). In some embodiments, the formylation product may comprise less than 10% by weight of any one of the crystalline forms as described or provided herein and/or the composition thereof. In some embodiments, the formylation product may comprise less than 7.5% by weight of any one of the crystalline forms as described or provided herein and/or the composition thereof. In some embodiments, the formylation product may comprise less than 5% by weight of any one of the crystalline forms as described or provided herein and/or the composition thereof. In some embodiments, the formylation product may comprise less than 2% by weight of any one of the crystalline forms as described or provided herein and/or the composition thereof. In some embodiments, the formylation product may comprise from about 0.05% to about 5% by weight of any one of the crystalline forms as described or provided herein and/or the composition thereof. In some embodiments, the formylation product may comprise from about 0.05% to about 2% by weight of any one of the crystalline forms as described or provided herein and/or the composition thereof. In some embodiments, the formylation product may comprise from about 0.1% to about 2% by weight of any one of the crystalline forms as described or provided herein and/or the composition thereof.

Alternatively, or in addition, any one of the crystalline forms as described or provided herein, such as the co-crystalline Forms I-VII, the co-crystalline forms of the compound of Formula IV-I, and the crystalline Form VIII and/or the composition thereof comprising any one of the crystalline forms as described or provided herein, such as the co-crystalline Forms I-VII, the co-crystalline forms of the compound of Formula IV-I. and the crystalline Form VIII can contain any desired purity relative to oxidation product(s). In some embodiments, the oxidation product may comprise less than 10% by weight of any one of the crystalline forms as described or provided herein and/or the composition thereof. In some embodiments, the oxidation product may comprise less than 7.5% by weight of any one of the crystalline forms as described or provided herein and/or the composition thereof. In some embodiments, the oxidation product may comprise less than 5% by weight of any one of the crystalline forms as described or provided herein and/or the composition thereof. In some embodiments, the oxidation product may comprise less than 2% by weight of any one of the crystalline forms as described or provided herein and/or the composition thereof. In some embodiments, the oxidation product may comprise from about 0.05% to about 5% by weight of any one of the crystalline forms as described or provided herein and/or the composition thereof. In some embodiments, the oxidation product may comprise from about 0.05% to about 2% by weight of any one of the crystalline forms as described or provided herein and/or the composition thereof. In some embodiments, the oxidation product may comprise from about 0.1% to about 2% by weight of any one of the crystalline forms as described or provided herein and/or the composition thereof. In some embodiments, the oxidation product may comprise from about 0.01% to about 2% by weight of any one of the crystalline forms as described or provided herein and/or the composition thereof.

Alternatively, or in addition, any one of the crystalline forms as described or provided herein, such as the co-crystalline Forms I-VII, the co-crystalline forms of the compound of Formula IV-I, and the crystalline Form VIII and/or the composition thereof comprising any one of the crystalline forms as described or provided herein, such as the co-crystalline Forms I-VII, the co-crystalline forms of the compound of Formula IV-I, and the crystalline Form V ill can contain any desired purity relative to water-mediated degradation product(s). In some embodiments, the water-mediated degradation product(s) may comprise less than 10% by weight of any one of the crystalline forms as described or provided herein and/or the composition thereof. In some embodiments, the water-mediated degradation product(s) may comprise less than 7.5% by weight of any one of the crystalline forms as described or provided herein and/or the composition thereof. In some embodiments, the water-mediated degradation product(s) may comprise less than 5% by weight of any one of the crystalline forms as described or provided herein and/or the composition thereof. In other embodiments, the water-mediated degradation product(s) may comprise less than 2% by weight of any one of the crystalline forms as described or provided herein and/or the composition thereof. In some embodiments, the water-mediated degradation product(s) may comprise from about 0.05% to about 5% by weight of any one of the crystalline forms as described or provided herein and/or the composition thereof. In exemplary embodiments, the water-mediated degradation product(s) may comprise from about 0.05% to about 2% by weight of any one of the crystalline forms as described or provided herein and/or the composition thereof. In some embodiments, the water-mediated degradation product(s) may comprise from about 0.1% to about 2% by weight of any one of the crystalline forms as described or provided herein and/or the composition thereof. In some embodiments, the water-mediated degradation product(s) may comprise from about 0.01% to about 2% by weight of any one of the crystalline forms as described or provided herein and/or the composition thereof Alternatively, or in addition, any one of the crystalline forms as described or provided herein, such as the co-crystalline Forms I-VII, the co-crystalline forms of the compound of Formula IV-I, and the crystalline Form VIII and/or the composition thereof comprising any one of the crystalline forms as described or provided herein, such as the co-crystalline Forms I-VII, the co-crystalline forms of the compound of Formula IV-I, and the crystalline Form VIII can contain any desired purity relative to deamidation product(s). In some embodiments, the deamidation product may comprise less than 10% by weight of any one of the crystalline forms as described or provided herein and/or the composition thereof. In some embodiments, the deamidation product may comprise less than 7.5% by weight of any one of the crystalline forms as described or provided herein and/or the composition thereof. In some embodiments, the deamidation product may comprise less than 5% by weight of any one of the crystalline forms as described or provided herein and/or the composition thereof. In other embodiments, the deamidation product may comprise less than 2% by weight of any one of the crystalline forms as described or provided herein and/or the composition thereof. In some embodiments, the deamidation product may comprise from about 0.05% to about 5% by weight of any one of the crystalline forms as described or provided herein and/or the composition thereof. In some embodiments, the deamidation product may comprise from about 0.05% to about 2% by weight of any one of the crystalline forms as described or provided herein and/or the composition thereof. In some embodiments, the deamidation product may comprise from about 0.1% to about 2% by weight of any one of the crystalline forms as described or provided herein and/or the composition thereof. In some embodiments, the deamidation product may comprise from about 0.01% to about 2% by weight of any one of the crystalline forms as described or provided herein and/or the composition thereof.

In some embodiments, a composition is provided comprising any one of the crystalline forms as described or provided herein, such as the co-crystalline Forms I-VII, the co-crystalline forms of the compound of Formula IV-I, and the crystalline Form VIII and less than 10 wt. % such as less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of a degradation product, such as a hydrolysis product, a formylation product, an oxidation product, a water-mediated degradation product, and/or a deamidation product.

In some embodiments, a composition is provided comprising any one of the crystalline forms as described or provided herein, such as the co-crystalline Forms I-VII, the co-crystalline forms of the compound of Formula IV-I, and the crystalline Form VIII and less than 20 wt. % such as less than 18 wt. %, less than 16 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of a degradation product, such as a hydrolysis product, an acetylation product, a formylation product, an oxidation product, a water-mediated degradation product, and/or a deamidation product.

In some embodiments, a composition is provided comprising any one of the crystalline forms as described or provided herein, such as the co-crystalline Forms I-VII, the co-crystalline forms of the compound of Formula IV-I, and the crystalline Form VIII and less than 10 wt. % such as less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of one or more impurities and/or a degradation product, such as a hydrolysis product, a formylation product, an oxidation product, a water-mediated degradation product, and/or a deamidation product.

In some embodiments, a composition is provided comprising any one of the crystalline forms as described or provided herein, such as the co-crystalline Forms I-VII, the co-crystalline forms of the compound of Formula IV-I, and the crystalline Form VIII and less than 20 wt. % such as less than 18 wt. %, less than 16 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of one or more impurities and/or a degradation product, such as a hydrolysis product, an acetylation product, a formylation product, an oxidation product, a water-mediated degradation product, and/or a deamidation product.

In some embodiments, a composition is provided comprising any one of the crystalline forms as described or provided herein, such as the co-crystalline Forms I-VII, the co-crystalline forms of the compound of Formula IV-I, and the crystalline Form VIII and less than about 40 wt %, such as less than about 30 wt. %, less than about 20 wt. %, less than about 15 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, less than about 0.1 wt. %, or less than about 0.01 wt. % of amorphous form of the compound of Formula I. Formula I-a, or Formula I-b.

In some embodiments, processes for preparing co-crystalline forms of the compound of Formula I, Formula I-a, or Formula I-b are provided. In some embodiments, the co-crystalline any one of the crystalline forms as described or provided herein is produced by precipitating and crystallizing the compound of Formula I. Formula I-a, or Formula I-b and optionally isolating the co-crystalline any one of the crystalline forms as described or provided herein. In some embodiments, the co-crystalline any one of the crystalline forms as described or provided herein is prepared by slurrying the compound of Formula I, Formula I-a, or Formula I-b in an organic solvent and optionally isolating the co-crystalline any one of the crystalline forms as described or provided herein. In some embodiments, the co-crystalline any one of the crystalline forms as described or provided herein is prepared by slurring and crystallizing the compound of Formula I, Formula I-a, or Formula I-b in a super saturated organic solvent and optionally isolating the co-crystalline any one of the crystalline forms as described or provided herein.

Any suitable organic solvent can be used in this regard, such as, for example, acetonitrile, ethyl acetate, cyclohexane, toluene, methanol, and any combination thereof, at various strengths or concentrations. Such solvents may include but are not limited to, acetonitrile, ethyl acetate, cyclohexane, toluene, methanol, and a combination thereof. In some embodiments, the organic solvent comprises acetonitrile. In some embodiments, the organic solvent comprises ethyl acetate. In some embodiments, the organic solvent comprises cyclohexane. In some embodiments, the organic solvent is toluene. In some embodiments, the organic solvent is methanol.

The co-crystalline any one of the crystalline forms as described or provided herein of the compound of Formula I, Formula I-a, or Formula I-b may be identified, characterized, and distinguished from amorphous or oil form using any suitable manner. One skilled in the art will know many different methods of identification and characterization of the co-crystalline any one of the crystalline forms as described or provided herein. For example, the co-crystalline any one of the crystalline forms as described or provided herein of the compound of Formula I, Formula I-a, or Formula I-b may be identified and characterized based on differences in diffraction, thermal, intensity, and/or spectroscopic properties of the amorphous and co-crystalline form. Suitable methods include, but are not limited to, X-ray diffractometry, Proton Nuclear Magnetic Resonance Spectroscopy ($^1$H NMR), thermogravimetric analysis (TGA), and differential scanning calorimetry (DSC).

In some embodiments, processes for preparing a co-crystalline form of the compound having a formula of

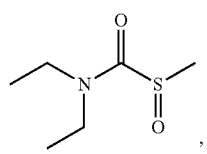

Formula I

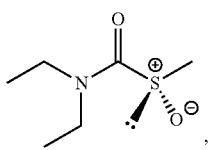

Formula I-a

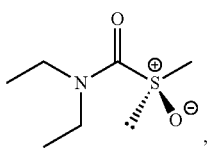

Formula I-b

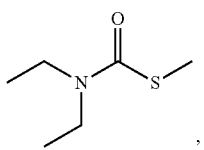

Formula II

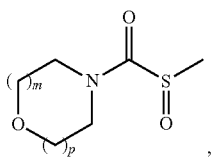

Formula III

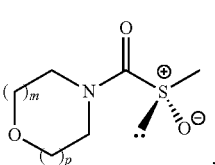

Formula III-a

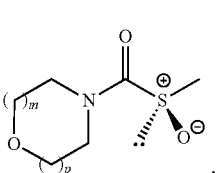

Formula III-b

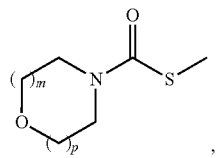

Formula VI

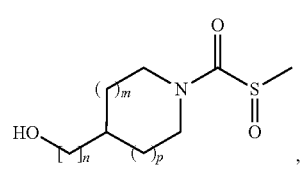

Formula IV

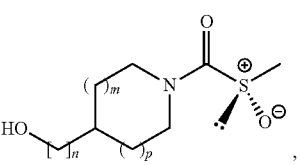

Formula IV-a

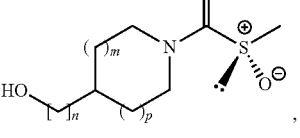

Formula IV-b

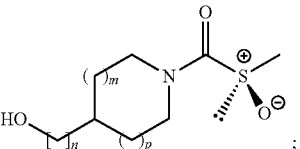

Formula V

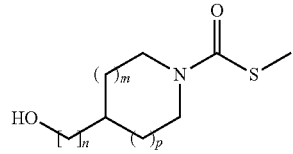

wherein n is 0-6, and a coformer as described or provided herein. In some embodiments, the process comprises co-crystallizing the compound and the coformer to form the co-crystalline form of the compound and the coformer and optionally isolating the co-crystalline form of the compound and the coformer. In some embodiments, the process comprises dry grinding the compound and the coformer to form the co-crystalline form therefrom. In some embodiments, the process comprises slurrying the compound and the coformer in an organic solvent to form the co-crystalline form therefrom. In some embodiments, the process further comprises washing the slurry with the organic solvent. In some embodiments, the organic solvent is selected from the group consisting of acetonitrile, ethyl acetate, cyclohexane, toluene, methanol, and any combination thereof. In some embodiments, the organic solvent is acetonitrile. In some embodiments, the organic solvent is ethyl acetate. In some embodiments, the organic solvent is cyclohexane. In some embodiments, the organic solvent is toluene. In some embodiments, the organic solvent is methanol. In some embodiments, the organic solvent is and any combination of acetonitrile, ethyl acetate, cyclohexane, toluene, methanol. In some embodiments, the coformer is a coformer provided and described herein. In some embodiments, the coformer is urea, 3,5-dihydroxybenzoic acid, trimesic acid, ellagic acid, $MgCl_2$, or $CaCl_2$, or any combination thereof. In some embodiments, the coformer is urea. In some embodiments, the coformer is 3,5-dihydroxybenzoic acid. In some embodiments, the coformer is trimesic acid. In some embodiments, the coformer is ellagic acid. In some embodiments, the co-crystalline form is: a co-crystalline Form I of the compound and urea, wherein the molar ratio of the compound to the urea is about 1:1; a co-crystalline Form II of the compound and trimesic acid, wherein the molar ratio of the compound to the trimesic acid is about 1:1; a co-crystalline Form III of the compound and 3,5-dihydroxybenzoic acid, wherein the molar ratio of the compound to 3,5-dihydroxybenzoic acid is about 1:2; a co-crystalline Form IV of the compound and 3,5-dihydroxybenzoic acid, wherein the molar ratio of the compound to 3,5-dihydroxybenzoic acid is about 1:1; a co-crystalline Form V of the compound and ellagic acid, wherein the molar ratio of the compound to ellagic acid is about 1:1; a co-crystalline Form VI of the compound and MgCl$_2$, wherein the molar ratio of the compound to the MgCl$_2$ is about 1:1; or a co-crystalline Form VII of the compound and CaCl$_2$, wherein the molar ratio of the compound to the CaCl$_2$ is about 1:1. In some embodiments, the process further comprises filtering the slurry. In some embodiments, the process further comprises washing the slurry with the organic solvent. Additionally, any suitable organic solvent can be used in this regard, such as, for example, water, DMSO, acids, and polar or non-polar solvents, at various strengths or concentrations. Such solvents may include, but are not limited to, acetonitrile, ethyl acetate, toluene, cyclohexane, dichloromethane, chloroform, methanol, 2-propanol, tetrahydrofuran, acetone, H$_2$O, ethanol, nitromethane, isopropyl acetate, n-pentane, n-hexane, 1-propanol, methyl acetate, ethyl ether, octane, and any combination thereof.

In some embodiments, processes for preparing a crystalline form of a compound having a formula of

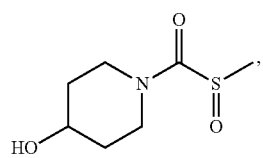

Formula IV-I comprising crystallizing

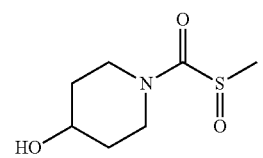

Formula IV-I to form Form VIII and optionally isolating the Form VIII. In some embodiments, the compound has a formula of

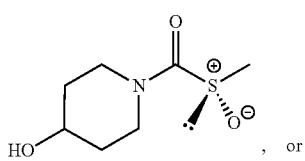

Formula IV-Ia

, or

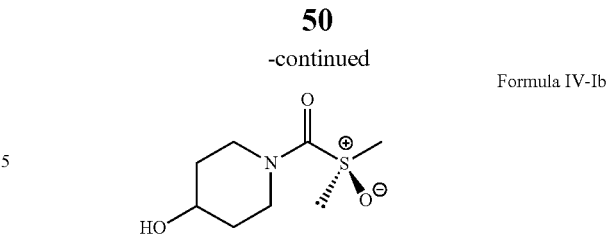

Formula IV-Ib or both. In some embodiments, the crystallizing comprises dissolving the compound in an organic solvent and crystallizing the compound to form Form VIII therefrom. In some embodiments, the organic solvent is selected from the group consisting of acetonitrile, ethyl acetate, toluene, cyclohexane, dichloromethane, chloroform, methanol, 2-propanol, tetrahydrofuran, acetone, H$_2$O, ethanol, nitromethane, isopropyl acetate, n-pentane, n-hexane, 1-propanol, methyl acetate, ethyl ether, octane, and any combination thereof. In some embodiments, the organic solvent is acetonitrile. In some embodiments, the organic solvent is ethyl acetate. In some embodiments, the organic solvent is toluene. In some embodiments, the organic solvent is cyclohexane. In some embodiments, the organic solvent is dichloromethane. In some embodiments, the organic solvent is chloroform. In some embodiments, the organic solvent is methanol. In some embodiments, the organic solvent is 2-propanol. In some embodiments, the organic solvent is tetrahydrofuran. In some embodiments, the organic solvent is acetone. In some embodiments, the organic solvent is H$_2$O. In some embodiments, the organic solvent is ethanol. In some embodiments, the organic solvent is nitromethane. In some embodiments, the organic solvent is isopropyl acetate. In some embodiments, the organic solvent is n-pentane. In some embodiments, the organic solvent is n-hexane. In some embodiments, the organic solvent is 1-propanol. In some embodiments, the organic solvent is methyl acetate. In some embodiments, the organic solvent is ethyl ether. In some embodiments, the organic solvent is octane.

Pharmaceutical Compositions/Formulations

Embodiments described herein can be used in pharmaceutical compositions and can be formulated by standard techniques using one or more physiologically acceptable carriers or excipients. In some embodiments, the formulations may contain a buffer and/or a preservative. Any crystalline form as described or provided herein, such as the co-crystalline forms of Form I-VII, the co-crystalline forms of the compound of Formula IV-I, and the crystalline Form VIII and their physiologically acceptable salts, anhydrates, hydrates and/or solvates, can be formulated for administration by any suitable route, including via inhalation, topically, nasally, orally, parenterally (for example, intravenously, intraperitoneally, intravesically or intrathecally) or rectally in a vehicle comprising one or more pharmaceutically acceptable carriers, the proportion of which is determined by the route of administration and standard biological practice. Other routes of administration are also described herein and can be used as well.

In some embodiments, pharmaceutical compositions are provided comprising effective amounts of any crystalline form as described or provided herein, such as the co-crystalline forms of Form I-VII, the co-crystalline forms of the compound of Formula IV-I, and the crystalline Form VIII with, for example, pharmaceutically acceptable diluents, preservatives, solubilizers, emulsifiers, adjuvants and/or other carriers. Such compositions are known to one skilled in the art and the compositions can be formulated using standard techniques. For example, diluents of various buffer content such as, but not limited to, TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate). pH and ionic strength; additives such as detergents and solubilizing agents (e.g., surfactants such as Pluronics. Tween 20. Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes may be used. Hyaluronic acid may also be used. Such compositions can be employed to influence the physical state, stability, rate of in vivo release, and rate of in vivo clearance of a composition comprising the co-crystalline of any one of Form I-VII or the crystalline Form VIII as described herein. See, e.g., Remington's Pharmaceutical Sciences, 18th Ed. (1990, Mack Publishing Co., Easton, Pa. 18042) pages 1435-1712 which are herein incorporated by reference. Where a buffer is to be included in the formulations, the buffer can be, for example, but not limited to, sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, or mixtures thereof. Each buffer can be used independently or in combination with another buffer. In some embodiments, the buffer is glycylglycine, sodium dihydrogen phosphate, disodium hydrogen phosphate, sodium phosphate or mixtures thereof.

Where a pharmaceutically acceptable preservative is to be included in the formulations, the preservative can be, but is not limited to, phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. In some embodiments, the preservative is phenol and/or m-cresol.

In some embodiments, the preservative is present in a concentration from about 0.1 mg/ml to about 100 mg/ml, more preferably in a concentration from about 0.1 mg/ml to about 50 mg/ml, about 0.1 mg/ml to about 25 mg/ml. In some embodiments, the preservative is present in a concentration from about 0.1 mg/ml to about 10 mg/ml.

The use of a preservative in pharmaceutical compositions is well known to the skilled person. For convenience, reference is made to Remington: The Science and Practice of Pharmacy. 19th edition, 1995.

In some embodiments, the formulation may further comprise a chelating agent where the chelating agent may be salts of ethlenediaminetetraacetic acid (EDTA), citric acid, and aspartic acid, and mixtures thereof.

In some embodiments, the chelating agent is present in a concentration from 0.1 mg/ml to 10 mg/ml, particularly in a concentration from 0.1 mg/ml to 5 mg/ml. In some embodiments, the chelating agent is present in a concentration from 0.1 mg/ml to 2 mg/ml. In some embodiments, the chelating agent is present in a concentration from 2 mg/ml to 5 mg/ml.

The use of a chelating agent in pharmaceutical compositions is well known to the skilled person. For convenience, reference is made to Remington: The Science and Practice of Pharmacy. 19th edition. 1995.

In some embodiments, the formulation may further comprise a stabilizer selected from the group of high molecular weight polymers or low molecular compounds where such stabilizers include, but are not limited to, polyethylene glycol (e.g., PEG 3350), polyvinylalcohol (PVA), polyvinylpyrrolidone, carboxymethylcellulose, different salts (e.g., sodium chloride), L-glycine, L-histidine, imidazole, arginine, lysine, isoleucine, aspartic acid, tryptophan, threonine and mixtures thereof. In some embodiments, the stabilizer is L-histidine, imidazole, arginine, or any combination thereof.

In some embodiments, the high molecular weight polymer is present in a concentration from 0.1 mg/ml to 100 mg/ml, in a concentration from 0.1 mg/ml to 50 mg/ml. In some embodiments, the high molecular weight polymer is present in a concentration from 0.1 mg/ml to 5 mg/ml. In some embodiments, the high molecular weight polymer is present in a concentration from 5 mg/ml to 10 mg/ml. In some embodiments, the high molecular weight polymer is present in a concentration from 10 mg/ml to 20 mg/ml. In some embodiments, the high molecular weight polymer is present in a concentration from 20 mg/ml to 30 mg/ml. In some embodiments, the high molecular weight polymer is present in a concentration from 30 mg/ml to 50 mg/ml.

In some embodiments, the low molecular weight polymer is present in a concentration from 0.1 mg/ml to 100 mg/ml. In some embodiments, the low molecular weight polymer is present in a concentration from 0.1 mg/ml to 50 mg/ml. In some embodiments, the low molecular weight polymer is present in a concentration from 0.1 mg/mi to 5 mg/ml. In some embodiments, the low molecular weight polymer compound is present in a concentration from 5 mg/ml to 10 mg/ml. In some embodiments, the low molecular weight polymer is present in a concentration from 10 mg/ml to 20 mg/ml. In some embodiments, the low molecular weight polymer is present in a concentration from 20 mg/ml to 30 mg/ml. In some embodiments, the low molecular weight polymer is present in a concentration from 30 mg/ml to 50 mg/ml. In some embodiments, the low molecular weight polymer is present in a concentration from 50 mg/ml to 60 mg/ml. In some embodiments, the low molecular weight polymer is present in a concentration from 60 mg/ml to 80 mg/ml. In some embodiments, the low molecular weight polymer is present in a concentration from 80 mg/ml to 100 mg/ml.

The use of a stabilizer in pharmaceutical compositions is well known to the skilled person. For convenience, reference is made to Remington: The Science and Practice of Pharmacy. 19th edition, 1995.

In some embodiments, the formulation may comprise a surfactant where a surfactant can be a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g., Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate. N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g., 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g., lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g., N-alkyl-N,N-dimethylammonio-1-propanesulfonates. 3-cholamido-1-propyldimethylammonio-1-propanesulfonate, dodecylphosphocholine, myristoyl lysophosphatidylcholine, hen egg lysolecithin), cationic surfactants (quaternary ammonium bases) (e.g., cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g., sodium tauro-dihydrofusidate etc.), long-chain fatty acids and salts thereof C6-C12 (e.g., oleic acid and caprylic acid), acylcarnitines and derivatives, $N_\alpha$-acylated derivatives of lysine, arginine or histidine, or side-chain acylated derivatives of lysine or arginine, $N_\alpha$-acylated derivatives of dipeptide comprising any combination of lysine, arginine or histidine and a neutral or acidic amino acid, $N_\alpha$-acylated derivative of a tripeptide comprising any combination of a neutral amino acid and two charged amino acids, imidazoline derivatives, or any mixture thereof.

The use of a surfactant in pharmaceutical compositions is well-known to the skilled person. For convenience, reference is made to Remington: The Science and Practice of Pharmacy, 19th edition, 1995.

The formulations may also comprise a pharmaceutically acceptable sweetener. In some embodiments, the sweetener comprises at least one intense sweetener such as, but not limited to, saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, or from about 0.06% in the low-dosage formulations and about 0.08% in the high-dosage ones. The bulk sweetener can effectively be used in larger quantities ranging from about 10% to about 35% or from about 10% to 15% (w/v).

The formulations may be prepared by conventional techniques, for example, as described in Remington's Pharmaceutical Sciences, 1985 or in Remington: The Science and Practice of Pharmacy. 19th edition, 1995, where such conventional techniques of the pharmaceutical industry involve dissolving and mixing the ingredients as appropriate to give the desired end product.

Administration of the compound or the formulations described herein may be carried out using any method known in the art. For example, the administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, inhalation, or by oral administration. In some embodiments, the compound or formulation is administered intravenously or by injection.

For oral administration, the co-crystalline of any one of Form I-VII or the crystalline Form VIII or a therapeutically acceptable salt thereof can be formulated in unit dosage forms such as gel caps, caplets, granules, lozenges, bulk powders, capsules or tablets. The tablets or capsules may be prepared by conventional means with pharmaceutically acceptable excipients, including binding agents, for example, pregelatinized maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulfate. Tablets can be coated by methods well known in the art.

Liquid preparations for oral administration can take the form of, for example, solutions, syrups, or suspensions, or they can be presented as a dry product for constitution with water or other suitable vehicles before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For topical administration, any of the co-crystalline or crystalline forms provided or described herein, such as the co-crystalline Forms I-VII, the co-crystalline forms of the compound of Formula IV-I, and the crystalline Form VIII can be formulated in a pharmaceutically acceptable vehicle containing 0.1 to 10 percent, preferably 0.5 to 5 percent, of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, any crystalline form as described or provided herein, such as the co-crystalline forms of Form I-VII, the co-crystalline forms of the compound of Formula IV-I, and the crystalline Form VIII can be administered by either intravenous, subcutaneous, or intramuscular injection, in compositions with pharmaceutically acceptable vehicles or carriers. The crystalline form as described and provided herein can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Additionally, the compound can be precipitated and stored in an ampule or other container and then dissolved in a solution prior to being administered to a subject.

For administration by injection, the compound can be used in solution, and, for example, in a sterile aqueous vehicle which may also contain other solutes such as buffers or preservatives as well as sufficient quantities of pharmaceutically acceptable salts or of glucose to make the solution isotonic. In some embodiments, the pharmaceutical compositions may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's Pharmaceutical Sciences" by E. W. Martin.

For administration by inhalation, the compound may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration, the compound may be used, for example, as a liquid spray, as a powder or in the form of drops.

The compound can also be formulated in rectal compositions, for example, suppositories or retention enemas, for example, containing conventional suppository bases, for example, cocoa butter or other glycerides.

Furthermore, the compound can be formulated as a depot preparation. Such long-acting formulations can be administered by implantation (for example, subcutaneously or intramuscularly) or by intramuscular injection. Thus, for example, the compound can be formulated with suitable polymeric or hydrophobic materials (for example, as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack can also contain individual vials or other containers. The pack or dispenser device can be accompanied by instructions for administration.

Dosages

Any crystalline form as described or provided herein, such as the co-crystalline forms of Form I-VII, the co-crystalline forms of the compound of Formula IV-I, and the crystalline Form VIII may be administered to a patient at therapeutically effective doses to prevent, treat, or control diseases and disorders mediated, in whole or in part, by a GPCR-ligand interaction described herein. Pharmaceutical compositions comprising any crystalline form as described or provided herein, such as the co-crystalline forms of Form I-VII, the co-crystalline forms of the compound of Formula IV-I, and the crystalline Form VIII may be administered to a patient in an amount sufficient to elicit an effective protective or therapeutic response in the patient. The dose will be determined by the efficacy of the particular compound employed and the condition of the subject, as well as the bodyweight or surface area of the area to be treated. The size of the dose also will be determined by the existence, nature, and extent of any adverse effects that accompany the administration of a particular compound or vector in a particular subject.

The amount and frequency of administration of the compound comprising any crystalline form as described or provided herein, such as the co-crystalline forms of Form I-VII, the co-crystalline forms of the compound of Formula IV-I, and the crystalline Form VIII prepared according to a method described herein and/or the pharmaceutically acceptable salts thereof can be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general, it is contemplated that an effective amount would be from 0.001 mg/kg to 10 mg/kg body weight, and in particular from 0.01 mg/kg to 1 mg/kg body weight. More specifically, it is contemplated that an effective amount would be to continuously infuse by intravenous administration from 0.01 micrograms/kg body weight/min to 100 micrograms/kg body weight/min for a period of 12 hours to 14 days. It may be appropriate to administer the required dose as two, three, four or more sub-doses at appropriate intervals throughout the day. Sub-doses may be formulated as unit dosage forms, for example, containing 0.01 to 500 mg, and in particular 0.1 mg to 200 mg of active ingredient per unit dosage form.

In some embodiments, the pharmaceutical preparation is in a unit dosage form. In such form, the preparation is subdivided into suitably sized unit doses containing appropriate quantities of the active component. e.g., an effective amount to achieve the desired purpose. The quantity of active compound in a unit dose of preparation may be varied or adjusted from about 0.01 mg to about 1000 mg, from about 0.01 mg to about 750 mg, from about 0.01 mg to about 500 mg, or from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

Medical Use

A composition comprising a co-crystalline form of any crystalline form as described or provided herein, such as the co-crystalline forms of Form I-VII, the co-crystalline forms of the compound of Formula IV-I, and the crystalline Form VIII prepared according to a method described herein can be used for treating or preventing a variety of an alcohol-related disorder, such as alcohol use disorder, alcohol-induced disorder, alcohol abuse, alcohol dependence, alcohol intoxication, alcohol withdrawal, and the like. In some embodiments, the alcohol-related disorder is alcohol use disorder. In some embodiments, the alcohol-related disorder is an alcohol-induced disorder. In some embodiments, the alcohol-related disorder is alcohol abuse. In some embodiments, the alcohol-related disorder is alcohol dependence. In some embodiments, the alcohol-related disorder is alcohol intoxication. In some embodiments, the alcohol-related disorder is alcohol withdrawal.

A composition comprising one or more crystalline forms as described or provided herein, such as the co-crystalline forms of Form I-VII, the co-crystalline forms of the compound of Formula IV-I, and the crystalline Form VIII can be used for treating or preventing a variety of an alcohol-related disorder, such as alcohol use disorder, alcohol-induced disorder, alcohol abuse, alcohol dependence, alcohol intoxication, alcohol withdrawal, and the like. In some embodiments, the alcohol-related disorder is alcohol use disorder. In some embodiments, the alcohol-related disorder is an alcohol-induced disorder. In some embodiments, the alcohol-related disorder is alcohol abuse. In some embodiments, the alcohol-related disorder is alcohol dependence. In some embodiments, the alcohol-related disorder is alcohol intoxication. In some embodiments, the alcohol-related disorder is alcohol withdrawal.

In some embodiments, provided are compositions comprising one or more crystalline forms as described or provided herein, such as the co-crystalline forms of Form I-VII, the co-crystalline forms of the compound of Formula IV-I, and the crystalline Form VIII can be used for treating a variety of an alcohol-related disorder, such as alcohol use disorder, alcohol-induced disorder, alcohol abuse, alcohol dependence, alcohol intoxication, alcohol withdrawal, and the like. In some embodiments, the alcohol-related disorder is alcohol use disorder. In some embodiments, the alcohol-related disorder is an alcohol-induced disorder. In some embodiments, the alcohol-related disorder is alcohol abuse. In some embodiments, the alcohol-related disorder is alcohol dependence. In some embodiments, the alcohol-related disorder is alcohol intoxication. In some embodiments, the alcohol-related disorder is alcohol withdrawal.

In some embodiments, provided are compositions comprising one or more crystalline forms as described or provided herein, such as the co-crystalline forms of Form I-VII, the co-crystalline forms of the compound of Formula IV-I, and the crystalline Form VIII can be used for preventing a variety of an alcohol-related disorder, such as alcohol use disorder, alcohol-induced disorder, alcohol abuse, alcohol dependence, alcohol intoxication, alcohol withdrawal, and the like. In some embodiments, the alcohol-related disorder is alcohol use disorder. In some embodiments, the alcohol-related disorder is an alcohol-induced disorder. In some embodiments, the alcohol-related disorder is alcohol abuse. In some embodiments, the alcohol-related disorder is alcohol dependence. In some embodiments, the alcohol-related disorder is alcohol intoxication. In some embodiments, the alcohol-related disorder is alcohol withdrawal.

In some embodiments, the subject is diagnosed with the alcohol-related disorder.

In some embodiments, methods of reducing the amount of alcohol consumed are provided by a subject is provided. In some embodiments, the subject is diagnosed with, suffers from, or is suspected of having an alcohol-related disorder, such as alcohol use disorder. In some embodiments, the method comprises administering a pharmaceutical composition comprising a compound, a crystalline form, or a co-crystalline form provided for herein. In some embodiments, the subject is found to drink less or no alcohol over a 90 day period as compared a 90 day period of time prior to being treated with the pharmaceutical composition.

In some embodiments, methods of reducing alcoholic cravings in a subject with alcohol use disorder are provided. In some embodiments, the method comprises administering a pharmaceutical composition comprising a compound, a crystalline form, or a co-crystalline form provided for herein. In some embodiments, the subject is found to have a reduction in cravings as measured on the Visual Analogue Scale of Craving. The Visual Analogue Scale of Craving has 4 questions to assess domains of alcohol craving: the intention to drink, loss of control, relief craving, and urge intensity with a 0-20 point visual analog scale for each item, with 0 indicating no craving and 20 indicating severe craving. In some embodiments, the subject has a reduction in the craving scale after 2 weeks of being treated with the pharmaceutical composition. In some embodiments, the reductions in craving occur after 3, 4, 5, 6, 7, 8, 9, 10, 11, 12, or 13 weeks. In some embodiments, the reduction on the scale is about, or at least, 5, 10, 15, 20, 30, 40, 50, 60, 70, or 75 points.

In some embodiments, methods of reducing drinking alcohol are provided. In some embodiments, the method comprises administering a pharmaceutical composition comprising a compound, a crystalline form, or a co-crystalline form provided for herein. In some embodiments, the reduction of consuming alcohol is provided, wherein the number of drinks consumed in a natural environment over a period of time is measured and compared to the same period of time during treatment. In some embodiments, the period of time is 1-14 days before and after treatment is provided. In some embodiments, the information is obtained during a timeline follow-back interview.

In some embodiments, methods of increasing the percentage of no heavy drinking days for a subject with alcohol use disorder are provided. In some embodiments, the method comprises administering a pharmaceutical composition comprising a compound, a crystalline form, or a co-crystalline form provided for herein. In some embodiments, the percentage of no heavy drinking days is increased by at least, or about, 5, 10, 15, 20, 30, 40, 50, 60 70, 80, 90, 100, 200, or 300%. In some embodiments, the time period measured is 1, 2, 3, 4, 5, 6, 7, 8, 9, 10, 11, 12, 13, or more weeks. In some embodiments, the period of time is 26 or more weeks. As used herein, the term "heavy drinking day" is defined as more than 3 drinks per day for women and more than 4 drinks per day for men.

Combination Therapies

Methods are also provided for treating or preventing a variety of an alcohol-related disorder, such as alcohol use disorder, alcohol-induced disorder, alcohol abuse, alcohol dependence, alcohol intoxication, alcohol withdrawal, and the like by administering one or more crystalline forms as described or provided herein, such as the co-crystalline forms of Form I-VII, the co-crystalline forms of the compound of Formula IV-I, and the crystalline Form V III prepared according to a method described herein, and/or pharmaceutically acceptable salts thereof, in combination with other drugs for the treatment of a variety of an alcohol-related disorder, such as alcohol use disorder, alcohol-induced disorder, alcohol abuse, alcohol dependence, alcohol intoxication, alcohol withdrawal, and the like. In some embodiments, the alcohol-related disorder is alcohol use disorder. In some embodiments, the alcohol-related disorder is an alcohol-induced disorder. In some embodiments, the alcohol-related disorder is alcohol abuse. In some embodiments, the alcohol-related disorder is alcohol dependence. In some embodiments, the alcohol-related disorder is alcohol intoxication. In some embodiments, the alcohol-related disorder is alcohol withdrawal.

In the combination therapies, one or more crystalline forms as described or provided herein, such as the co-crystalline forms of Form I-VII, the co-crystalline forms of the compound of Formula IV-I. and the crystalline Form VIII is co-administered with one or more drugs for the treatment of a variety of an alcohol-related disorder, such as alcohol use disorder, alcohol-induced disorder, alcohol abuse, alcohol dependence, alcohol intoxication, alcohol withdrawal, and the like to increase efficacy and to reduce side effects associated with high doses of these therapeutics.

The combination therapies described above have synergistic and additive therapeutic effects. An improvement in the drug therapeutic regimen can be described as the interaction of two or more agents so that their combined effect reduces the incidence of adverse event (AE) of either or both agents used in co-therapy. This reduction in the incidence of adverse effects can be a result of, e.g., the administration of lower dosages of either or both agents used in the co-therapy. For example, if the effect of Drug A alone is 25% and has an adverse event incidence of 45% at labeled dose; and the effect of Drug B alone is 25% and has an adverse event incidence of 30% at labeled dose, but when the two drugs are combined at lower than labeled doses of each, if the overall effect is 35% (an improvement, but not synergistic or additive) and the adverse incidence rate is 20%, there is an improvement in the drug therapeutic regimen.

In some embodiments, the compounds described herein are administered as a mono-therapy. In some embodiments, the compounds described herein are administered as part of a combination therapy. For example, a compound may be used in combination with other drugs or therapies that are used in the treatment/prevention/suppression and/or amelioration of the diseases or conditions for which compounds are useful.

Such other drug(s) may be administered by a route and in an amount commonly used therefore, contemporaneously or sequentially with the compounds described herein. When a compound described herein is used contemporaneously with one or more other drugs, a pharmaceutical unit dosage form containing such other drugs in addition to the compound described herein may be employed. Accordingly, the pharmaceutical compositions include those that also contain one or more other active ingredients, in addition to the compounds described herein.

A subject or patient in whom an administration of a therapeutic compound is an effective therapeutic regimen for a disease or disorder is often a human but can be any animal, including a laboratory animal in the context of a clinical trial or screening or activity experiment. Thus, as can be readily appreciated by one of ordinary skill in the art, the methods, compound and compositions are particularly suited to administration to any animal, such as a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are merely illustrative and should not be construed as limiting the scope of the embodiments in any way as many variations and equivalents that are encompassed by these embodiments will become apparent to those skilled in the art upon reading the present disclosure.

In some embodiments, the subject is diagnosed with the alcohol-related disorder.

EXAMPLES

Example 1

Co-Crystal Screening: Grinding Experiments of the Compound of Formula I

The co-crystal screening of the compound of Formula I with coformer was carried out through a dry grinding procedure. An equimolar mixture of the compound of Formula I, Formula I-a, or Formula I-b with a coformer was ground in a RETSCH Mixer Mill MM 400 (+/−22.8 mg of the compound of Formula I) for 30 min with a beating frequency of 30 Hz and using stainless steel grinding beads. The resulting powders were characterized using X-ray Powder Diffraction.

Coformer tested. A list of co-crystal formers ("coformer") was tested as shown in Table 1. Coformer were chosen from the list of most common co-crystal formers, including but not limited to the coformer described in Pharmaceutical Salts and Co-crystals, Johan Wouters and Luc Quéré, RSC publishing, 2011.

TABLE 1

| Coformer | CAS No. | co-crystal |
|---|---|---|
| ORGANIC ACID AND BASES | | |
| 1-hydroxy-2-naphtoic acid | 86-48-6 | No |
| (S)-2-pyrrolidone-5-carboxylic acid | 98-79-3 | No |
| 2,3-dihydroxybenzoic acid | 303-38-8 | No |
| 2,4-dihydroxybenzoic acid | 89-86-1 | No |
| 2,5-dihydroxybenzoic acid (gentisic) | 490-79-9 | No |
| 3,4-dihydroxybenzoic acid | 99-50-3 | No |
| 3,5-dihydroxybenzoic acid | 99-10-5 | YES |
| 4-hydroxybenzoic acid | 99-96-7 | No |
| 4-aminobenzoic acid | 150-13-0 | amorphous |
| 4-dimethylaminobenzoic acid | 619-84-1 | No |
| 4-hydroxy-3-methoxycinnamic acid (Ferulic) | 1135-24-6 | No |
| acetylsalicylic acid | 50-78-2 | No |
| (D)-aspartic acid | 1783-96-6 | No |
| (L)-aspartic acid | 556-84-8 | No |
| (DL)-aspartic acid | 617-45-8 | No |
| Caffeine | 58-08-2 | No |
| (D)-(+)-camphoric acid | 124-83-4 | |
| Citric acid | 77-92-9 | No |
| fumaric acid | 110-17-8 | No |
| (S)-Ibuprofen | 51146-56-6 | amorphous |
| (RS)-Ibuprofen | 15687-27-1 | No |
| indole-3-acetic acid | 87-51-4 | amorphous |
| (D)-malic acid | 636-61-3 | amorphous |
| (L)-malic acid | 97-67-6 | amorphous |
| maleic acid | 110-16-7 | amorphous |
| malonic acid | 141-82-2 | amorphous |
| (R)-mandelic acid | 611-71-2 | amorphous |
| (S)-mandelic acid | 17199-29-0 | amorphous |
| (DL)-mandelic acid | 90-64-2 | amorphous |
| oxalic acid | 144-62-7 | |
| salicylic acid | 69-72-7 | No |
| succinic acid | 110-15-6 | No |
| (D)-tartaric acid | 147-71-7 | No |
| (L)-tartaric acid | 87-69-4 | No |
| (DL)-tartaric acid | 133-37-9 | No |
| vanillin | 121-33-5 | amorphous |
| Acetaminophen (paracetamol) | 103-90-2 | amorphous |
| Theophylline | 58-55-9 | No |
| S-Methyl-L-cysteine | 1187-84-4 | No |
| (S)-naproxen | 22204-53-1 | No |
| (S)-Ketoprofen | 22161-81-5 | amorphous |
| adipic acid | 0124-04-09 | No |
| glycolic acid | 79-14-1 | amorphous |
| Benzoic Acid | 65-85-0 | No |
| p-coumaric acid | 501-98-4 | No |
| 3-hydroxybenzoic acid | 99-06-9 | No |
| Sorbic acid | 110-44-1 | No |
| o-benzoic sulfuimide (Saccharine) | 81-07-2 | No |

TABLE 1-continued

| Coformer | CAS No. | co-crystal |
|---|---|---|
| 1,3,5-benzenetricarboxylic acid (Trimesic Acid) | 554-95-0 | Yes |
| 3,4,5-trihydroxybenzoic acid (Gallic acid) | 149-91-7 | No |
| ellagic acid hydrate | 476-66-4 | YES |
| xanthine | 69-89-6 | No |
| Sulfathiazole | 72-14-0 | No |
| methyl 3,4,5-trihydroxybenzoate | 99-24-1 | No |
| glutaric acid | 110-94-1 | No |
| Methyl 3,4,5 trimethoxybenzoate | 1916-07-0 | No |
| Gallic acid ethyl ester (ethyl gallate) | 831-61-8 | No |
| Methyl 4-hydroxybenzoate | 99-76-3 | amorphous |
| 2-ethoxybenzamide | 938-73-8 | No |
| Primidone | 125-33-7 | No |
| Benzenesulfonic acid | 98-11-3 | reaction |
| meso-Erythritol | 149-32-6 | No |
| 2-aminobenzoic acid | 118-92-3 | No |
| Stearic acid | 57-11-4 | No |
| (L)-Ascorbic acid (vitamin C) | 50-81-7 | No |
| Nicotinic acid | 59-67-6 | No |
| L-Pyroglutamic acid | 98-79-3 | No |
| trans-Cinnamic acid | 0140-10-3 | No |
| Pamoic acid | 130-85-8 | No |
| 3-Ethoxy-4-hydroxybenzaldehyde (Ethylvanillin) | 121-32-4 | No |
| 3-Hydroxy-2-methyl-4-pyrone (Maltol) | 118-71-8 | No |
| 2-Mercapto-1-methylimidazole (Thiamazole) | 60-56-0 | No |
| Erythorbic acid (stereoisomer L-ascorbic acid) | 89-65-6 | No |
| cholic acid | 81-25-4 | No |
| Pimelic acid | 111-16-0 | No |
| Suberic acid | 505-48-6 | No |
| Praziquantel | 55268-74-1 | No |
| AMINO ACIDS | | |
| Glycine | 56-40-6 | No |
| Cysteine (L) | 52-90-4 | No |
| Glutamine (L) | 56-85-9 | No |
| Histidine (L) | 71-00-1 | No |
| Serine (L) | 56-45-1 | No |
| Threonine (L) | 72-19-5 | No |
| Tryptophan (L) | 73-22-3 | No |
| Tyrosine (L) | 60-18-4 | No |
| Proline (L) | 147-85-3 | |
| Valine (L) | 72-18-4 | No |
| Alanine (L) | 56-41-7 | No |
| Leucine (L) | 61-90-5 | No |
| Phenylalanine (L) | 63-91-2 | No |
| Isoleucine (L) | 73-32-5 | No |
| Lysine (L) | 56-87-1 | amorphous |
| Methionine (L) | 63-68-3 | |
| Arginine (L) | 74-79-3 | No |
| Asparagine (L) | 70-47-3 | No |
| Aspartic acid (L) | 56-84-8 | No |
| Glutamic acid (L) | 56-86-0 | No |
| 4-aminomethylbenzoic acid | 150-13-0 | No |
| ORGANIC AMIDES | | |
| carbamazepine | 298-46-4 | No |
| isonicotinamide | 1453-82-3 | No |
| urea | 57-13-6 | YES |
| nicotinamide | 98-92-0 | No |
| Oxcarbazepine | 28721-07-05 | No |
| 4-Aminobenzamide | 2835-68-9 | No |
| 3-Aminobenzamide | 3544-24-9 | amorphous |
| Salicylamide | 65-45-2 | No |
| Benzamide | 55-21-0 | No |
| Pyrazinamide | 98-96-4 | No |
| RACETAM | | |
| Piracetam | 7491-74-9 | No |
| ORGANIC AMINES | | |
| L-Penicillamine | 1113-41-3 | No |
| ORGANIC ALCOHOL/PHENOL | | |
| Quercetin | 117-39-5 | No |
| Rutin hydrate | 207671-50-9 | No |

TABLE 1-continued

| Coformer | CAS No. | co-crystal |
|---|---|---|
| (−)-Epicatechin | 490-46-0 | No |
| (+)-catechin hydrate | 225937-10-0 | amorphous |
| OSES | | |
| sucrose D(+) | 57-50-1 | No |
| Fructose D(−) | 57-48-7 | No |
| isomannide | 641-74-7 | amorphous |
| D-Isosorbide | 652-67-5 | amorphous |
| D-Sorbitol | 50-70-4 | No |
| D-Mannitol | 69-65-8 | No |
| aspartame | 22839-47-0 | No |
| D-(+)-glucose anhydrous | 50-99-7 | No |
| ORGANIC AND INORGANIC SALTS | | |
| Calcium chloride anhydrous | 10043-52-4 | YES |
| Magnesium chloride anhydrous | 7786-30-3 | YES |
| Sodium chloride | 7647-14-5 | No |
| Zinc chloride | 7646-85-7 | No |
| boric acid | 10043-35-3 | No |
| VITAMIN | | |
| D-biotin | 58-85-5 | No |

Example 2A

Co-Crystal Screening for the Compound of Formula I and Urea

Figure 8:
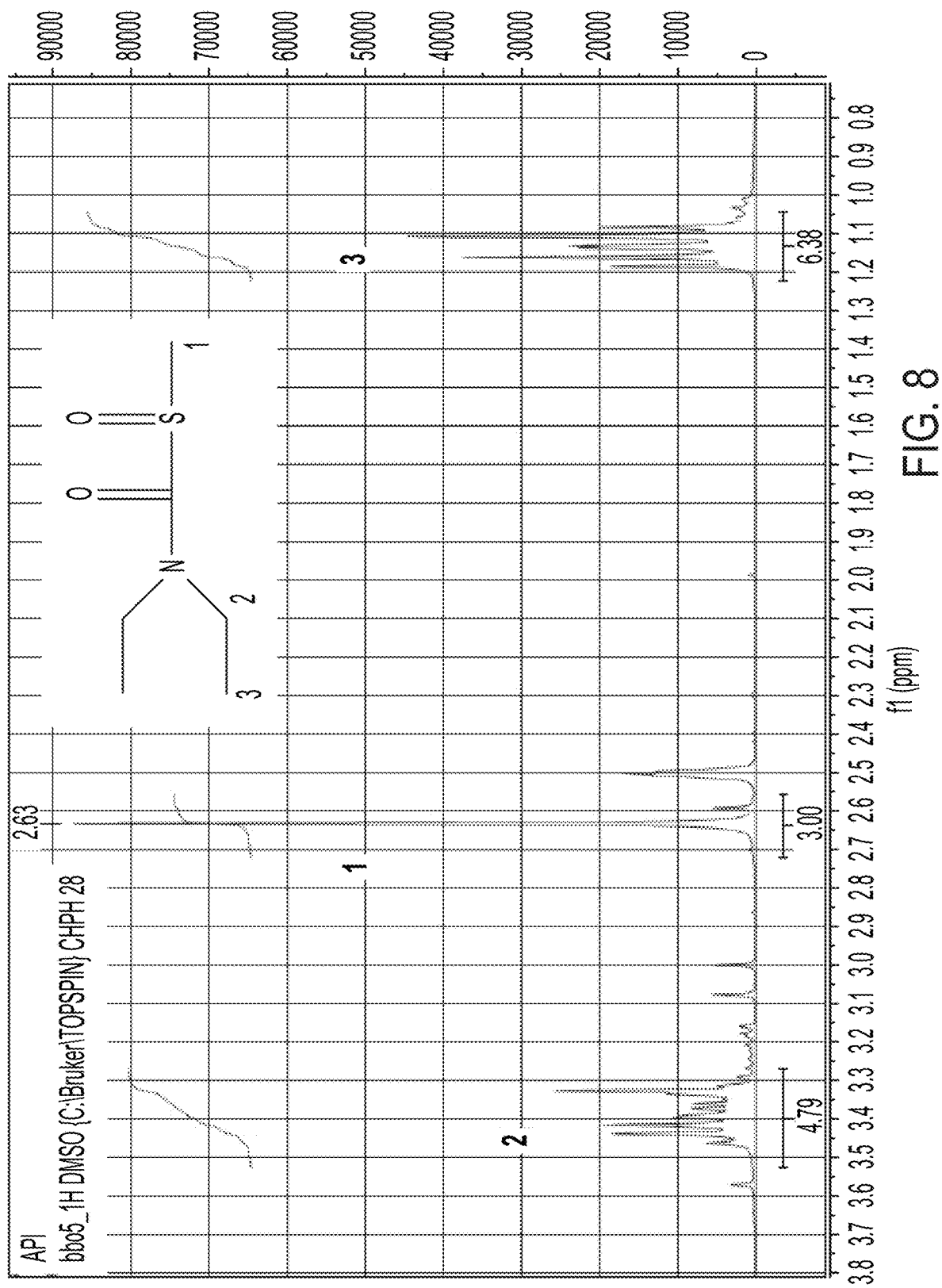
FIG. 8 shows Proton Nuclear Magnetic Resonance Spectroscopy ($^1$H NMR) analysis of the compound of Formula I.

To prepare the co-crystal of the compound of Formula I and urea, various slurrying experiments were performed as shown in Table 1. A typical experiment comprises adding solvent and starting materials to a vial, equipped with a stirring bar. Vials are then left to stir for 48 h at room temperature. The slurries are filtered and the recovered solid is washed with pure solvent or not washed. The NMR of the compound of Formula I (FIG. 8) shows a distinct peak of the SO—CH$_3$ group at 2.63 ppm. To determine the ratio of urea to the compound of Formula I, the NMR signal at 5.4 ppm (N—H of urea) and at 2.63 ppm (the SO—CH$_3$ group of DETC-Meso) are used. Table 2 provides the details and results regarding the slurrying experiments.

TABLE 2

| Molar Ratio of Urea to API | Solvent (1 mL) | Urea (mg) | API (μL) | XRPD of the recovered solid | Molar Ratio of urea to API in the recovered solid by NMR | Washed |
|---|---|---|---|---|---|---|
| 5:1 | ACN | 334.23 | 160 | Urea | Urea only | YES |
| 3:1 | ACN | 275.15 | 220 | Urea + traces FI | Urea only | YES |
| 1:1 | ACN | 133.94 | 320 | Urea + traces FI | Urea only | YES |
| 1:3 | ACN | 58.60 | 420 | Urea + FI | 6.5 | |
| 5:1 | Tol | 334.20 | 160 | Urea + traces FI | 10 | YES |
| 3:1 | Tol | 275.36 | 220 | Urea + traces FI | 7.6 | YES |
| 1:1 | Tol | 133.62 | 320 | FI + traces urea | 1.76 | YES |
| 1:2 | Tol (2 ml) | 78 | 370 | FI | 1.00 | NO |
| 1:3 | Tol | 58.85 | 420 | FI | 0.94 | YES |
| 1:1 | Cyd (2 ml) | 39 | 370 | FI | | NO |
| 1:2 | Cyd (2 ml) | 78 | 370 | FI | 0.73 | NO |
| 5:1 | EtOAc | 334.1 | 160 | Urea + traces FI | 10.2 | YES |
| 3:1 | EtOAc | 275.18 | 220 | Urea + FI | 4.7 | YES |
| 1:1 | EtOAc | 133.76 | 320 | FI + Urea | 2.13 | YES |
| 1:1 | EtOAc | | | FI + Urea | 2.17 | NO |
| 1:2 | EtOAc (2 ml) | 78 | 370 | FI + Urea | 0.96 | NO |

TABLE 2-continued

| Molar Ratio of Urea to API | Solvent (1 mL) | Urea (mg) | API (µL) | XRPD of the recovered solid | Molar Ratio of urea to API in the recovered solid by NMR | Washed |
|---|---|---|---|---|---|---|
| 1:3 | EtOAc | 58.44 | 420 | FI | 1.01 | YES |
| 1:3 | EtOAc (2.5 ml) | 292.2 | 2100 | FI | 1.03 | NO |
| 5:1 | MeOH | 334.13 | 160 | Urea | Urea only | YES |
| 3:1 | MeOH | 275.39 | 220 | Urea | | YES |
| 1:1 | MeOH | 132.85 | 320 | | | |
| 1:3 | MeOH | 58.53 | 420 | | | |

API; the compound of the Formal I
FI: the co-crystalline Form I of the compound of the Formula I and urea
Ratio: the molar ratio of urea to API Methanol is not a suitable solvent for co-crystallization since slurrying the mixtures of the compound of Formula I and urea at 5:1 and 3:1 molar ratios in methanol led to pure urea coming out, while slurrying the mixtures of urea to the compound of Formula I at 1:1 and 1:3 molar ratios resulted in full dissolution.

Acetonitrile is also not a suitable solvent for co-crystallization since slurrying the mixtures of the compound of Formula I and urea at 5:1 molar ratios in acetonitrile led to pure urea coming out, whereas slurrying the mixtures of the compound of Formula I and urea at 3:1 and 1:1 ratio showed traces of co-crystal, but the amount of the co-crystal is so low that the compound of Formula I in NMR is lost in the background. This already highlights the difficulty in XRPD interpretation, as the peaks of the co-crystal are likely much more diffracting than urea, rendering it difficult to use XRPD to see excessive amounts of urea. Slurrying the mixtures of the compound of Formula I and urea at 1:3 ratio led to the crystallization of the co-crystal together with urea, with an overall number of 6 urea equivalents. The amount of urea is therefore in much excess with respect to the co-crystal.

In toluene, traces of the co-crystal form are found when using a mixture of the compound of Formula I and urea at a 5:1 molar ratio for slurrying. The amount of the co-crystal form clearly increased when using a 3:1 molar ratio of the compound of Formula I and urea, and a very small amount of urea was found when using a 1:1 molar ratio of the compound of Formula I and urea according to XRPD data. Both characteristic peaks of urea at 2θ=22.4 and 24.8 are however still present (albeit with low intensity). For the slurries with 1:2 and 1:3 molar ratios, these peaks are completely gone. Furthermore, the material obtained is very crystalline. This form is also found in all of the experiments as discussed above, and is hence named co-crystalline Form I.

Figure 13:
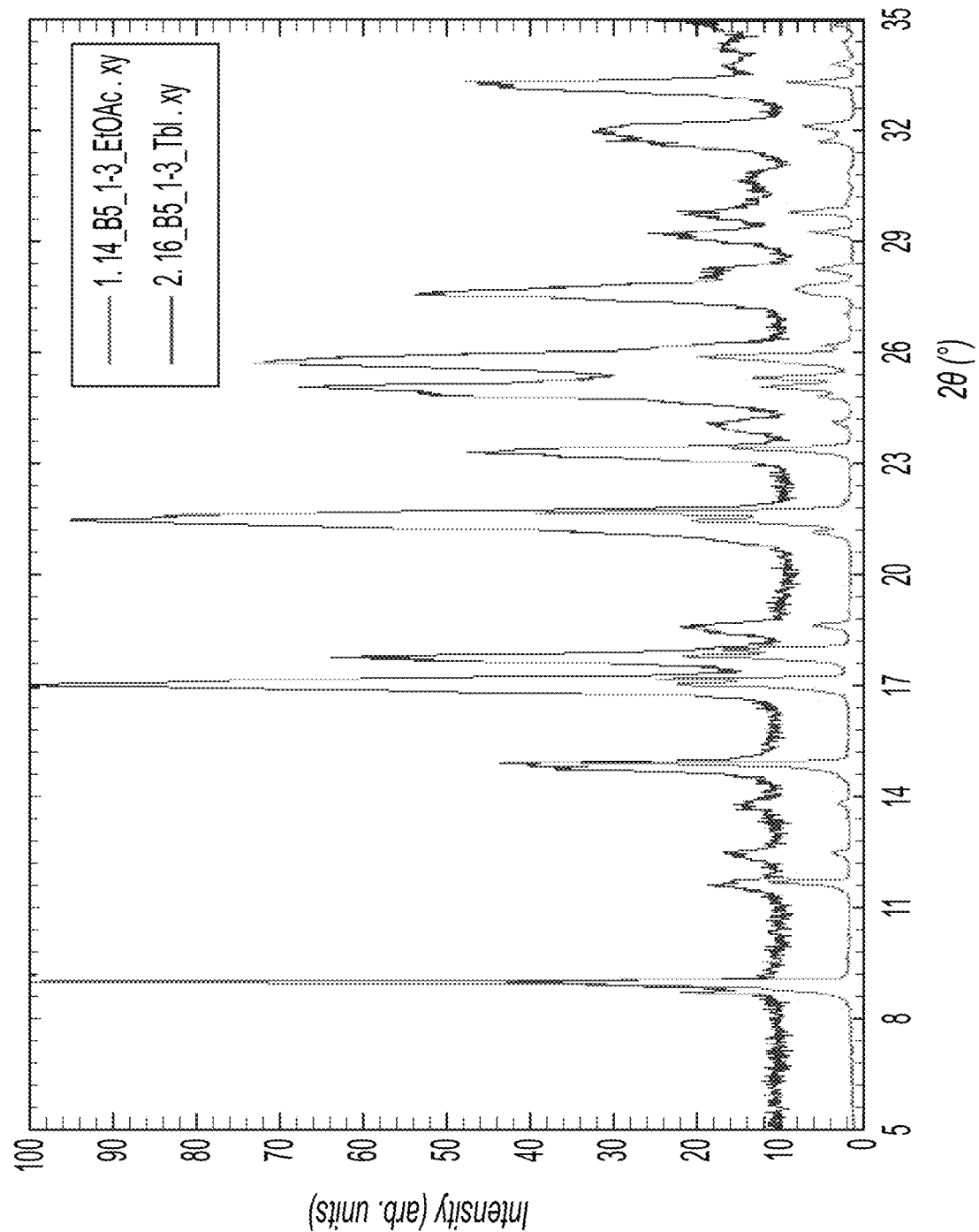
FIG. 13 shows the comparison of the XRPD patterns of the co-crystalline Form I prepared from the toluene (blue) and ethyl acetate (red).

The results using ethylacetate follow those observed when using toluene, with the slurries of the compound of Formula I and urea at 5:1, 3:1 and 1:1 molar ratios, respectively leading to mixtures of urea and co-crystal, with this latter present in the lesser amount the higher the ratio. The slurries of the compound of Formula I and urea at 1:2 and 1:3 molar ratios, led once again the co-crystalline Form I with the XRPD pattern consistent with that obtained from the 1:3 toluene slurry (FIG. 13).

Cyclohexane can be used as an alternative solvent for co-crystallization. Without washing with toluene and cyclohexane led to yellow powders (the compound of Formula I) adsorbed on the surface (also explaining the 0.73 ratio for the slurry of the compound of Formula I and urea at a 1:2 molar ratio). Unexpectedly and surprisingly, the use of ethyl acetate always leads to white crystals (even without washing).

Example 2B

Figure 17:
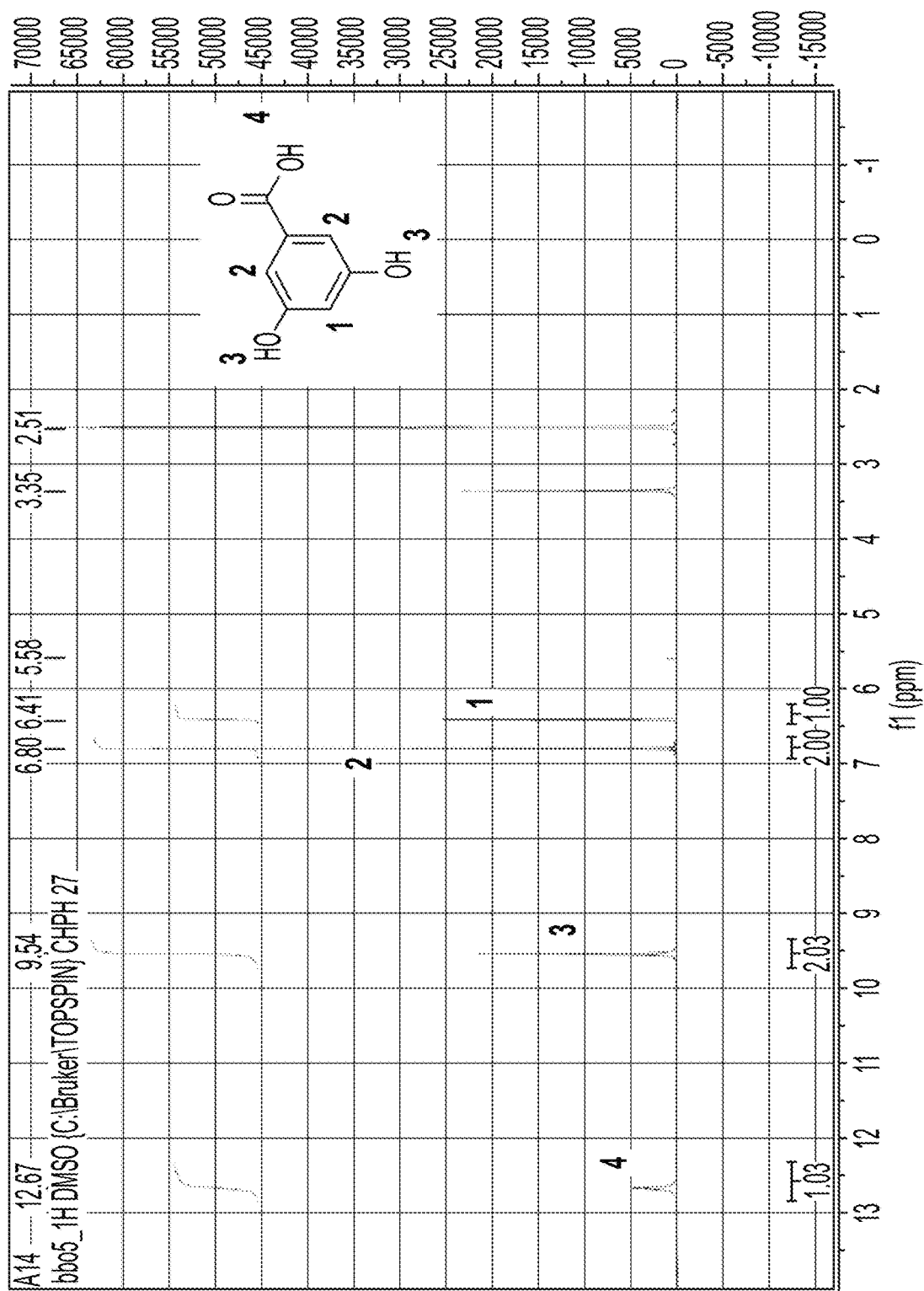
FIG. 17 shows Proton Nuclear Magnetic Resonance Spectroscopy ($^1$H NMR) analysis of 3,5-dihydroxybenzoic acid.

Co-Crystal Screening for the Compound of Formula I and 3,5-Dihydroxybenzoic Acid To prepare the co-crystal of the compound of Formula I and 3,5-dihydroxybenzoic acid, various slurrying experiments were performed as shown in Table 2. A typical experiment comprises adding solvent and starting materials to a vial, equipped with a stirring bar. Vials are then left to stir for 48 h at room temperature. The slurries are filtered and the recovered solid is washed with pure solvent or not washed. To determine the ratio of 3,5-dihydroxybenzoic acid to the compound of Formula I, the NMR signal at 6.8 ppm (2C—H of 3,5-DHB) (FIG. 17) and at 2.63 ppm (the SO—CH$_3$ group of DETC-Meso) are used. Table 3 provides the details and results regarding the slurrying experiments.

TABLE 3

| Ratio | Solvent (1 mL) | 3,5-DHB (mg) | API (µL) | XRPD of the recovered solid | Molar Ratio of 3,5-DHB to API in the recovered solid by NMR |
|---|---|---|---|---|---|
| 3:1 | ACN | 385.74 | 120 | 3,5-DHB | 14.7 |
| 1:1 | ACN | 246.34 | 230 | F3 | 1.8 |
| 1:3 | ACN | 128.63 | 360 | | |
| 3:1 | Tol | 385.67 | 120 | 3,5-DHB + F3 | 4.2 |
| 1:1 | Tol | 246.25 | 230 | F4 + F3 | 1.48 |
| 1:3 | Tol | 128.34 | 360 | F4 | 0.73 |
| 3:1 | EtOAc | 385.53 | 120 | F3 | 2.15 |
| 1:1 | EtOAc | 246.19 | 230 | F3 | 1.99 |
| 1:3 | EtOAc | 128.39 | 360 | | |

API; the compound of the Formal I
F3: the co-crystalline Form III of the compound of the Formula I and 3,5-dihydroxybenzoic acid
F4: the co-crystalline Form IV of the compound of the Formula I and 3,5-dihydroxybenzoic acid
Ratio: the molar ratio of urea to API Example 3

Preparation of the Co-Crystalline Form I of the Compound of Formula I and Urea

Co-crystalline Form I of the compound of Formula I and urea was obtained from slow evaporation using ethyl acetate as a solvent. 22.8 mg of the compound of Formula I and 16.8 mg of urea were added to a vial to which solvent was added to until complete dissolution to form a solution. The solution was then left to evaporate slowly at room temperature up to the apparition of the co-crystalline Form I. The single crystal was measured at a temperature of 150K. Single crystal X-ray diffraction was performed on a MAR345 detector using monochromatic Mo Kα radiation (×=0.71073 Å) produced by an Incoatec microfocus beam. FIG. 1 shows the X-ray powder diffraction pattern for the crystalline Form I. Peak positions are provided in Table 4.

TABLE 4

| Angle (2θ) | d value (Angstrom) |
|---|---|
| 9.00 | 9.83 |
| 11.69 | 7.57 |
| 14.91 | 5.94 |
| 17.03 | 5.21 |

TABLE 4-continued

| Angle (2θ) | d value (Angstrom) |
|---|---|
| 17.19 | 5.16 |
| 17.82 | 4.98 |
| 17.97 | 4.94 |
| 18.64 | 4.76 |
| 21.14 | 4.20 |
| 21.47 | 4.14 |
| 21.69 | 4.10 |
| 23.42 | 3.80 |
| 24.83 | 3.59 |
| 25.07 | 3.55 |
| 25.34 | 3.52 |
| 25.90 | 3.44 |
| 26.19 | 3.40 |
| 27.73 | 3.22 |
| 28.24 | 3.16 |
| 29.26 | 3.05 |
| 29.82 | 3.00 |
| 31.72 | 2.82 |
| 32.12 | 2.79 |
| 33.31 | 2.69 |

The data images were integrated by CrysAlisPRO and the implemented multiscan absorption was applied. The structure was solved with SHELXT and then refined on |F2| using SHELXL-2018/7 or SHELXL-2018/3. Non-hydrogen atoms were anisotropically refined. Hydrogen atoms were typically placed in the riding mode with isotropic temperature factors fixed at 1.2 times U (eq) of the parent atoms (1.5 times for methyl groups). Urea and the compound of Formula I co-crystallized together in a C2/C space group with a 1:1 ratio.

Figure 25:
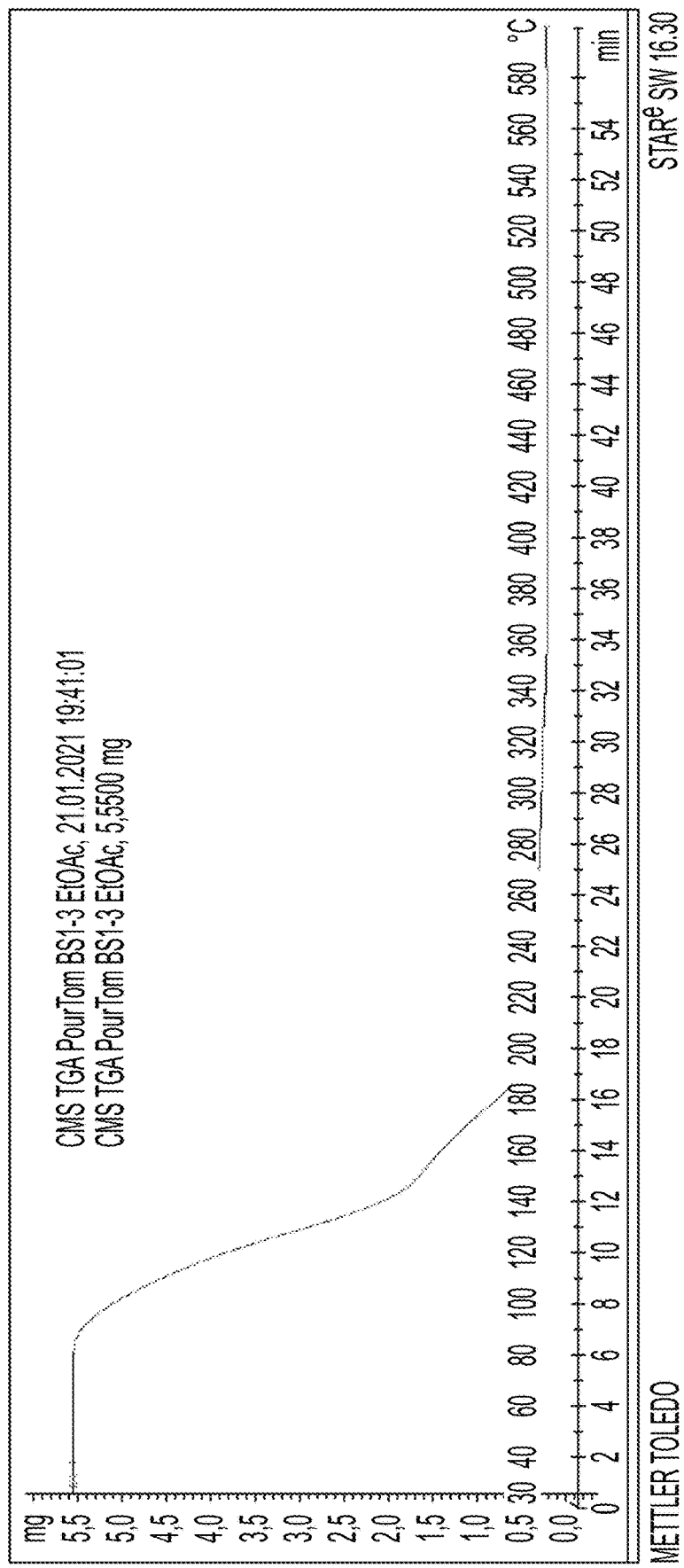
FIG. 25 shows TGA analysis of the crystalline Form I.

DSC analysis of this sample shows a melting onset at about 77° C. as shown in FIG. 16. TGA on the 1:3 sample shows degradation to start at 80° C. as shown in FIG. 25.

Grinding experiments were repeated for 3 times using the slurries of the compound of Formula I and urea at 1:2 and 1:3 molar ratios. All of the repeats led to the same crystalline form of the cocrystal, with the 1:2 and 1:3 experiments also showed the excess amount of urea.

Example 4

Figure 9:
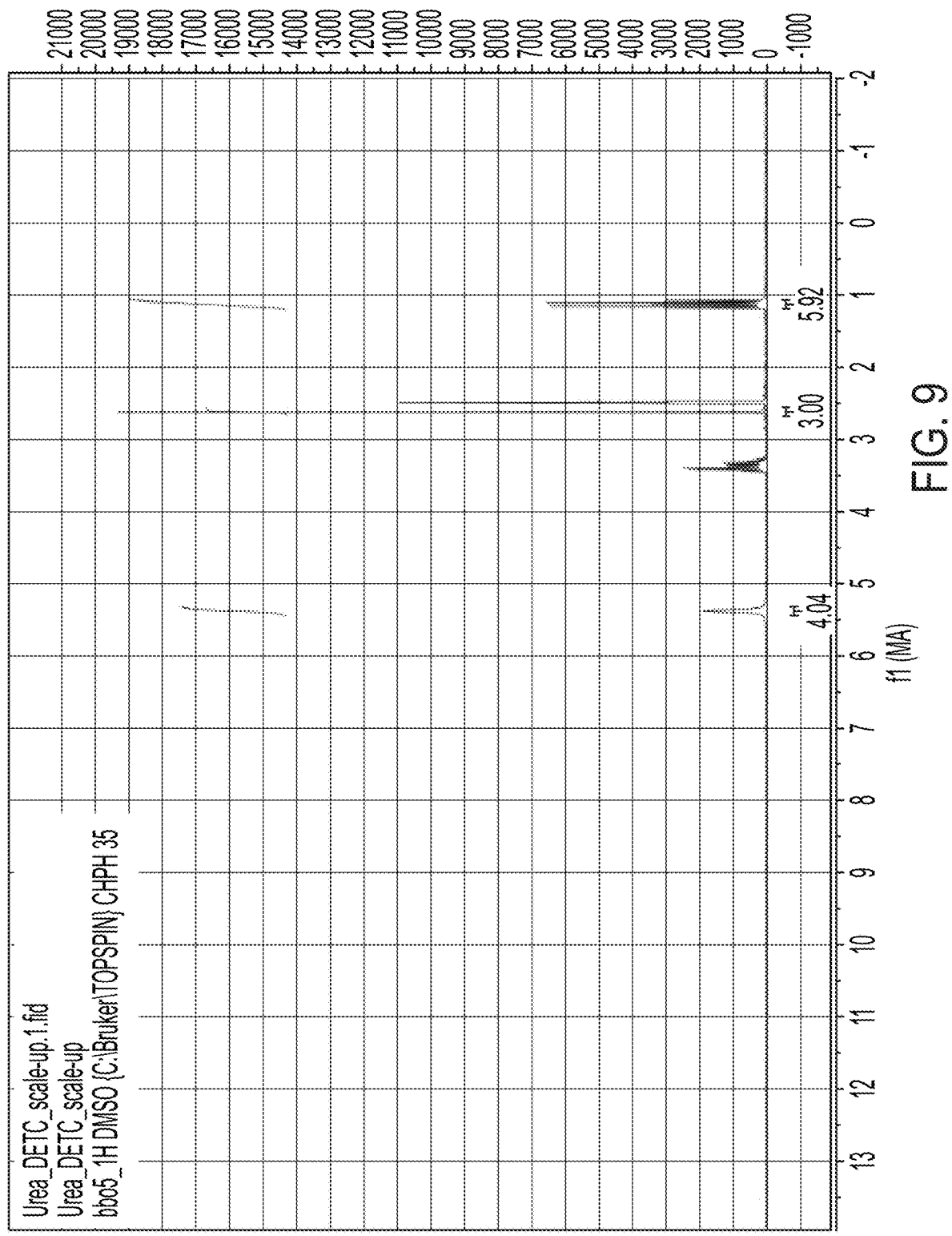
FIG. 9 shows Proton Nuclear Magnetic Resonance Spectroscopy ($^1$H NMR) analysis of the co-crystalline Form I.
Figure 10:
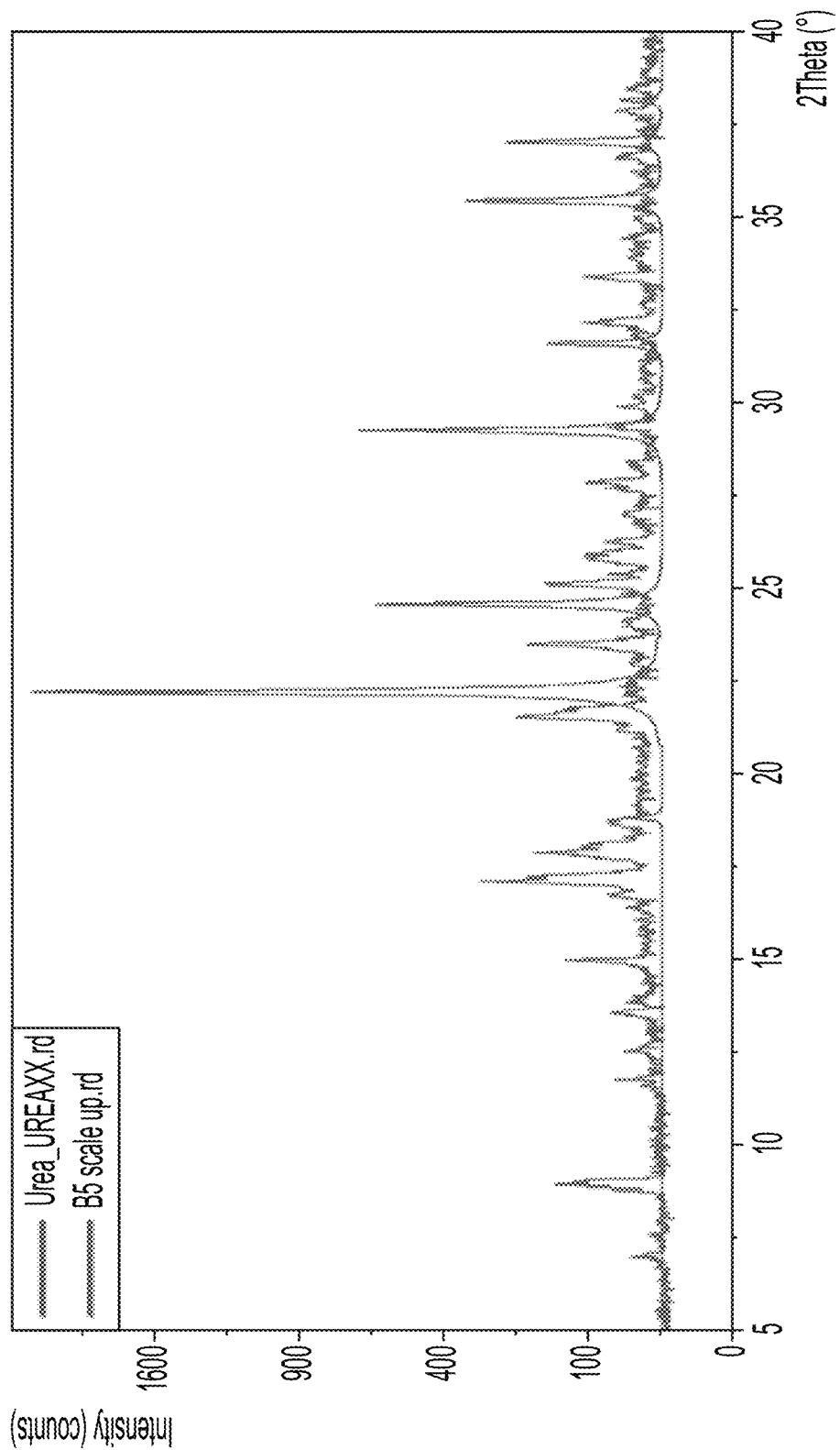
FIG. 10 shows the comparison of the XRPD pattern of the co-crystalline Form I (red) and urea (blue).

Preparation of the Co-Crystalline Form I of the Compound of Formula I and Urea on a Large Scale Co-crystalline Form I of the compound of Formula I and urea was obtained on large scale by using the following procedure. To 1 ml of ethyl acetate are added 58.44 mg of urea and 420 µl of the compound of Formula I to form a suspension. The suspension is left stirring for 48 h at room temperature to form a slurry. The slurry is then filtered to produce the co-crystalline Form I. To determine the ratio of urea to the compound of Formula I, the NMR signal at 5.4 ppm (N—H of urea) and at 2.63 ppm (the SO—CH$_3$ group of the compound of Formula I) are used. NMR shows a 1:1 co-crystal as shown in FIG. 9. The co-crystalline Form I shows a distinct XRPD spectrum compared to that of urea, as shown in FIG. 10.

Example 5

Preparation of the Co-Crystalline Form II of the Compound of Formula I and Trimesic Acid at a Ratio of 1:1

Figure 19:
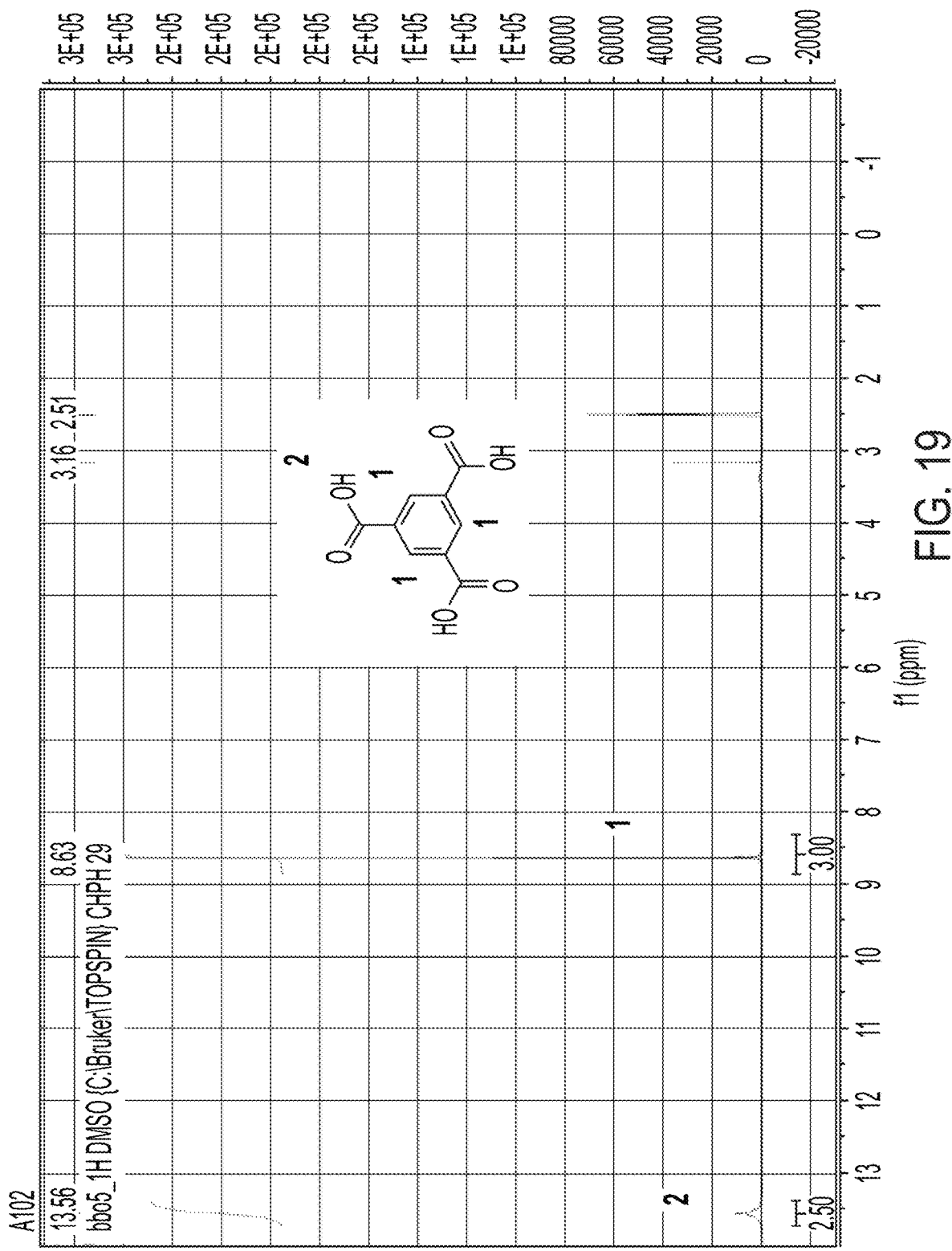
FIG. 19 shows Proton Nuclear Magnetic Resonance Spectroscopy ($^1$H NMR) analysis of trimesic acid.
Figure 20:
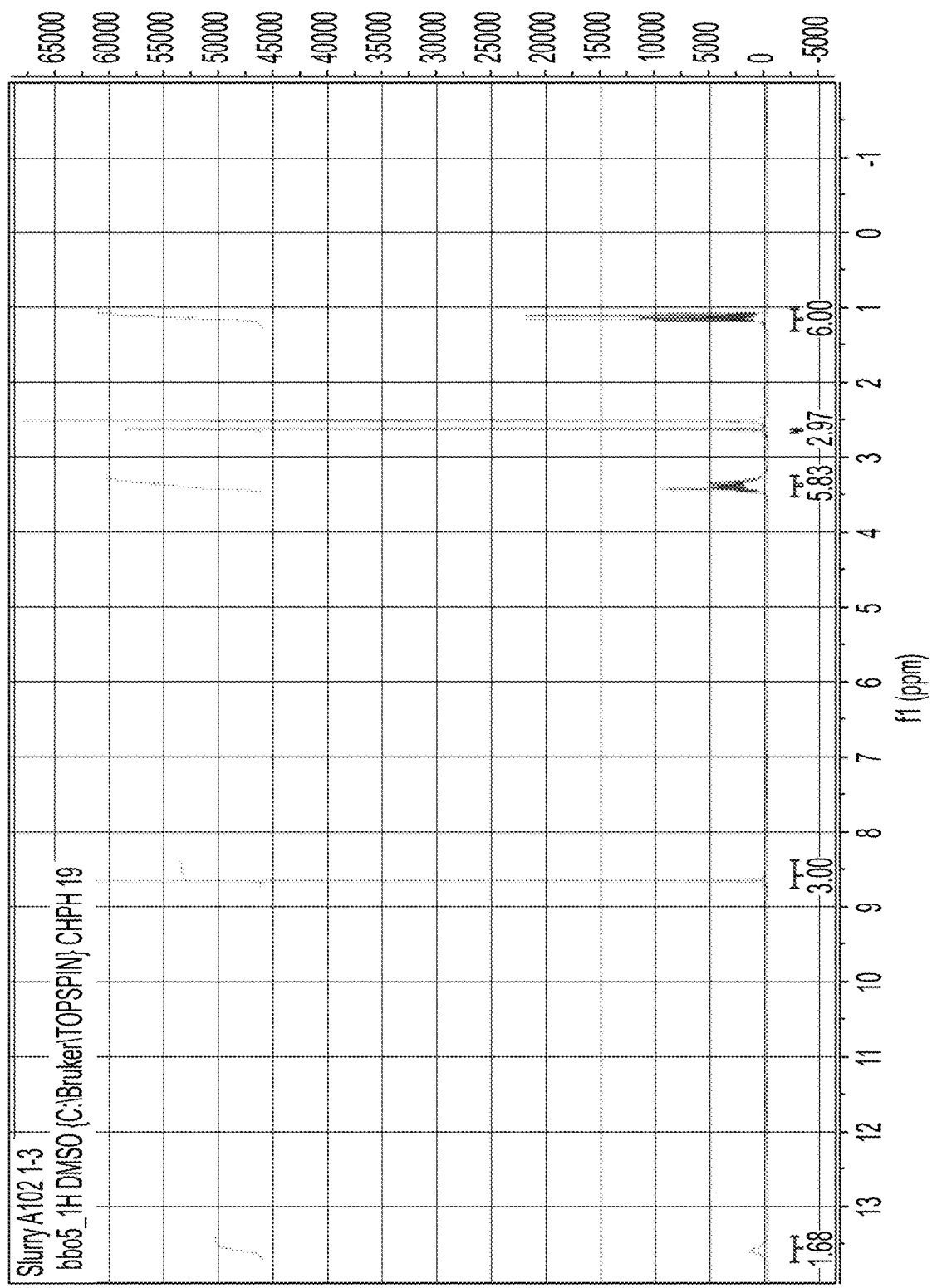
FIG. 20 shows Proton Nuclear Magnetic Resonance Spectroscopy ($^1$H NMR) analysis of the crystalline Form II.

Co-crystalline Form II of the compound of Formula I and trimesic acid were prepared with the following procedure. To 1 ml of ethyl acetate are added 146 mg of trimesic acid and 342 µl of the compound of Formula I to form a suspension. The suspension is left to stir for 48 h at room temperature to form a slurry. The slurry is filtered to produce the co-crystalline Form II. To determine the molar ratio of urea to the compound of Formula I, the NMR signal at 8.6 (trimesic acid) (FIG. 19) and at 2.63 ppm (the SO—CH$_3$ group of the compound of Formula I) are used. NMR shows a 1:1 molar ratio as shown in FIG. 20. FIG. 2 shows the X-ray powder diffraction pattern for the crystalline Form II. Peak positions are provided in Table 5.

TABLE 5

| Angle (2θ) | d value (Angstrom) |
|---|---|
| 5.33 | 16.57 |
| 7.60 | 11.64 |
| 9.11 | 9.71 |
| 10.67 | 8.29 |
| 11.97 | 7.39 |
| 14.21 | 6.23 |
| 14.49 | 6.11 |
| 15.20 | 5.83 |
| 15.69 | 5.65 |
| 16.77 | 5.29 |
| 17.06 | 5.20 |
| 17.24 | 5.14 |
| 17.64 | 5.03 |
| 17.81 | 4.98 |
| 18.31 | 4.84 |
| 18.41 | 4.82 |
| 18.72 | 4.74 |
| 19.45 | 4.56 |
| 19.97 | 4.45 |
| 20.96 | 4.24 |
| 22.06 | 4.03 |
| 22.32 | 3.98 |
| 23.02 | 3.86 |
| 23.25 | 3.83 |
| 24.02 | 3.71 |
| 24.35 | 3.65 |
| 25.38 | 3.51 |
| 25.99 | 3.43 |
| 26.55 | 3.36 |
| 27.08 | 3.29 |
| 27.34 | 3.26 |
| 27.63 | 3.23 |

DSC analysis of this sample shows an exothermic peak at about 103° C. as shown in FIG. 21.

Example 6

Preparation of the Co-Crystalline Form III of the Compound of Formula I and 3,5-Dihydroxybenzoic Acid at a Ratio of 1:2

Figure 18:
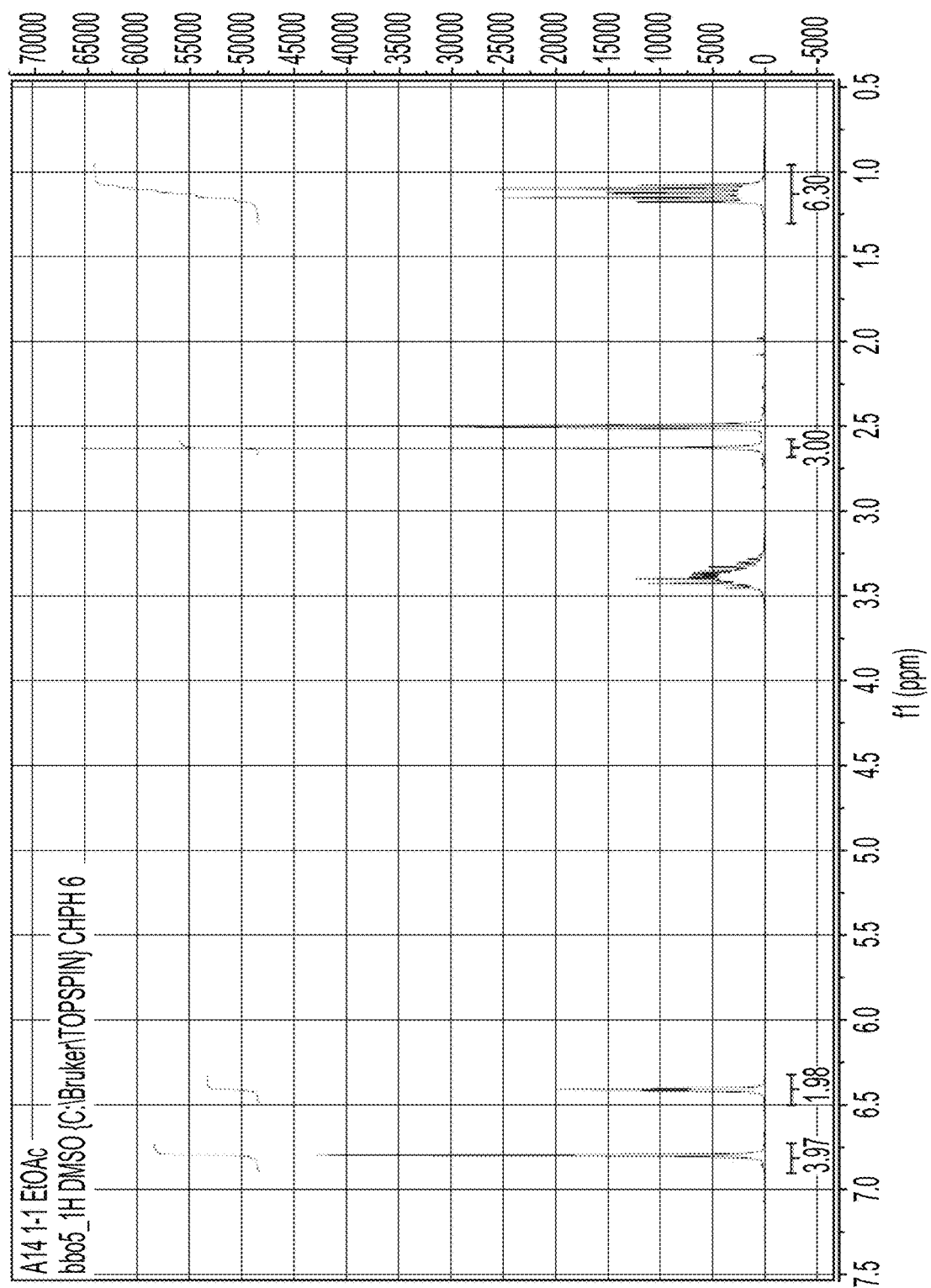
FIG. 18 shows Proton Nuclear Magnetic Resonance Spectroscopy ($^1$H NMR) analysis of the crystalline Form III.

The co-crystalline Form III of the compound of Formula I and 3,5-dihydroxybenzoic acid was prepared with the following procedures. To 1 ml of ethyl acetate are added 246.19 mg of 3,5-dihydroxybenzoic acid and 230 µl of the compound of Formula I to form a suspension. The suspension is left to stir for 48 h at room temperature to form a slurry. The slurry is filtered to produce the co-crystalline Form III. To determine the ratio of urea to the compound of Formula I, the NMR signal at 6.8 ppm (2C—H of 3,5-DHB) (FIG. 17) and at 2.63 ppm (the SO—CH$_3$ group of the compound of Formula I) are used. NMR shows a 2:1 co-crystal (2 molecules of 3,5-dihydroxybenzoic acid to 1 equivalent of the compound of Formula I) as shown in FIG. 18. FIG. 3 shows the X-ray powder diffraction pattern for the crystalline Form III. Peak positions are provided in Table 6.

TABLE 6

| Angle (2θ) | d value (Angstrom) |
|---|---|
| 13.02 | 6.80 |
| 13.71 | 6.46 |
| 14.31 | 6.19 |
| 26.28 | 3.39 |
| 27.20 | 3.28 |
| 31.63 | 2.83 |

Example 7

Preparation of Co-Crystalline Form IV of the Compound of Formula I and 3,5-Dihydroxybenzoic Acid at a Ratio of 1:1

Figure 22:
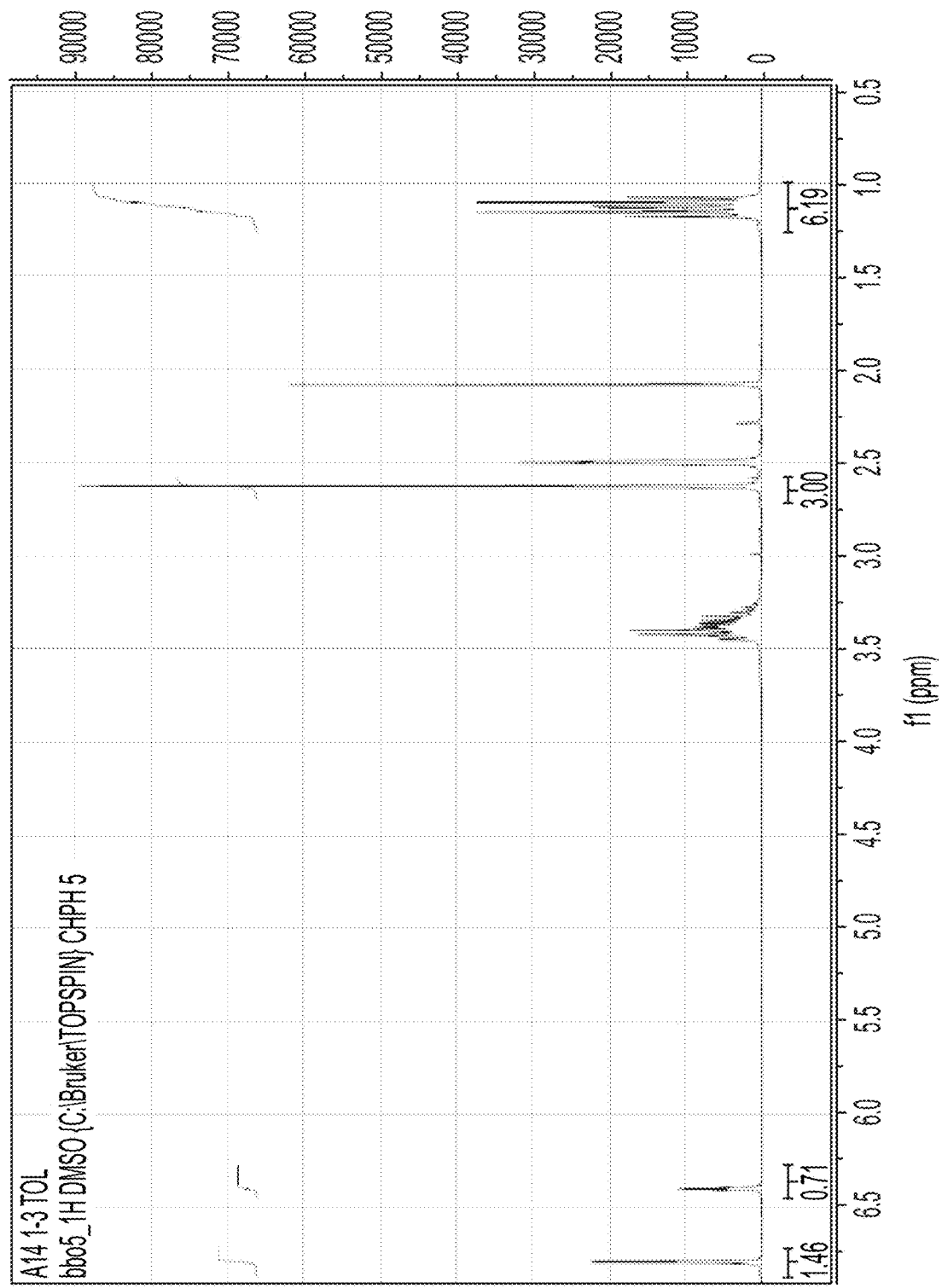
FIG. 22 shows Proton Nuclear Magnetic Resonance Spectroscopy ($^1$H NMR) analysis of the crystalline Form IV.

The co-crystalline Form IV of the compound of Formula I and 3,5-dihydroxybenzoic acid was prepared with the following procedures. To 1 ml of toluene are added 128.34 mg of 3,5-dihydroxybenzoic acid and 360 µl of the compound of Formula I to form a suspension. The suspension is left to stir for 48 h at room temperature to form a slurry. The slurry is filtered to produce the co-crystalline Form IV. To determine the ratio of 3,5-dihydroxybenzoic acid to the compound of Formula I, the NMR signal at 6.8 ppm (2C—H of 3,5-DHB) and at 2.63 ppm (the SO—CH$_3$ group of the compound of Formula I) are used. NMR shows a 0.73 ratio (3,5-DHB to the compound of Formula I), which indicated a 1:1 molar ratio of the compound of Formula I to urea in the powder as shown in FIG. 22. FIG. 4 shows the X-ray powder diffraction pattern for the crystalline Form IV. Peak positions are provided in Table 7.

TABLE 7

| Angle (2θ) | d value (Angstrom) |
|---|---|
| 7.62 | 11.60 |
| 12.99 | 6.82 |
| 13.32 | 6.65 |
| 16.66 | 5.32 |
| 17.23 | 5.15 |
| 18.07 | 4.91 |
| 19.66 | 4.52 |
| 20.63 | 4.31 |
| 21.35 | 4.16 |
| 22.50 | 3.95 |
| 26.53 | 3.36 |
| 31.32 | 2.86 |

Figure 24:
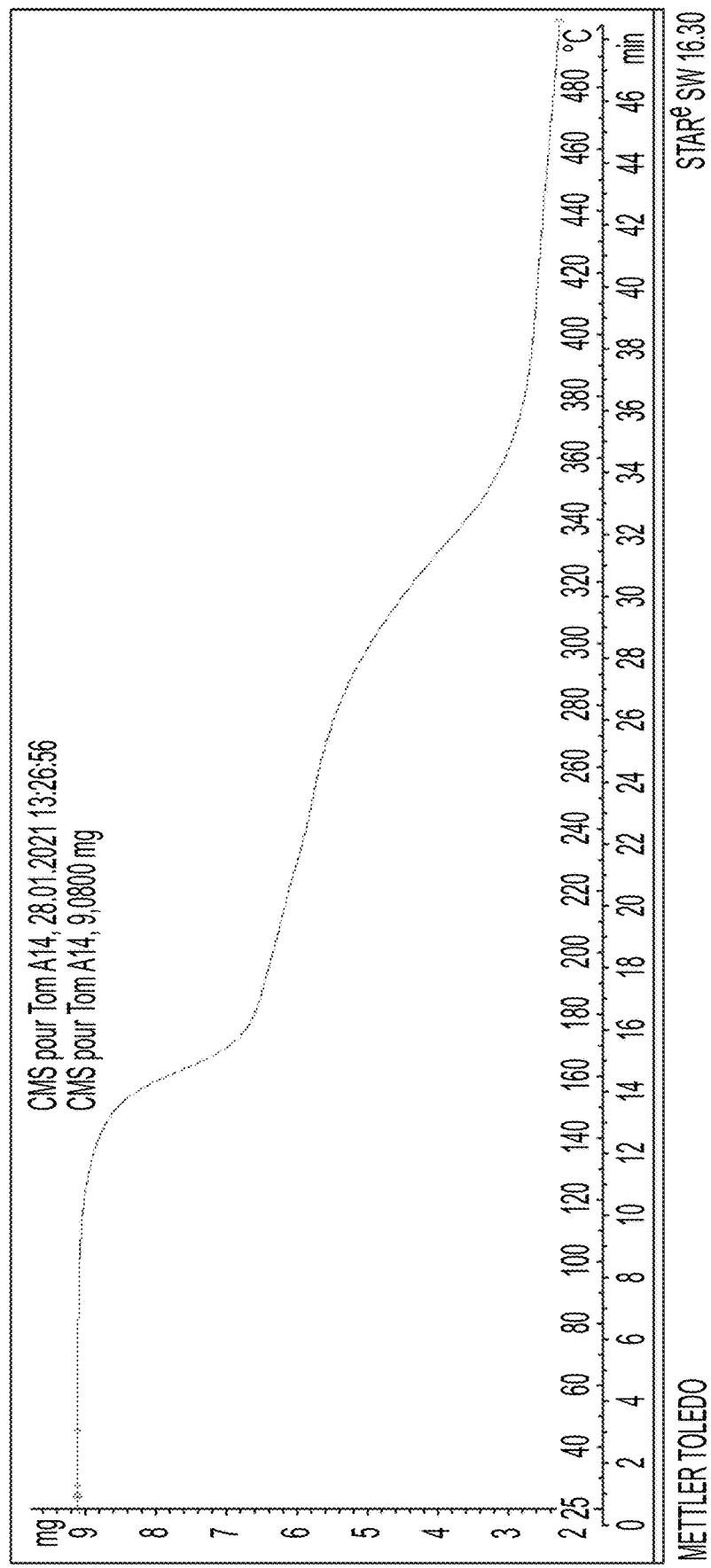
FIG. 24 shows TGA analysis of the crystalline Form IV.

DSC analysis of this sample shows an exothermic peak at 81° C. as shown in FIG. 23. TGA analysis result of this sample is shown in FIG. 24.

Example 8

Preparation of Co-Crystalline Form V of the Compound of Formula I and Ellagic Acid in Large Scale The co-crystalline Form V of the compound of Formula I and ellagic acid was prepared with the following procedures. Ellagic acid is first dried for 3 h at 180° C. Then, into ethylacetate are added a 1:1 molar ratio of dried ellagic acid and the compound of Formula I to form a suspension. The suspension is left to stir for 48 h at room temperature to form a slurry. The slurry is filtered to produce the co-crystalline Form V. TGA of the co-crystalline Form V shows a degradation occurring after 140° C., as shown in FIG. 13. FIG. 5 shows the X-ray powder diffraction pattern for the crystalline Form V. Peak positions are provided in Table 8.

TABLE 8

| Angle (2θ) | d value (Angstrom) |
|---|---|
| 7.03 | 12.58 |
| 10.71 | 8.26 |
| 14.36 | 6.17 |
| 21.26 | 4.18 |
| 24.14 | 3.69 |
| 26.10 | 3.41 |
| 26.60 | 3.35 |
| 28.51 | 3.13 |
| 29.60 | 3.02 |
| 7.03 | 12.58 |
| 10.71 | 8.26 |
| 14.36 | 6.17 |

Example 9

Figure 14:
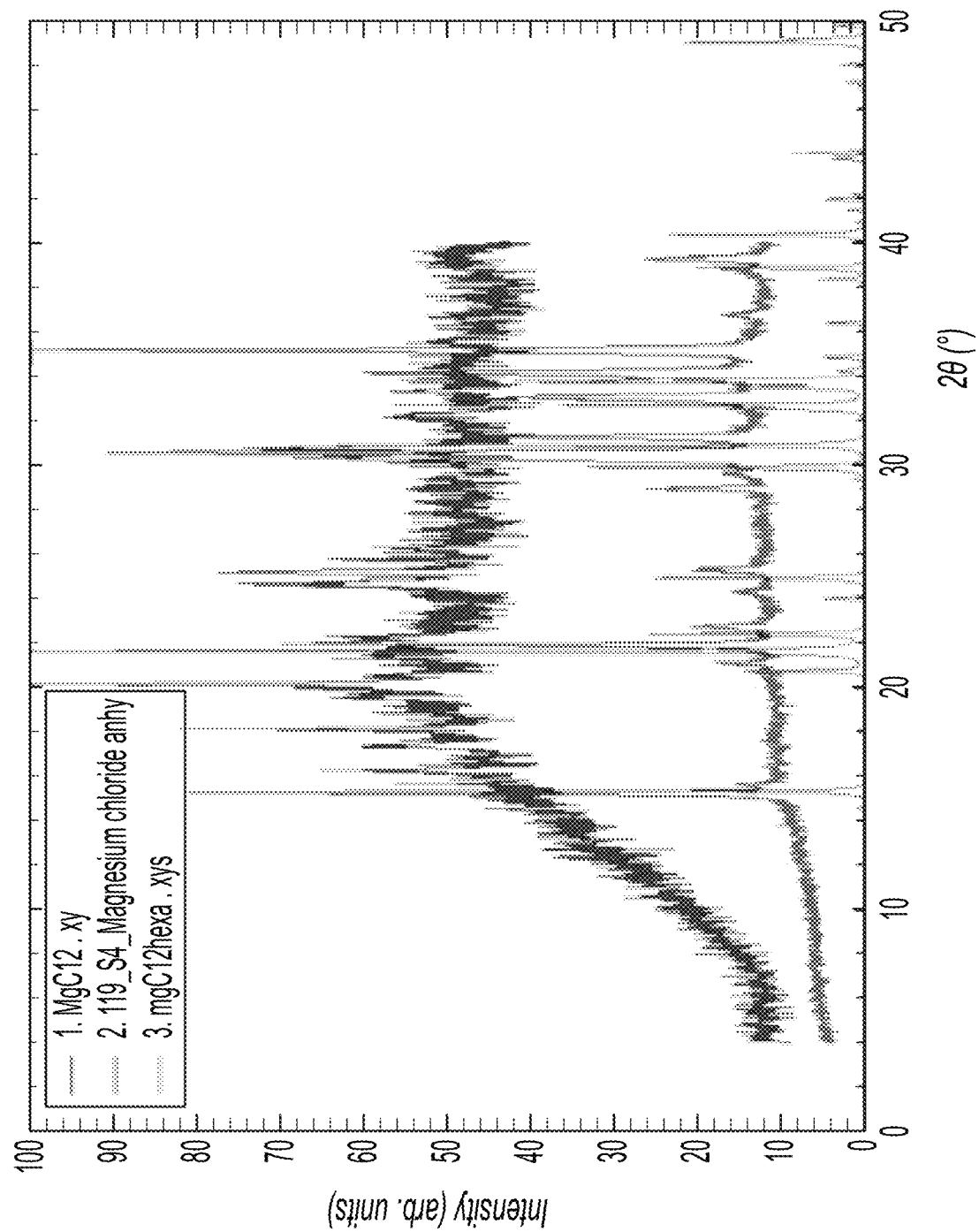
FIG. 14 shows the comparison of the XRPD patterns of the co-crystalline Form VI (blue), $MgCl_2$ (red), and $MgCl_2$ hexahydrate (green).
Figure 15:
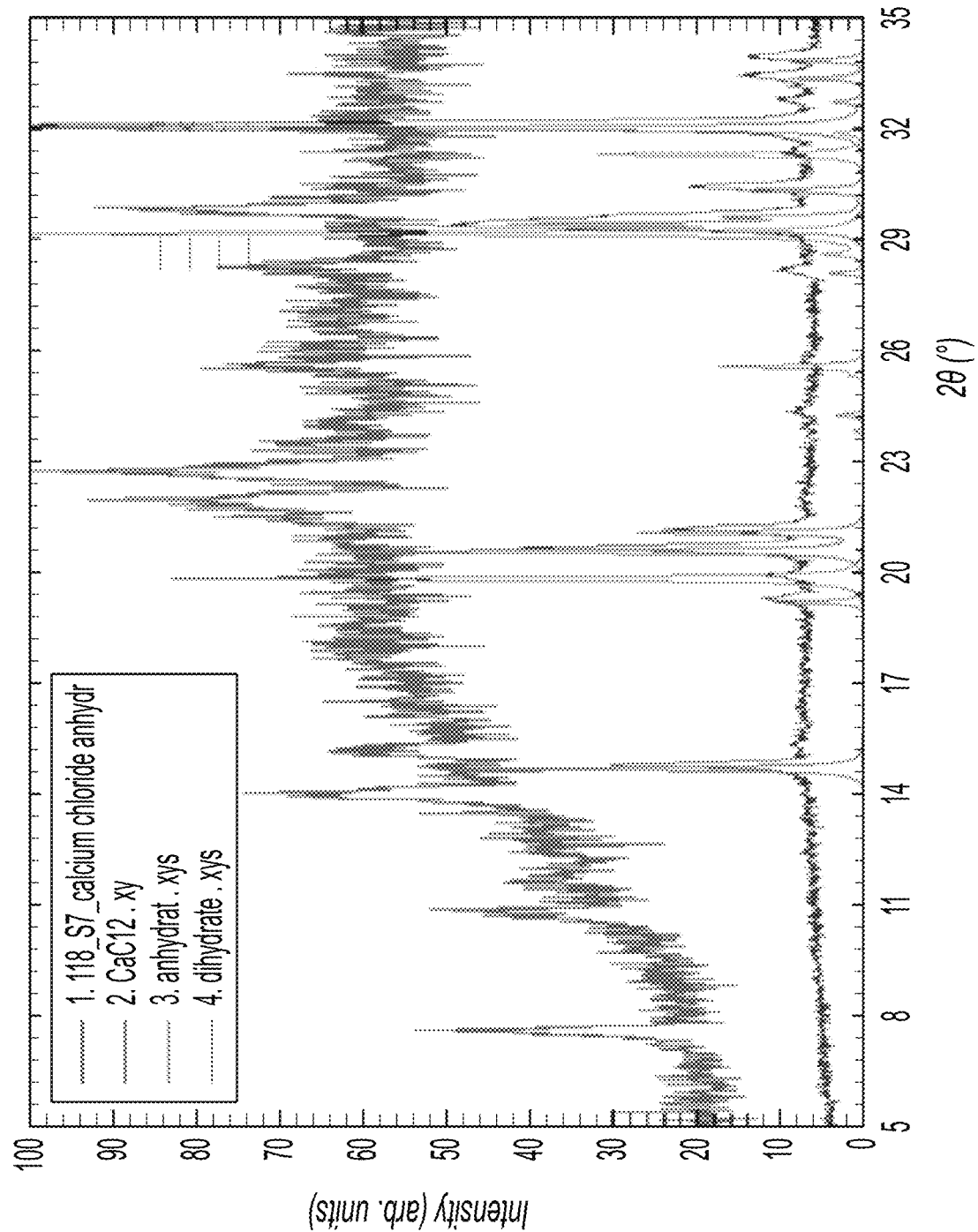
FIG. 15 shows the comparison of the XRPD pattern of the co-crystalline Form VII (red), the XRPD pattern of $CaCl_2$ (blue), the simulated XRPD pattern of $CaCl_2$ anhydrate (green) and the XRPD pattern of dihydrate (purple).

Preparations of Co-Crystalline Form VI of the Compound of Formula I and MgCl$_2$ and Co-Crystalline Form VII of the Compound of Formula I and CaCl$_2$ Co-crystalline Form VI of the compound of Formula I and MgCl$_2$ and co-crystalline Form VII of the compound of Formula I and CaCl$_2$ were prepared following the procedures described in Example 1. Although grinding the compound of Formula I with CaCl$_2$ and MgCl$_2$ at a 1:1 molar ratio resulted in the respective sticky solids, XRPD patterns showed peaks, which do not overlap with known forms of both salts as shown in FIGS. 14 and 15. FIG. 6 shows the X-ray powder diffraction pattern for the crystalline Form VI and peak positions are provided in Table 9. FIG. 7 shows the X-ray powder diffraction pattern for the crystalline Form VII and peak positions are provided in Table 10.

TABLE 9

| Angle (2θ) | d value (Angstrom) |
|---|---|
| 16.25 | 5.45 |
| 18.14 | 4.89 |
| 20.20 | 4.40 |
| 24.68 | 3.61 |
| 25.24 | 3.53 |
| 30.40 | 2.94 |
| 30.86 | 2.90 |
| 16.25 | 5.45 |
| 18.14 | 4.89 |
| 20.20 | 4.40 |

TABLE 10

| Angle (2θ) | d value (Angstrom) |
|---|---|
| 7.59 | 11.65 |
| 10.80 | 8.19 |
| 14.00 | 6.33 |
| 15.21 | 5.83 |
| 21.92 | 4.05 |
| 22.82 | 3.90 |
| 29.81 | 3.00 |

Figure 11:
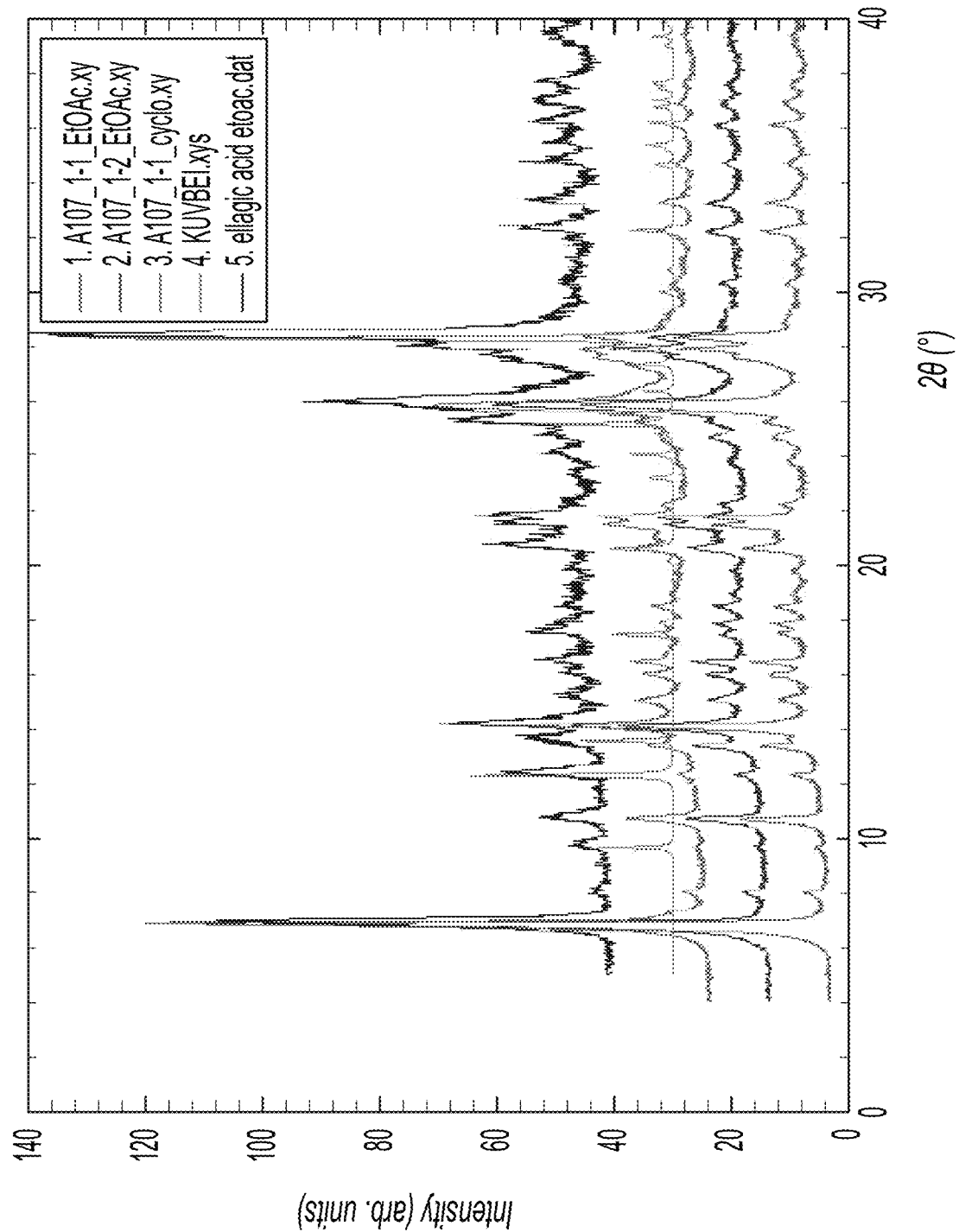
FIG. 11 shows the comparison of the XRPD pattern of the crystal obtained from slurrying the compound of Formula I and ellagic acid (non-dried) at a 1:1 molar ratio in ethyl acetate (brown), the simulated XRPD pattern of ellagic acid hydrate (pink), the XRPD pattern of the crystal obtained from slurrying the compound of Formula I and dried ellagic acid (1 h at 100° C.) at a 1:1 molar ratio in ethyl acetate, (red), the XRPD pattern of the crystal obtained from slurrying the compound of Formula I and dried ellagic acid (1 h at 100° C.) at a 1:2 molar ratio in ethyl acetate (blue), and the XRPD pattern of the crystal obtained from slurrying the compound of Formula I and dried ellagic acid (1 h at 100° C.) a 1:1 molar ratio in cyclohexane (green).
Figure 12:
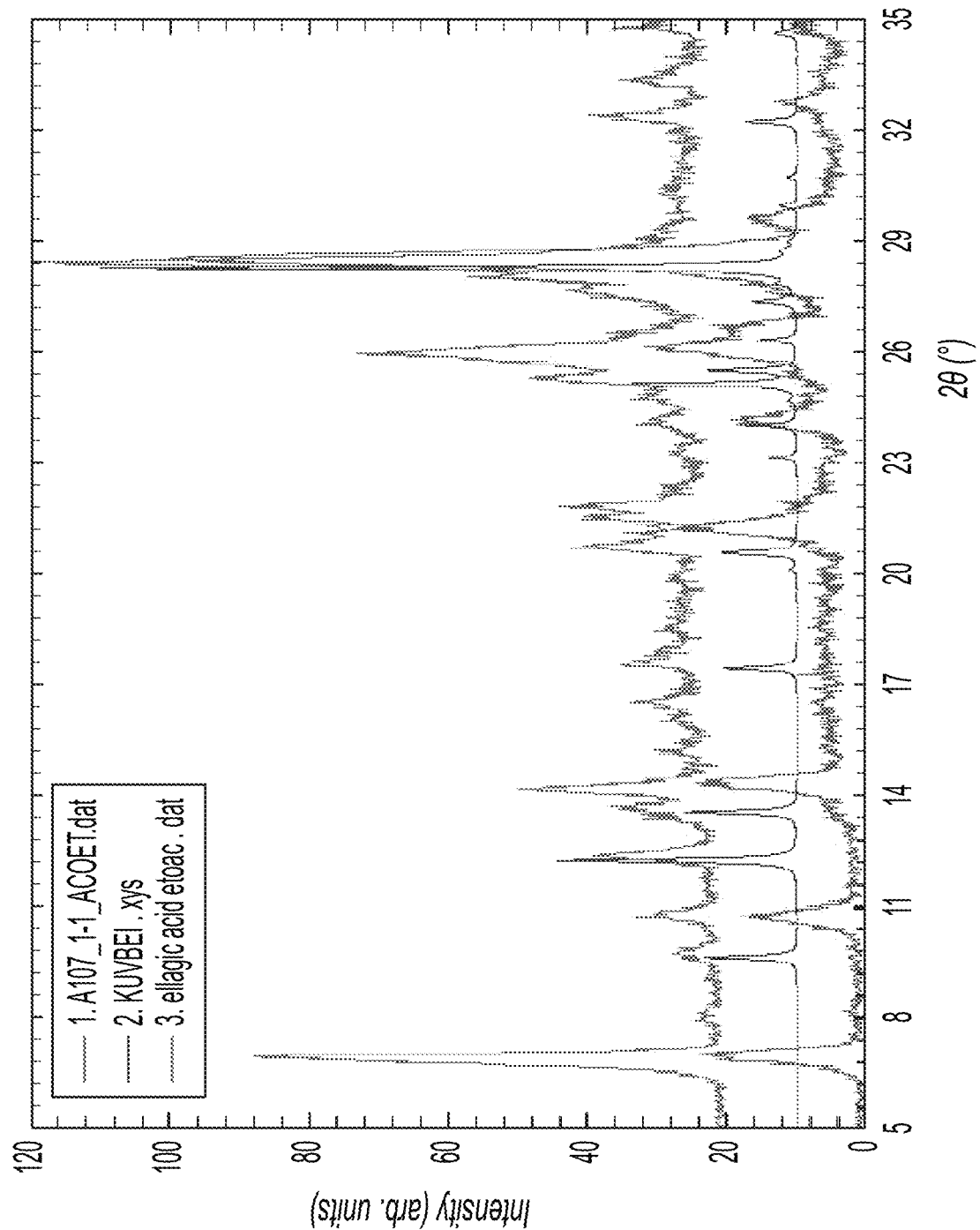
FIG. 12 shows the comparison of the XRPD patterns of the crystals obtained from slurrying the compound of Formula I and ellagic acid (non-dried) at a 1:1 molar ratio in ethyl acetate using the dried ellagic acid (3 h at 180° C.) (red) and non-dried ellagic acid (green) and the simulated XRPD pattern of the ellagic acid hydrate (blue).

When slurrying ellagic acid in various solvents using various ratios, one always obtained a mixture of co-crystal and remaining ellagic acid hydrate. The original ellagic acid used was a mixture of ellagic acid hydrate and anhydrate. The use of ellagic acid hydrate is not favorable to cocrystal formation, with the ΔG of co-crystal formation no longer favorable. Experiments were therefore performed by removing the hydrate. In the first series of experiments, ellagic acid was kept at 100° C. prior to using it in a 1:1 slurry experiment with ethyl acetate, cyclohexane and a 1:2 slurry experiment in ethyl acetate. As shown in FIG. 11, the residual peaks of ellagic acid hydrate have strongly been reduced, but traces are remaining. When ellagic acid is dried for 3 h at 180° C., a slurry of the dried ellagic acid and the compound of Formula I at a 1:1 molar ratio in ethyl acetate yields a pure co-crystal without traces of the hydrate remaining as shown in FIG. 12. Therefore, the procedure of drying ellagic acid at 180° C. for 3 h was implemented into the procedure as discussed hereinabove to the co-crystalline Form V.

Example 10

Preparations of the Compound of Formula IV-I

The compound of Formula IV-I can be prepared according to the preparation methods and processed as described in U.S. Patent Provisional Application No. 63/119,211, which is incorporated by the reference by its entirety. The compound of Formula IV-I can also be prepared with the process as described herein.

Synthesis of S-Methyl 4-hydroxy-1-piperidinecarbothioate

S,S'-Dimethyl dithiocarbonate (50 g; 410 mmol) (DMDTC) was combined with 4-hydroxypiperidine (62 g; 613 mmol) in 50 mL of methanol. A slight stream of nitrogen was introduced to the closed reaction vessel with a line for escaping methyl mercaptan, which was bubbled through a solution of commercial bleach (8.25% aqueous sodium hypochlorite). The reaction mixture was stirred at 45° C. for 4 hours; the heat was turned off while the reaction was stirred overnight at room temp. An HPLC analysis of a sample of the reaction mixture in the next day indicated ca. 90% consumption of DMDTC. 4-hydroxypiperidine (10 g; 99 mmol) was added and the temperature was raised to 45° C. After 4 hours, the HPLC analysis indicated the completion of the reaction. The methanol was removed by rotary evaporation, and the residue was dissolved in 500 mL of chloroform. The solution was washed sequentially with water (500 mL), 1N HCl (500 mL) and commercial bleach (8.25% aqueous sodium hypochlorite 200 mL diluted with 200 mL of water). The solution was then dried over $Na_2SO_4$ and evaporated to yield an amber oil that was purified on a column of silica gel (100 g) with MTBE as the elution. The purification from the silica gel chromatography yielded 58 g (81% yield) of S-Methyl 4-hydroxy-1-piperidinecarbothioate as a viscous oil. FTIR (KBr): $cm^{-1}$ 1620 (s, C=O); $^1$H NMR (400 MHz, $CD_3OD$): δ 3.7-4.1 (br s, 2H), 3.8 (m, 1H), 3.2 (m, 2H), 2.3 (s, 3H, S-Me), 1.85 (m, 2H), 1.4 (m, 2H); $^{13}$C NMR (100 MHz, $CD_3OD$): δ 168.1 (CO), 66.27 (CH), 41.98 ($CH_2$), 35.5 ($CH_2$), 11.57 ($SCH_3$).

The compound of Formula IV-I: 1-S-Methyl 1-S-oxo 4-hydroxy-1-piperidinecarbothioate S-Methyl 4-hydroxy-1-piperidinecarbothioate (22.6 g; 130 mmol) was dissolved in 500 mL of dichloromethane, and the solution was placed in a 1 L round bottom flask equipped with a thermowell thermometer and addition funnel. The reaction vessel was placed in an ice/methanol bath and dry ice was added in portions to maintain a temperature between –25° C. and –40° C. To this cold solution was added 24 mL (156 mmol) of a 33% solution of peracetic acid in acetic acid was added at a rate such that the reaction temperature did not go above –25° C. The reaction was warmed to room temp overnight. KI/starch paper indicated no peracid was present. HPLC indicated ca. 40% product and 40% starting material. The reaction was cooled to –40° C. and an additional 30 mol % (7 mL; 47 mmol) of the peracetic acid solution was added, and the reaction was complete after 2 hours. The reaction mixture was transferred to a 1 L round bottom flask and the DCM was removed on a rotary evaporator. Heptanes (200 mL) were added to the residue to azeotropically remove acetic acid. The resulting slurry was thoroughly triturated with sonication using 200 mL of MTBE to yield the compound of Formula IV-I as a white powder (21.0 g; 84.5%), mp 129.6-130.6° C.: FTIR (KBr): $cm^{-1}$ 1696 (s, C=O), 1085 (s, S=O); $^1$H NMR (400 MHz, $CD_3OD$): δ 4.82 (s, 1H, OH), 3.6-3.95 (m, 3H), 3.3-3.5 (m, 1H), 3.25 (m, 1H), 2.64 (s, 3H, S—$CH_3$), 2.5 (m, 2H), 1.85 (m, 2H); $^{13}$C NMR (100 MHz, $CD_3OD$): δ 167.3 (CO), 65.5 (CH), 41.5 ($CH_2$), 35.7 (S—$CH_3$), 33.0 ($CH_2$).

Example 11

Preparations of Crystalline Form VIII of the Compound of Formula IV-I

Figure 27:
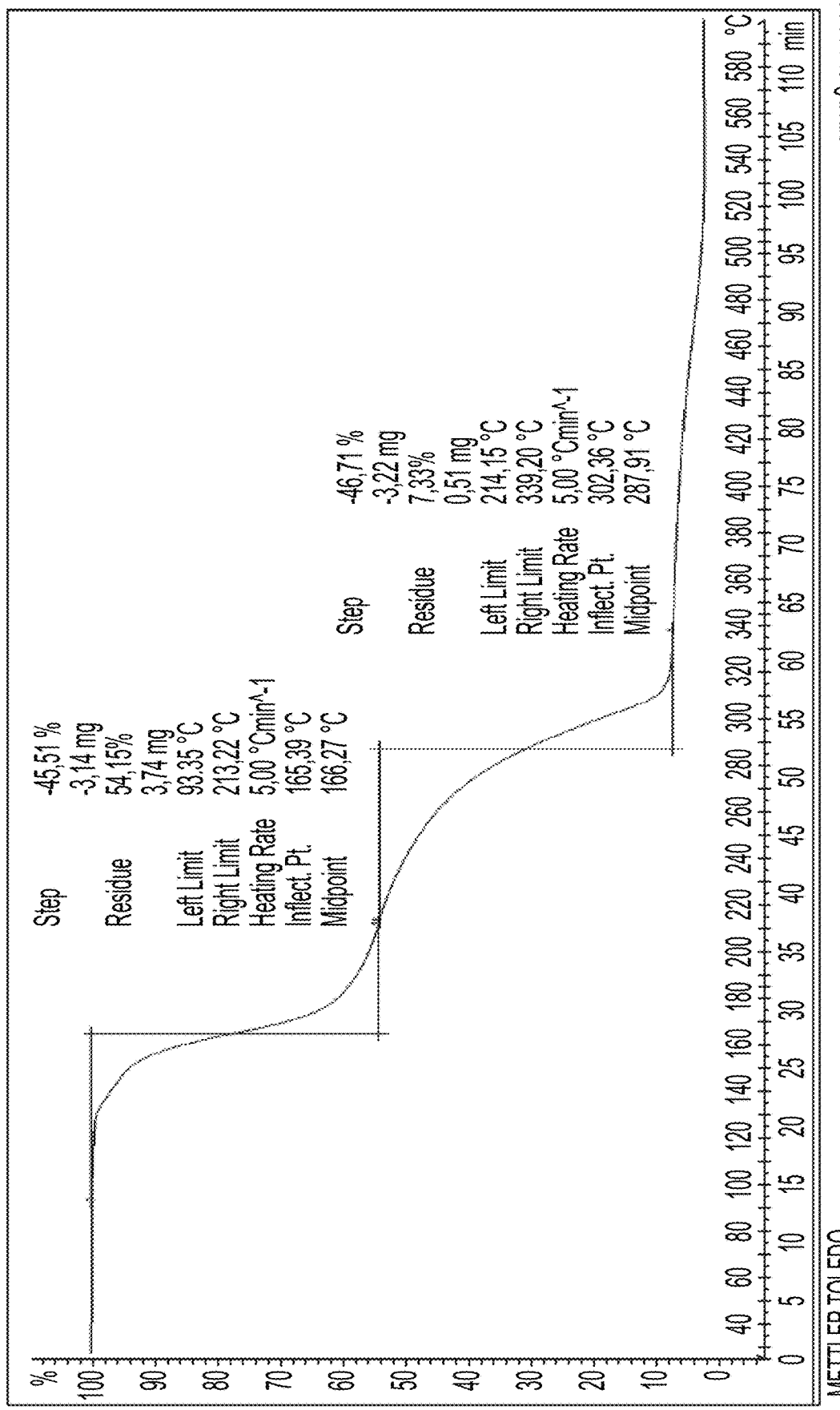
FIG. 27 shows TGA analysis of the crystalline Form VIII.
Figure 28:
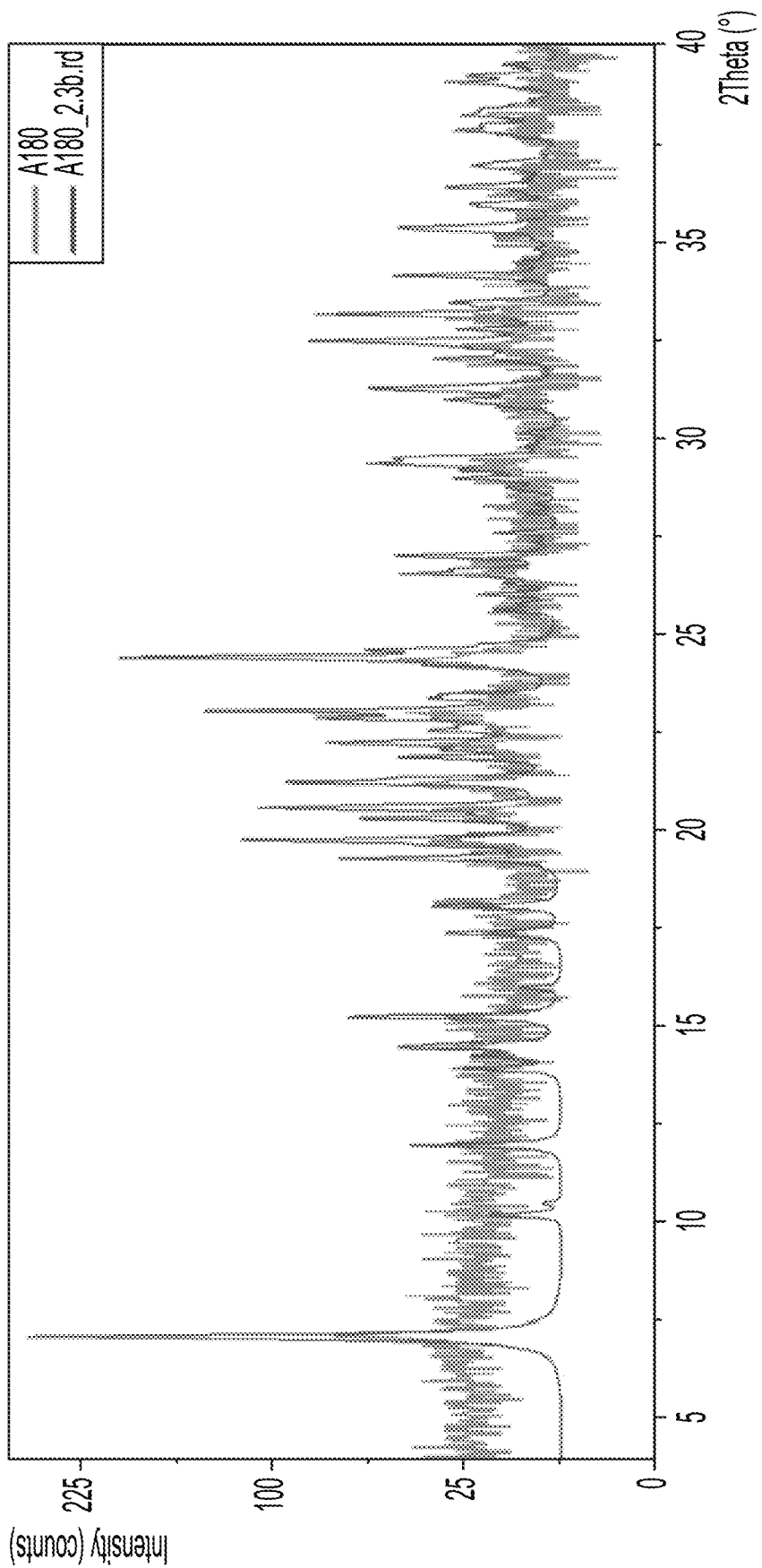
FIG. 28 shows the comparison between the calculated XRPD pattern (blue) and the experimental XRPD pattern (red) of the cocrystal of the compound of the Formula IV-I and trifluorotriiodobenzene.
Figure 29:
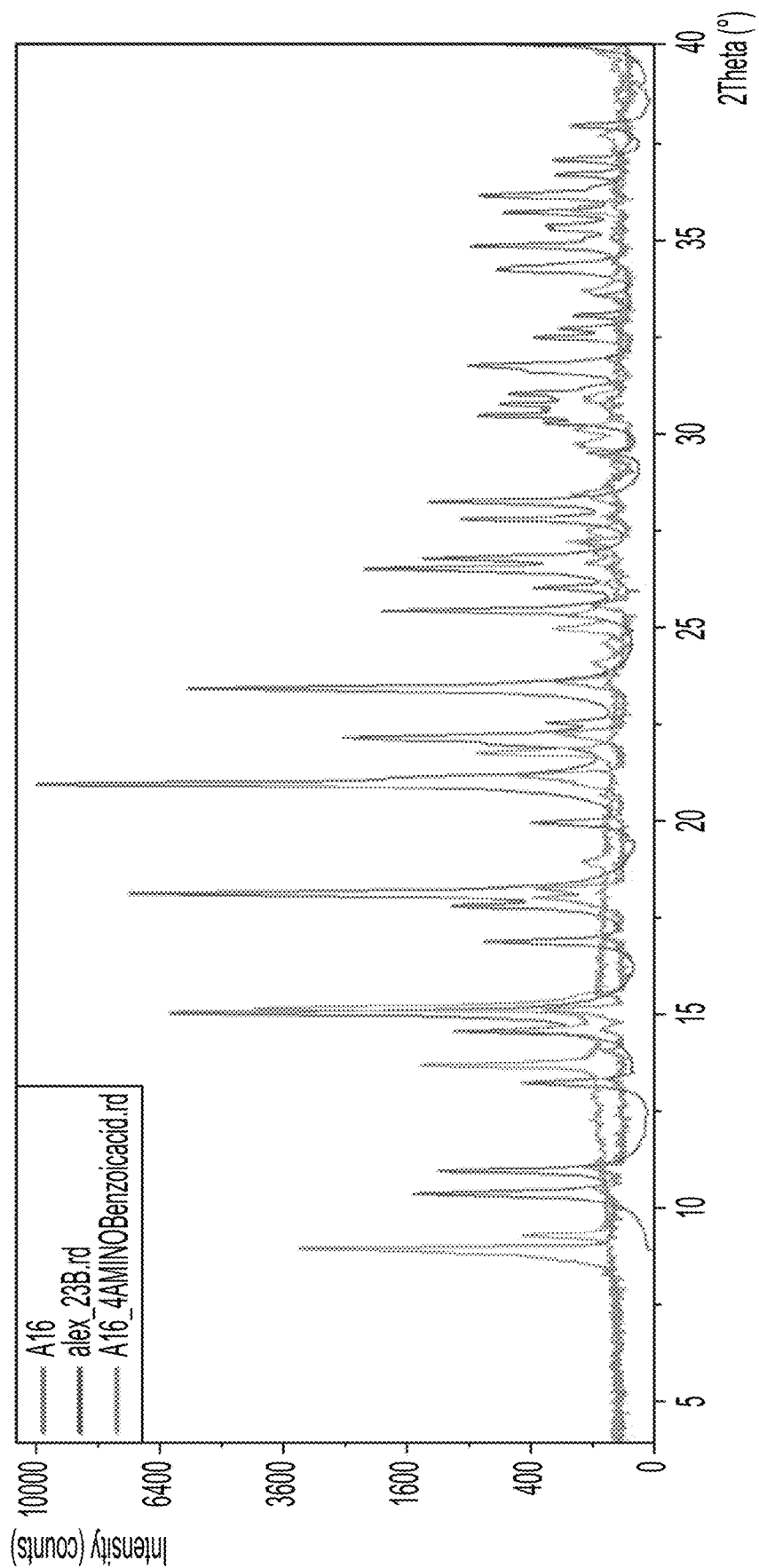
FIG. 29 shows the comparison between the calculated XRPD pattern (blue) and the experimental XRPD pattern (red) of the cocrystal of the compound of the Formula IV-I and 4-aminobenzoic acid, and the XRPD pattern of 4-aminobenzoic acid (green).
Figure 30:
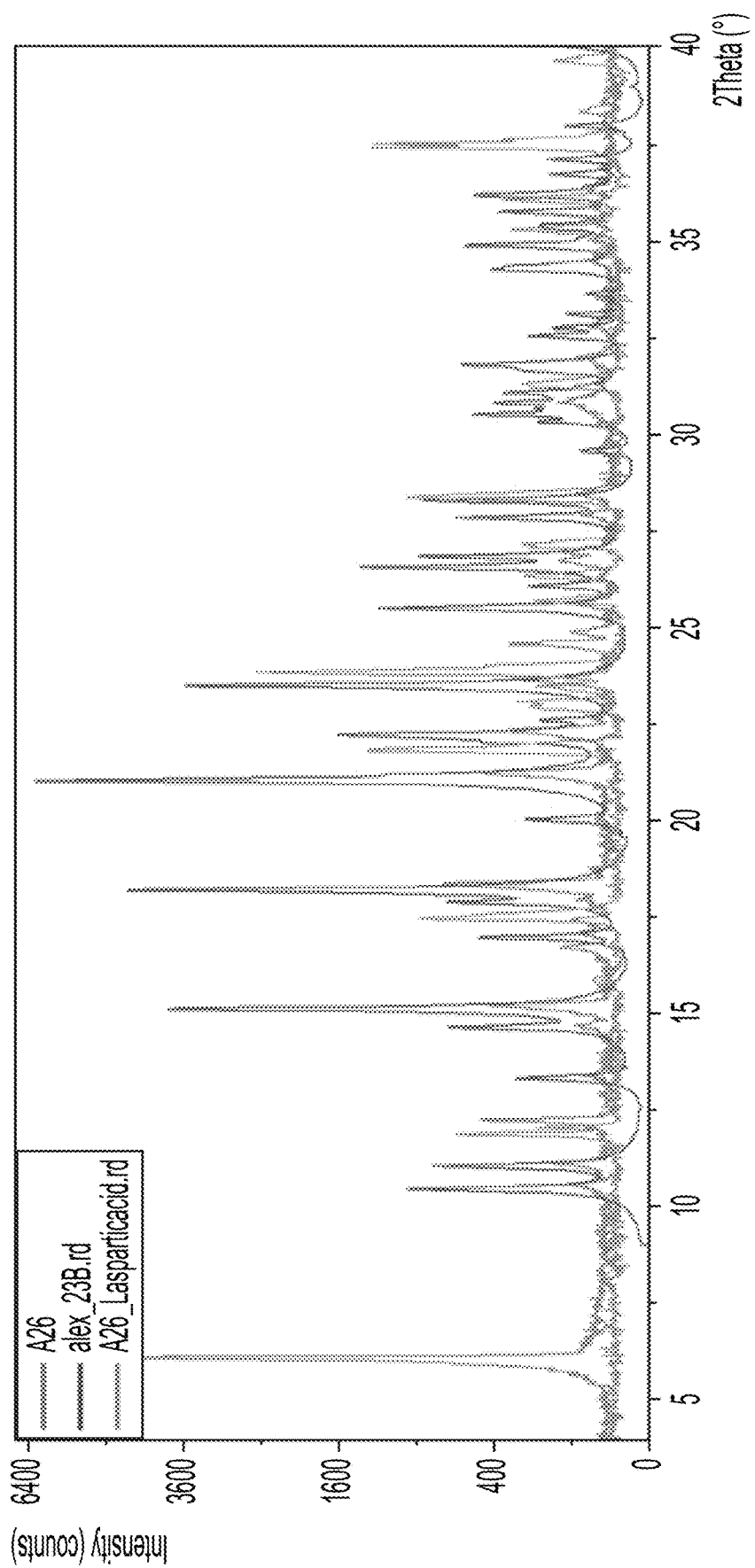
FIG. 30 shows the comparison between the calculated XRPD pattern (blue) and the experimental XRPD pattern (red) of the cocrystal of the compound of the Formula IV-I and L-aspartic acid, and the XRPD pattern of L-aspartic acid (green).
Figure 31:
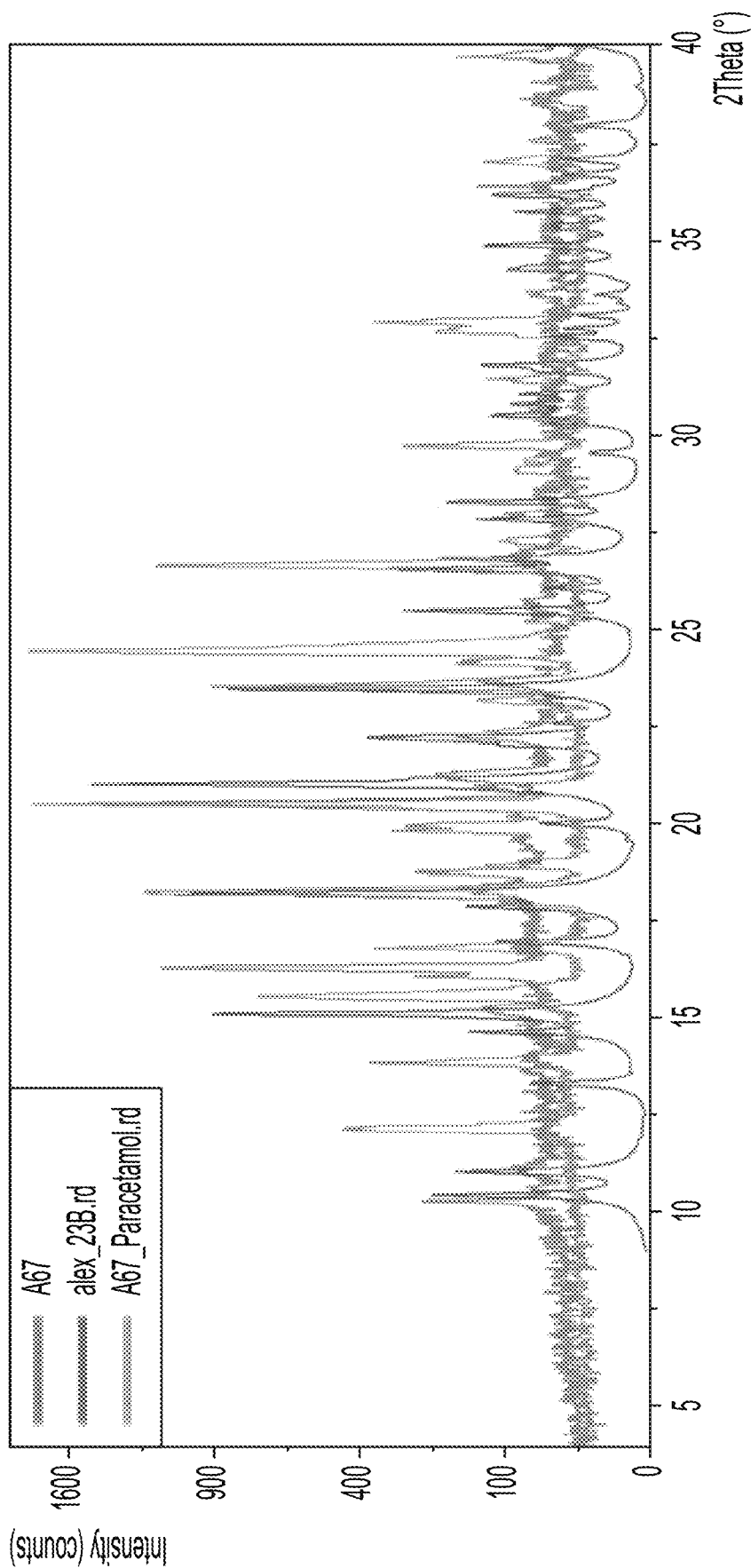
FIG. 31 shows the comparison between the calculated XRPD pattern (blue) and the experimental XRPD pattern (red) of the cocrystal of the compound of the Formula IV-I and paracetamol, and the XRPD pattern of paracetamol (green).
Figure 32:
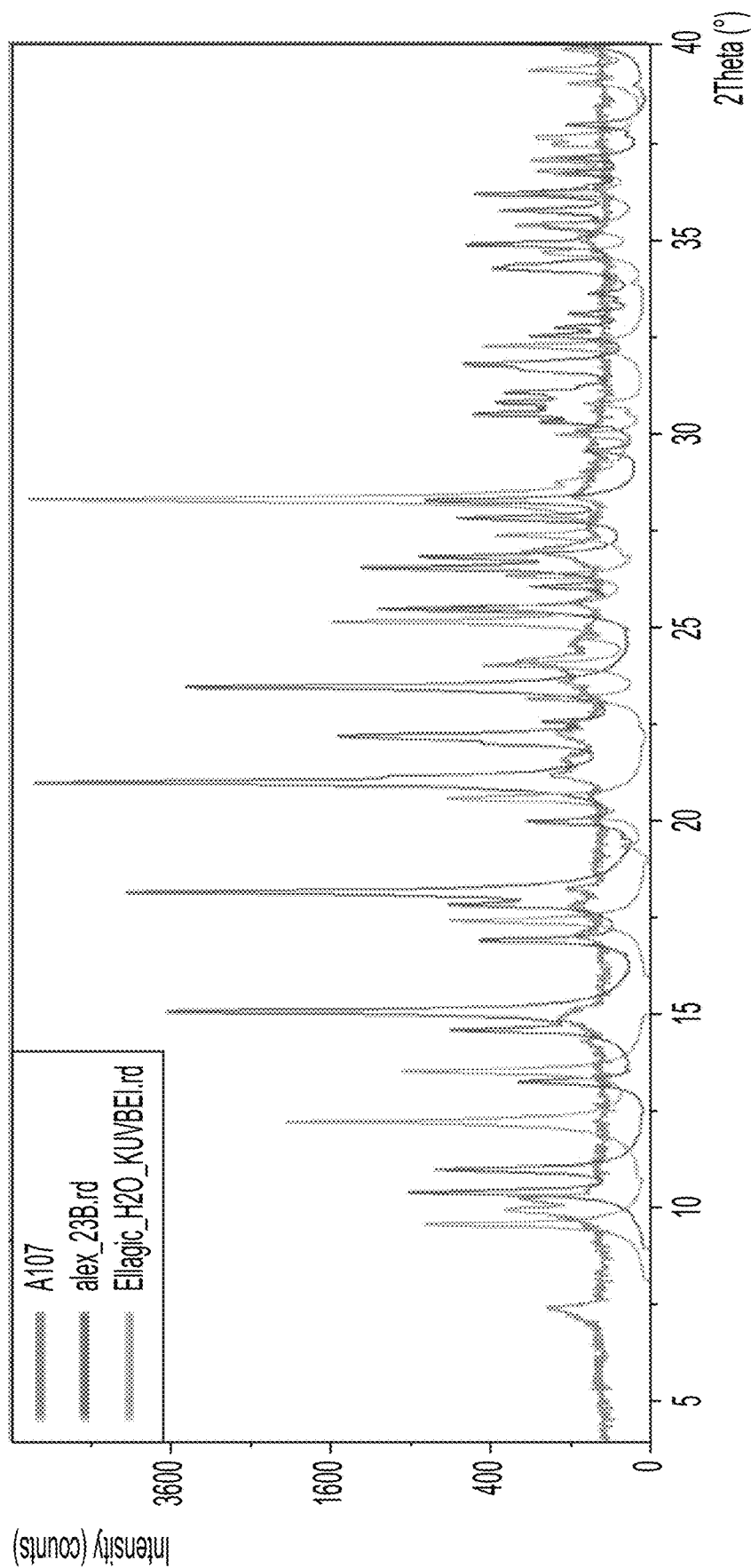
FIG. 32 shows the comparison between the calculated XRPD pattern (blue) and the experimental XRPD pattern (red) of the cocrystal of the compound of the Formula IV-I and ellagic acid, and the XRPD pattern of ellagic acid (green).
Figure 33:
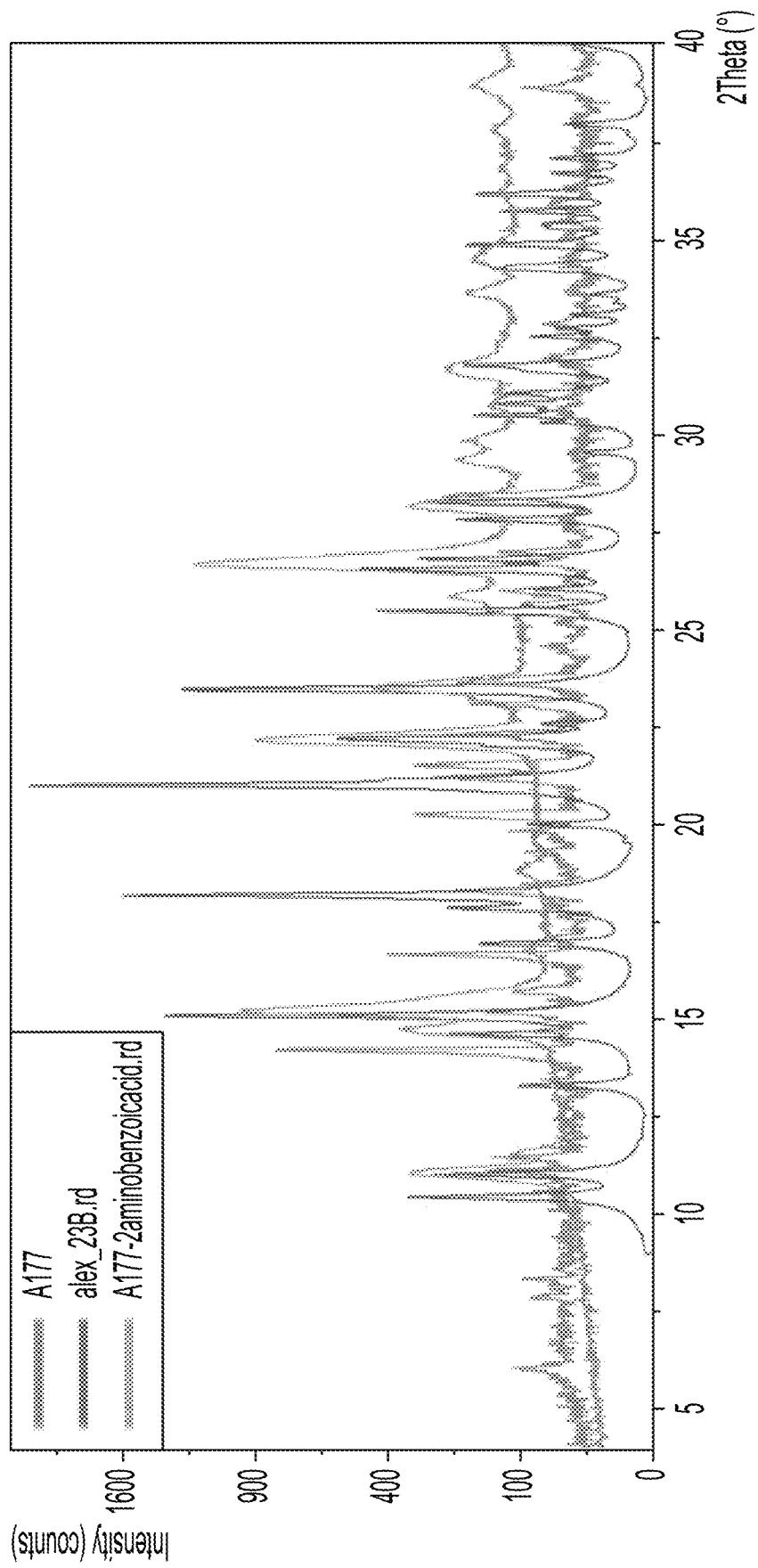
FIG. 33 shows the comparison between the calculated XRPD pattern (blue) and the experimental XRPD pattern (red) of the cocrystal of the compound of the Formula IV-I and 2-aminobenzoic acid, and the XRPD pattern of 2-aminobenzoic acid (green).
Figure 34:
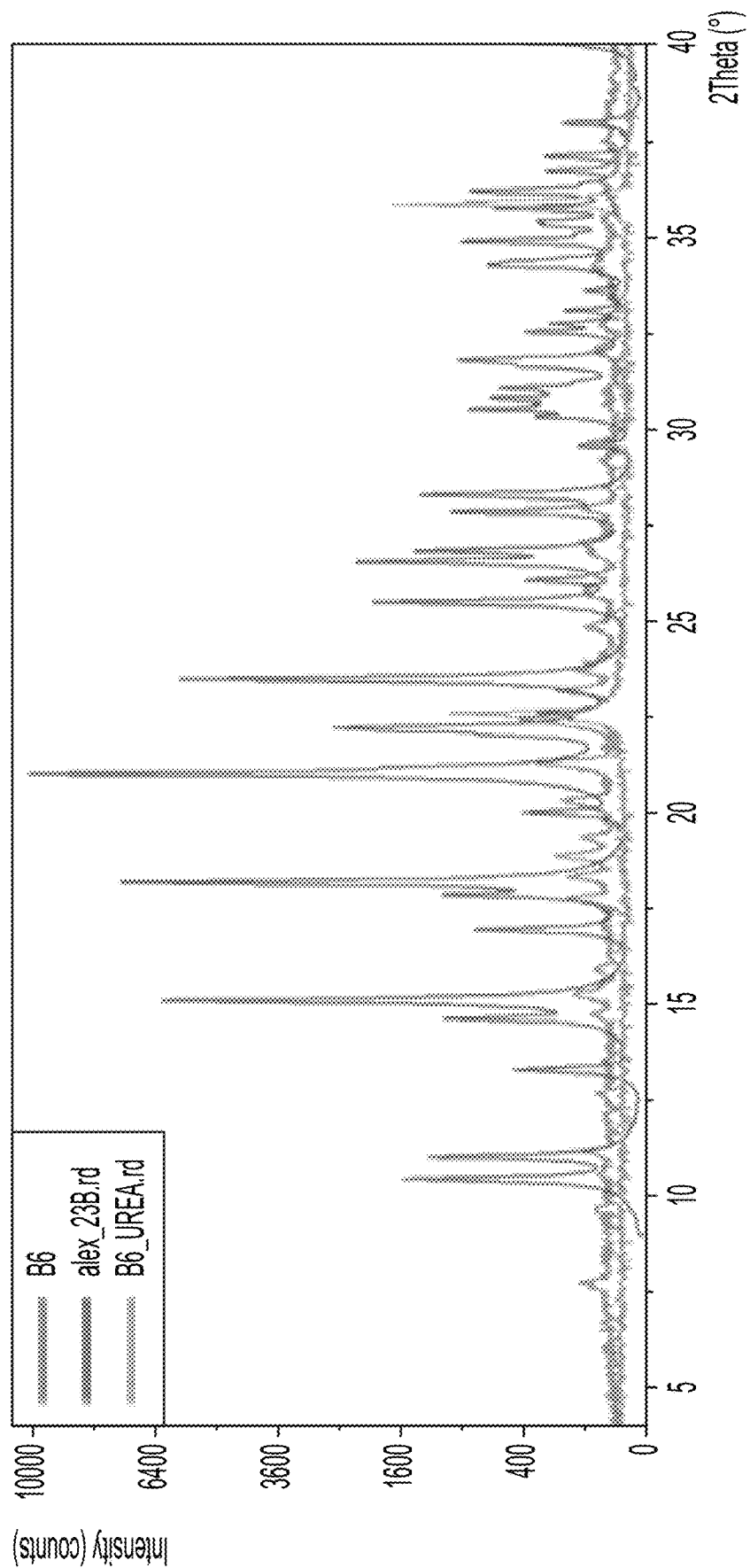
FIG. 34 shows the comparison between the calculated XRPD pattern (blue) and the experimental XRPD pattern (red) of the cocrystal of the compound of the Formula IV-I and urea, and the XRPD pattern of urea (green).

Crystalline Form VIII of the compound of Formula IV-1 was prepared following the procedure described herein. A single crystalline Form VI of the compound of Formula IV-I was obtained by dissolving 50 mg of the compound of Formula IV-1 in 1.5 mL of MeOH. The solution was left to evaporate at room temperature to produce crystals of sufficient size for single crystal analysis. TGA analysis of the co-crystalline Form V shows a degradation occurring after 140° C., as shown in FIG. 27. TGA analysis shows degradation to start between 100° C. and 120° C. FIG. 26 shows the X-ray powder diffraction pattern for the crystalline Form VIII. Peak positions are provided in Table 11.

TABLE 11

| Angle (2θ) | d value (Angstrom) |
|---|---|
| 10.5 | 8.41 |
| 11.1 | 7.99 |
| 14.6 | 6.05 |
| 15.1 | 5.86 |
| 17.0 | 5.22 |
| 17.9 | 4.96 |
| 18.2 | 4.87 |
| 21.1 | 4.21 |
| 22.2 | 4.00 |
| 23.5 | 3.78 |
| 25.5 | 3.49 |
| 26.6 | 3.35 |
| 26.9 | 3.32 |
| 27.8 | 3.21 |
| 28.3 | 3.15 |

Example 12

Polymorphic Screen for the Compound of Formula IV-I

The polymorphic screening of the compound of Formula IV-I was performed by suspending 50 mg of the compound of Formula IV-I in each of the solvents as described in Table 12 at a volume of 1.5 mL for all but water (1 mL) in a separate vial. The vials were sealed and the suspensions were left overnight. In the following day, the vials with the compound of Formula IV-I dissolved were opened and the solutions were left to evaporate at room temperature. The solid materials were collected after the complete evaporation of the solvent. In the vials where the compound of Formula IV-I was not fully dissolved, the mixtures were left to slurrying for another 96 h. The slurries were filtered and the obtained solids were analyzed.

TABLE 12

| # | Solvent | Suspension outcome |
|---|---|---|
| 1 | Acetonitrile | Slurry |
| 2 | EtOAc | Slurry |
| 3 | Toluene | Slurry |
| 4 | Cyclohexane | Slurry |
| 5 | Dichloromethane | Dissolved |
| 6 | Chloroform | Dissolved |
| 7 | MeOH | Dissolved |
| 8 | 2-propanol | Slurry |
| 9 | THF | Slurry |
| 10 | Acetone | Slurry |
| 11 | H$_2$O | Dissolved |
| 12 | EtOH | Dissolved |
| 13 | Nitromethane | Dissolved |
| 14 | Isopropyl acetate | Slurry |
| 15 | n-pentane | Slurry |
| 16 | n-hexane | Slurry |
| 17 | 1-propanol | Slurry |
| 18 | Methyl acetate | Slurry |
| 19 | Ethyl ether | Slurry |
| 20 | Octane | Slurry |

Surprisingly, in all the cases except dichloromethane as described herein, the same crystalline form of the compound of Formula IV-I was obtained and the crystalline form is the crystalline Form VIII as described in Example 11. The amorphous powder was also obtained after evaporation from dichloromethane. No polymorphic form or solvate of the compound of Formula IV-I has been identified with the solvents as described in Table 12.

Example 13

Co-Crystal Screening: Grinding Experiments of the Compound of Formula IV-I

The co-crystal screening of the compound of Formula IV-I with coformer was carried out through a dry grinding procedure. The cocrystallization experiments were performed by liquid-assisted grinding of an equimolar quantity of compounds of Formula IV-I and the corresponding coformer (1:1 ratio) using the "IST 400", 2 stainless steel balls (3 mm in diameter), and grinding for 30 minutes at 30 Hz, adding 1 drop of methanol as a solvent. The resulting powders were subject to XRPD analysis to compare with the calculated XRPD for each one for coformer. The results showed that the cocrystals tend to form between the compound of Formula IV-I and the coformer that is trifluorotriiodobenzene, 4-aminobenzoic acid, L-aspartic acid, paracetamol, ellagic acid, 2-aminobenzoic acid, or urea, based on the results showing the experimental XRPD patterns overlapping the corresponding simulated XRPD patterns as shown in FIGS. 28-34 and Table 13. Single crystals were found for the trifluorotriiodobenzene co-crystal, which shows a 1:1 cocrystal with the compound of Formula IV-I, and for the urea cocrystal, which shows a 3:1 cocrystal with the compound of Formula IV-I.

Coformer tested. A list of coformers was tested as shown in Table 13. Coformers were chosen from the list of most common co-crystal formers, including but not limited to the coformers described in Pharmaceutical Salts and Co-crystals, Johan Wouters and Luc Quéré, RSC publishing, 2011.

TABLE 13

| Coformer | Compound of Formula IV-I (mg) | Coformer (mg) | Cocrystallization |
|---|---|---|---|
| (S)-2-pyrrolidone-5-carboxylic acid | 59.70 | 40.30 | No |
| 2,3-dihydroxybenzoic acid | 55.38 | 44.62 | No |
| 2,5-dihydroxybenzoic acid (gentisic) | 55.38 | 44.62 | No |
| 3,4-dihydroxybenzoic acid | 55.38 | 44.62 | No |
| 4-hydroxybenzoic acid | 58.07 | 41.93 | No |
| 4-aminobenzoic acid | 58.24 | 41.76 | Yes |
| 4-hydroxy-3-methoxycinnamic acid (Ferulic) | 49.62 | 50.38 | No |
| acetylsalicylic acid | 51.49 | 48.51 | No |
| (L)-aspartic acid | 58.96 | 41.04 | Yes |
| Caffeine | 49.62 | 50.38 | No |
| Citric acid | 49.89 | 50.11 | No |
| fumaric acid | 62.23 | 37.77 | No |
| (RS)-Ibuprofen | 48.11 | 51.89 | No |
| (L)-malic acid | 58.78 | 41.22 | No |
| maleic acid | 62.23 | 37.77 | No |
| malonic acid | 64.76 | 35.24 | No |
| (S)-mandelic acid | 55.69 | 44.31 | No |
| oxalic acid | 67.99 | 32.01 | No |
| salicylic acid | 58.07 | 41.93 | No |
| succinic acid | 61.83 | 38.17 | No |
| (L)-tartaric acid | 56.04 | 43.96 | No |
| vanillin | 55.69 | 44.31 | No |
| Acetaminophen (paracetamol) | 55.85 | 44.15 | Yes |
| Theophylline | 51.49 | 48.51 | No |
| (S)-naproxen | 45.37 | 54.63 | No |
| adipic acid | 56.69 | 43.31 | No |
| glycolic acid | 71.55 | 28.45 | No |
| Benzoic Acid | 61.03 | 38.97 | No |
| p-coumaric acid | 53.83 | 46.17 | No |
| 3-hydroxybenzoic acid | 58.07 | 41.93 | No |
| Sorbic acid | 63.04 | 36.96 | No |
| o-benzoic sulfuimide (Saccharine) | 51.08 | 48.92 | No |
| 3,4,5-trihydroxybenzoic acid (Gallic acid) | 52.92 | 47.08 | No |
| ellagic acid hydrate | 47.65 | 52.35 | Yes |
| xanthine | 55.70 | 44.30 | No |
| methyl 3,4,5-trihydroxybenzoate | 50.95 | 49.05 | No |
| glutaric acid | 59.14 | 40.86 | No |
| Gallic acid ethyl ester (ethyl gallate) | 49.11 | 50.89 | No |
| Methyl 4-hydroxybenzoate | 55.69 | 44.31 | No |
| 2-ethoxybenzamide | 53.66 | 46.34 | No |
| meso-Erythritol | 61.03 | 38.97 | No |
| 2-aminobenzoic acid | 58.24 | 41.76 | Yes |
| Stearic acid | 40.20 | 59.80 | No |
| (L)-Ascorbic acid (vitamin C) | 52.06 | 47.94 | No |
| Nicotinic acid |  |  | No |
| trans-Cinnamic acid | 56.35 | 43.65 | No |
| 3-Ethoxy-4-hydroxybenzaldehyde (Ethylvanillin) | 53.51 | 46.49 | No |
| 3-Hydroxy-2-methyl-4-pyrone (Maltol) | 60.26 | 39.74 | No |
| curcumin | 34.17 | 65.83 | No |
| cholic acid | 31.88 | 68.12 | No |
| Glycine | 71.81 | 28.19 | No |
| Cysteine (L) | 61.22 | 38.78 | No |
| Histidine (L) | 55.21 | 44.79 | No |
| Threonine (L) | 61.62 | 38.38 | No |
| Tryptophan (L) | 48.36 | 51.64 | No |
| Proline (L) | 62.42 | 37.58 | No |
| Valine (L) | 62.01 | 37.99 | No |
| Leucine (L) | 59.32 | 40.68 | No |
| Phenylalanine (L) | 53.66 | 46.34 | No |
| Isoleucine (L) | 59.32 | 40.68 | No |
| Lysine (L) | 56.68 | 43.32 | No |
| Methionine (L) | 56.17 | 43.83 | No |
| carbamazepine | 44.73 | 55.27 | No |

TABLE 13-continued

| Coformer | Compound of Formula IV-I (mg) | Coformer (mg) | Cocrystal-lization |
|---|---|---|---|
| isonicotinamide | 61.03 | 38.97 | No |
| urea | 76.10 | 23.90 | Yes |
| nicotinamide | 61.03 | 38.97 | No |
| Salicylamide | 58.24 | 41.76 | No |
| Benzamide | 61.22 | 38.78 | No |
| Piracetam | 57.36 | 42.64 | No |
| L-Penicillamine | 56.17 | 43.83 | No |
| Quercetin | 38.75 | 61.25 | Undetermined |
| Rutin hydrate | 23.33 | 76.67 | No |
| (−)-Epicatechin | 39.72 | 60.28 | No |
| (+)-catechin hydrate | 38.29 | 61.71 | Yes |
| sucrose D(+) | 35.84 | 64.16 | No |
| Fructose D(−) | 51.49 | 48.51 | No |
| isomannide | 56.69 | 43.31 | No |
| D-Isosorbide | 56.69 | 43.31 | No |
| D-Sorbitol | 51.22 | 48.78 | No |
| D-Mannitol | 51.22 | 48.78 | No |
| aspartame | 39.39 | 60.61 | No |
| D-(+)-glucose anhydrous | 51.49 | 48.51 | No |
| Folic acid | 30.23 | 69.77 | No |
| hippuric acid | 51.63 | 48.37 | No |
| isophthalic acid | 53.51 | 46.49 | No |
| Menadione | 52.62 | 47.38 | No |
| Niacin | 60.84 | 39.16 | Undetermined |
| trifluorotriiodobenzene | 60.84 | 39.16 | Yes |
| Calcium Chloride | 63.28 | 36.72 | No |
| Magnesium Chloride | 66.76 | 33.24 | No |
| 4-tertbutylacyclohexanone | 58.96 | 41.04 | No |
| 4-methoxyacetophenone | 58.24 | 41.76 | No |
| Paracetamol | 55.85 | 44.15 | No |

Example 14

XRPD Analysis

X-ray powder diffraction (XRPD) measurements were performed with a Siemens D5000 diffractometer equipped with a Cu X-ray source operating at 40 kV and 40 mA and a secondary monochromator allowing to select the Kα radiation of Cu ($\lambda$=1.5418 Å). A scanning range of 20 values from 2° to 500 at a scan rate of 0.6° $\min^{-1}$ was applied.

Alternatively, Powder X-ray diffraction data were collected on a PANalytical Bragg-Brentano-geometry diffractometer, using Ni-filtered Cu Kα radiation ($\lambda$=1.54179 Å) at 40 kV and 40 mA with an X'Celerator detector. Each sample was analyzed between 4 and 50° in 20 with a step size of ca. 0.01670 and a total scan time of 3 min 48 s.

Example 15

Differential Scanning Calorimetric Analysis (DSC)

Co-crystalline forms of the compound of Formula I, Formula I-a, or Formula I-b, including the co-crystalline Forms I-VII, were analyzed using Differential Scanning Calorimetry. DSC measurements were performed on a TA DSC2500 with Tzero technology calibrated with indium under 50 mL/min continuous nitrogen flow. Samples were prepared in aluminum Tzero pans with a punctured hermetic lid. The temperature profile applied starts at 20° C. and increases up to 200° C. with a rate of 10° C./min.

Example 16

Nuclear Magnetic Resonance Spectroscopy (NMR)

Co-crystalline forms of the compound of Formula I, Formula I-a, or Formula I-b, including the co-crystalline Forms I-VII, were analyzed using $^1$H NMR spectroscopic experiments, which were performed on a 300 MHz spectrometer. Chemical shifts are reported in parts per million (ppm) and were normalized regarding the chemical shift of the peak of the deuterated solvent used.

Example 17

A Co-Crystalline Form Treated Alcohol-Related Disorders

A pharmaceutical composition comprising a co-crystalline form of the compound having a formula of

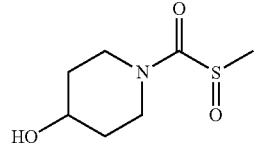

Formula IV-I and trifluorotriiodobenzene is administered to a subject suffering from alcohol use disorder. The subject is treated for alcohol use disorder and is found to drink less or no alcohol. The subject, for example, is found to consume less alcohol over a 90 day period as compared a 90 day period prior to being treated with the pharmaceutical composition. The subject is also found to have less cravings on the Visual Analogue Scale of Craving, which has 4 questions to assess domains of alcohol craving: the intention to drink, loss of control, relief craving, and urge intensity with a 0-20 point visual analogue scale for each item, with 0 indicating no craving and 20 indicating severe craving. The subject is found to have a reduction in the craving scale after 2 weeks of being treated with the pharmaceutical composition.

As an alternative, the number of drinks consumed in the natural environment [Time Frame: First 13 days of medication period] is measured and the subject is found to have a reduction in the number of drinks during the first 13 days of the medication period, as reported on a timeline followback interview.

Alternatively, the subject is found to have an increase in the percentage of no heavy drinking days during the period of treatment (e.g., 1, 2, 3, 4, 5, 6, 7, 8, 9, 10, 11, 12, or 13 weeks).

Example 18

A Co-Crystalline Form Treated Alcohol-Related Disorders

A pharmaceutical composition comprising a crystalline form of Form VIII of the compound having a formula of

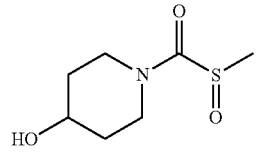

Formula IV-I is administered to a subject suffering from alcohol use disorder. The subject is treated for alcohol use disorder and is found to drink less or no alcohol. The subject, for example, is found to consume less alcohol over a 90 day period as compared a 90 day period prior to being treated with the pharmaceutical composition. The subject is also found to have less cravings on the Visual Analogue Scale of Craving, which has 4 questions to assess domains of alcohol craving: the intention to drink, loss of control, relief craving, and urge intensity with a 0-20 point visual analogue scale for each item, with 0 indicating no craving and 20 indicating severe craving. The subject is found to have a reduction in the craving scale after 2 weeks of being treated with the pharmaceutical composition.

As an alternative, the number of drinks consumed in the natural environment [Time Frame: First 13 days of medication period] is measured and the subject is found to have a reduction in the number of drinks during the first 13 days of the medication period, as reported on a timeline followback interview.

Alternatively, the subject is found to have an increase in the percentage of no heavy drinking days during the period of treatment (e.g., 1, 2, 3, 4, 5, 6, 7, 8, 9, 10, 11, 12, or 13 weeks).

The examples demonstrate the surprising and unexpected results of using a cocrystal coformer to treat alcohol use disorder.

Example 19

Co-Crystal Screening: Grinding Experiments of the Compound of Formula IV-Ia

Figure 35:
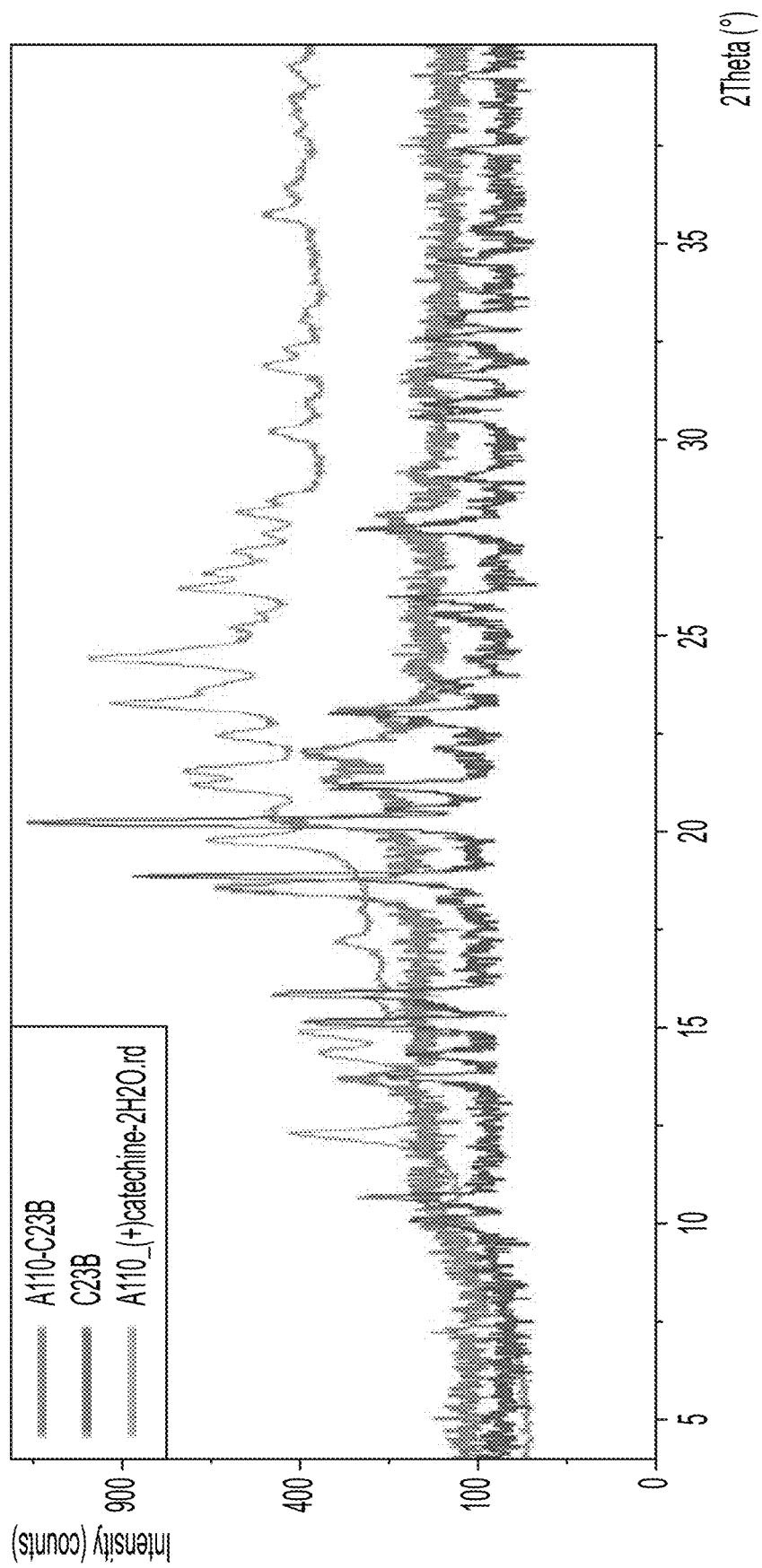
FIG. 35 shows the comparison between the calculated XRPD pattern (blue) and the experimental XRPD pattern (red) of the cocrystal of the compound of the Formula IV-Ia and (+)-catechine, and the XRPD pattern of (+)-catechine (green).
Figure 36:
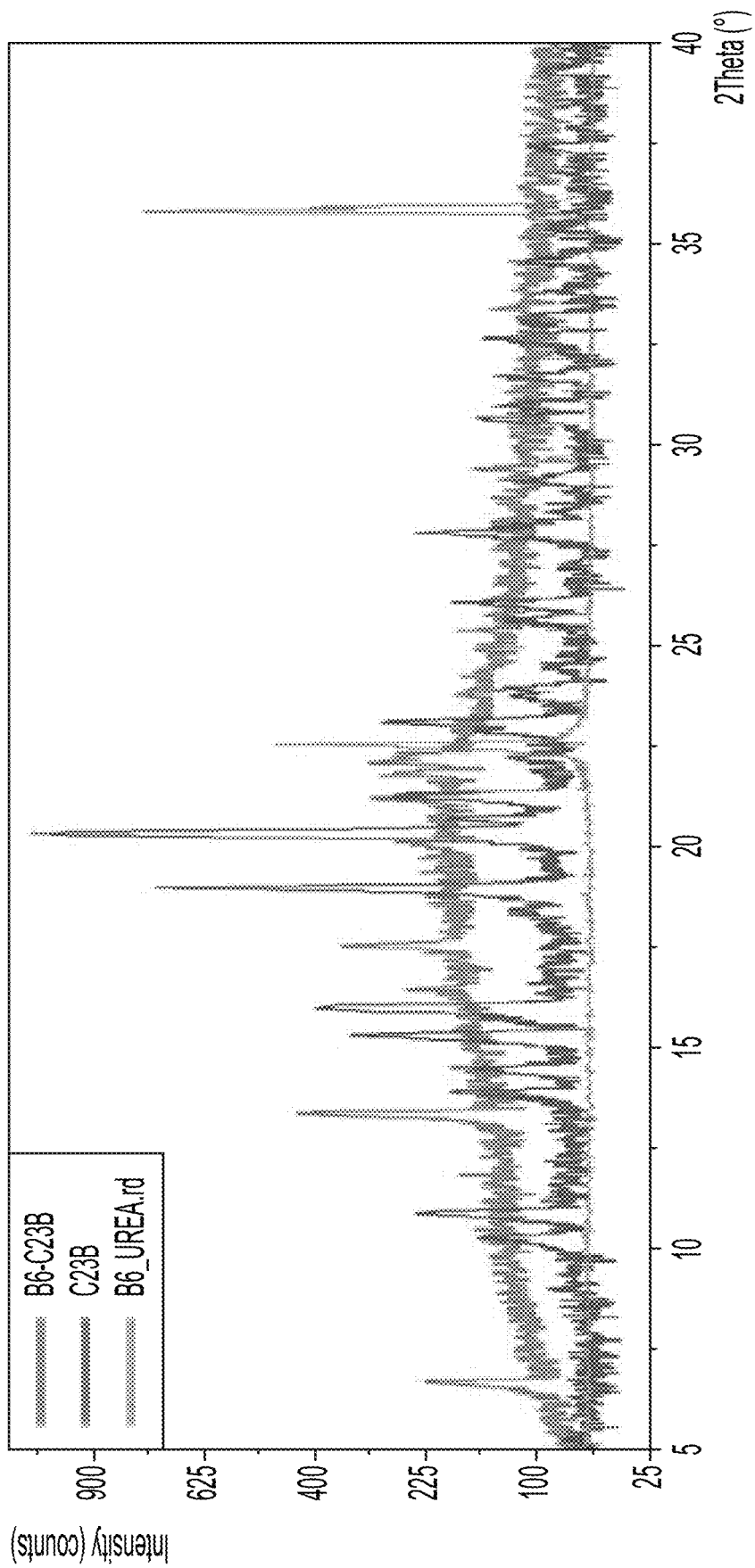
FIG. 36 shows the comparison between the calculated XRPD pattern (blue) and the experimental XRPD pattern (red) of the cocrystal of the compound of the Formula IV-Ia and urea, and the XRPD pattern of urea (green).
Figure 37:
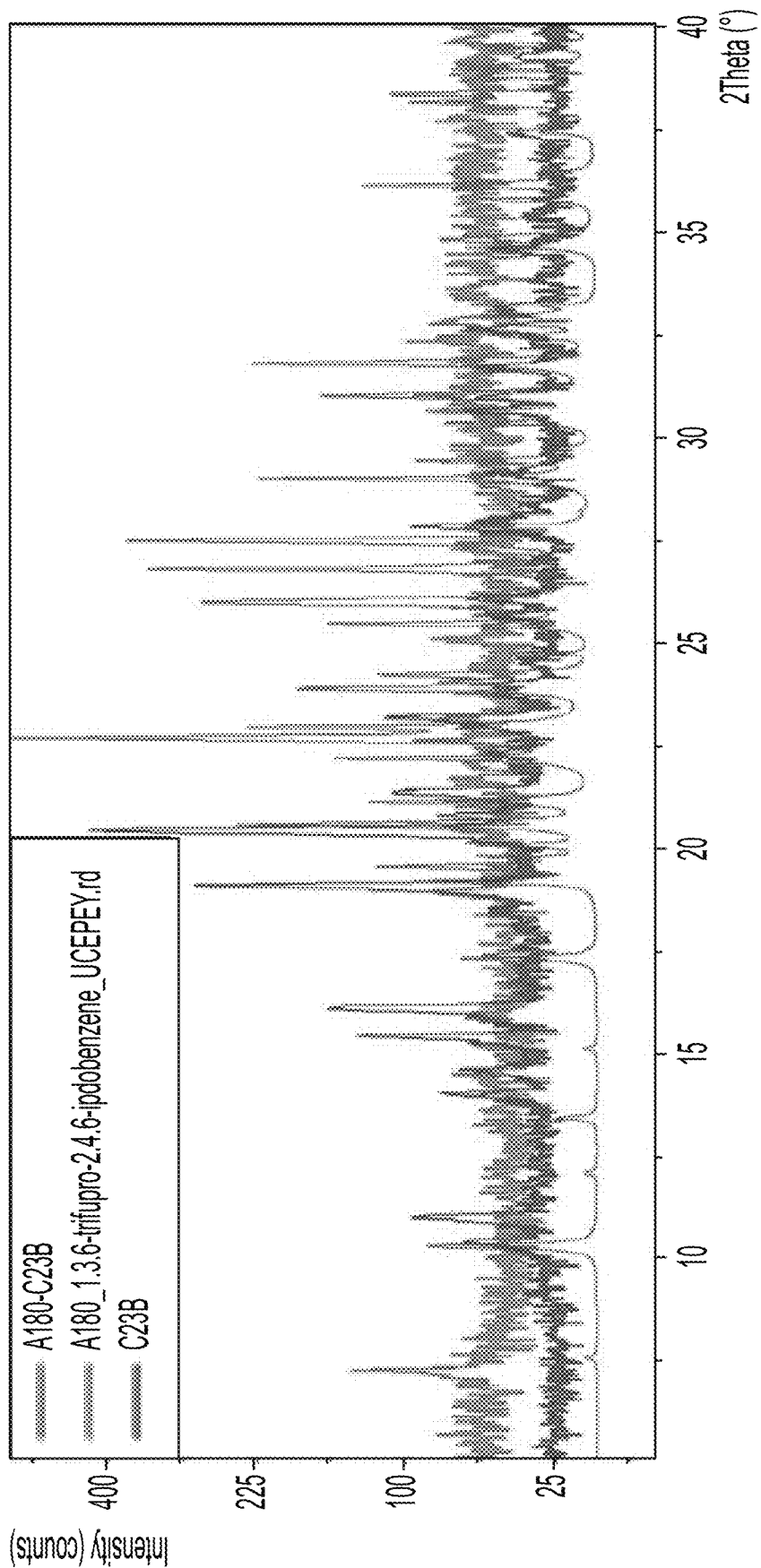
FIG. 37 shows the comparison between the calculated XRPD pattern (blue) and the experimental XRPD pattern (red) of the cocrystal of the compound of the Formula IV-Ia and 1,3,5-trifluoro-2,4,6-triiodobenzene, and the XRPD pattern of 1,3,5-trifluoro-2,4,6-triiodobenzene (green).

The co-crystal screening of the compound of Formula IV-Ia with coformers was carried out through a dry grinding procedure. The co-crystallization experiments were performed by liquid-assisted grinding of an equimolar quantity of the compound of Formula IV-Ia and the corresponding coformer (1:1 ratio) using the "IST 400", 2 stainless steel balls (3 mm in diameter), and grinding for 30 minutes at 30 Hz, adding 1 drop of methanol as a solvent. The resulting powders were subject to XRPD analysis to compare with the calculated XRPD for each coformer. The results showed that the cocrystals tend to form between the compound of Formula IV-Ia and the coformer that is catechin, urea, and triiodotrifluorobenzene, based on the results showing the experimental XRPD patterns overlapping the corresponding simulated XRPD patterns as shown in FIGS. 35-37 and Table 14. Single crystals were found for the urea co-crystal, which shows a 1:2 cocrystal with the compound of Formula IV-Ia.

Coformers tested. A list of coformers was tested as shown in Table 14. Coformers were chosen from the list of most common co-crystal formers, including but not limited to the coformers described in Pharmaceutical Salts and Co-crystals, Johan Wouters and Luc Quéré, RSC publishing, 2011.

TABLE 14

| Coformer | Compound of Formula IV-Ia (mg) | Coformer (mg) | Cocrystallization |
|---|---|---|---|
| 2-Aminobenzoic acid | 58.24 | 41.76 | No |
| Ascorbic acid (Vitamin C) | 52.06 | 47.94 | No |
| (+)-catechin | 38.29 | 61.71 | Yes |
| Penicillamine | 56.17 | 43.83 | No |
| Urea | 76.10 | 23.90 | Yes |
| Triiodotrifluorobenzene | 27.28 | 72.72 | Yes |
| Gentisic acid | 19.07 | 15.62 | No |
| 2,3-dihydroxybenzoic acid | 19.10 | 15.47 | No |
| 3,4-dihydroxybenzoic acid | 19.10 | 15.63 | Undetermined |
| 3-hydroxybenzoic acid | 19.04 | 15.90 | Undetermined |

What is claimed is:

1. A co-crystalline form comprising a compound having a formula of

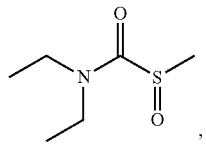
Formula I

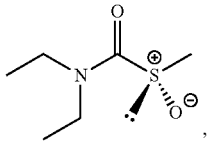
Formula I-a

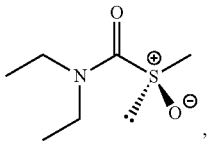
Formula I-b

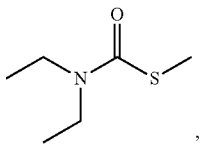
Formula II

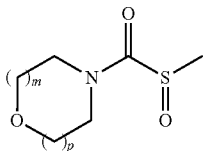
Formula III

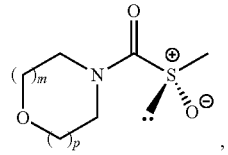
Formula III-a

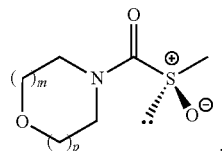
Formula III-b

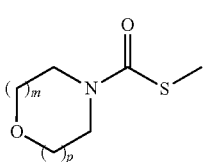
Formula VI

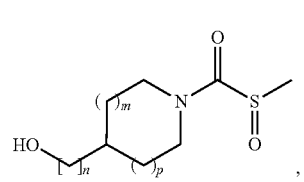
Formula IV

-continued

Formula IV-a

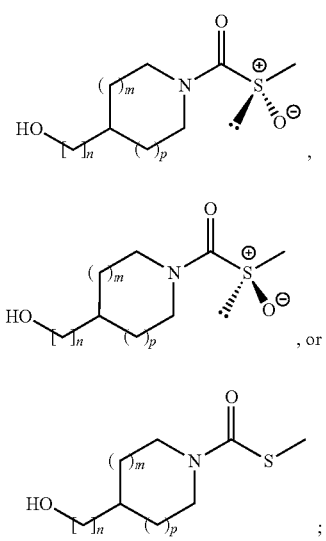

Formula IV-b

Formula V and a coformer, wherein the coformer is urea, 3,5-dihydroxybenzoic acid, trimesic acid, ellagic acid, $MgCl_2$, or $CaCl_2$), or any combination thereof, wherein n is 0-6;

m is 0-6; and p is 0-6.

2. The co-crystalline form of claim 1, wherein the compound has a formula of

Formula IV

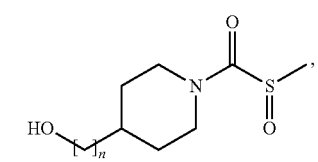

Formula IV-a

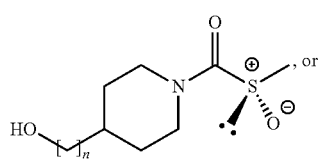

Formula IV-b

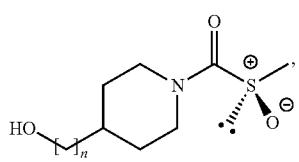

wherein n is 0-6.

3. The co-crystalline form of claim 2, wherein the compound has a formula of

Formula IV-I

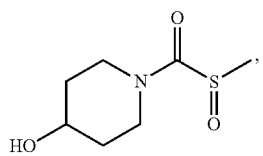

Formula IV-Ia

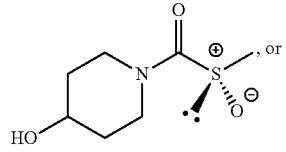

Formula IV-Ib

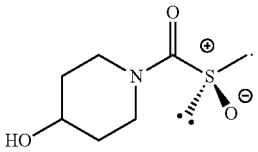

4. The co-crystalline form of claim 2, wherein the coformer is urea.

5. The co-crystalline form of claim 4, wherein the molar ratio of the compound to the urea is about 1:1.

6. The co-crystalline form of claim 1, wherein the molar ratio of the compound to the coformer is from about 1:5 to about 5:1.

7. The co-crystalline form of claim 1, wherein the form is characterized by an X-ray powder diffraction pattern comprising one or more peaks at about 9.0±0.5 degrees 2θ, at about 11.7±0.5 degrees 2θ, at about 14.9±0.5 degrees 2θ, at about 17.0±0.5 degrees 2θ, at about 17.2±0.5 degrees 2θ, at about 17.8±0.5 degrees 2θ, at about 18.0±0.5 degrees 2θ, at about 18.6±0.5 degrees 2θ, at about 21.1±0.5 degrees 2θ, at about 21.5±0.5 degrees 2θ, at about 21.7±0.5 degrees 2θ, at about 23.4±0.5 degrees 2θ, at about 24.8±0.5 degrees 2θ, at about 25.1±0.5 degrees 2θ, at about 25.3±0.5 degrees 2θ, at about 25.9±0.5 degrees 2θ, at about 26.2±0.5 degrees 2θ, at about 27.7±0.5 degrees 2θ, at about 28.2±0.5 degrees 2θ, at about 29.3±0.5 degrees 2θ, at about 29.8±0.5 degrees 2θ, at about 31.7±0.5 degrees 2θ, at about 32.1±0.5 degrees 2θ, and at about 33.3±0.5 degrees 2θ.

8. The co-crystalline form of claim 1, wherein the form is characterized by an X-ray powder diffraction pattern comprising one or more d-spacing values at about 9.8±0.5 degrees angstroms, at about 7.6±0.5 degrees angstroms, at about 5.9±0.5 degrees angstroms, at about 5.2±0.5 degrees angstroms, at about 5.2±0.5 degrees angstroms, at about 5.0±0.5 degrees angstroms, at about 4.9±0.5 degrees angstroms, at about 4.8±0.5 degrees angstroms, at about 4.2±0.5 degrees angstroms, at about 4.1±0.5 degrees angstroms, at about 4.1±0.5 degrees angstroms, at about 3.8±0.5 degrees angstroms, at about 3.6±0.5 degrees angstroms, at about 3.6±0.5 degrees angstroms, at about 3.5±0.5 degrees angstroms, at about 3.4±0.5 degrees angstroms, at about 3.4±0.5 degrees angstroms, at about 3.2±0.5 degrees angstroms, at about 3.2±0.5 degrees angstroms, at about 3.1±0.5 degrees angstroms, at about 3.0±0.5 degrees angstroms, at about 2.8±0.5 degrees angstroms, and at about 2.7±0.5 degrees angstroms.

9. A pharmaceutical composition comprising a co-crystalline form of claim 1.

10. The pharmaceutical composition of claim 9, further comprising a pharmaceutically acceptable excipient.

11. The pharmaceutical composition of claim 9, further comprising an additional drug for treating or preventing an alcohol related disorder.

12. The co-crystalline form of claim 1, wherein the coformer is urea.

13. The co-crystalline form of claim 12, wherein the molar ratio of the compound to the urea is about 1:1.

14. The co-crystalline form of claim 1, wherein the coformer is trimesic acid.

15. The co-crystalline form of claim 14, wherein the molar ratio of the compound to the trimesic acid is about 1:1.

16. A process for preparing a co-crystalline form of a compound having a formula of

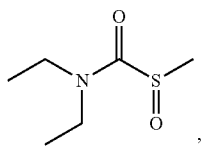

Formula I

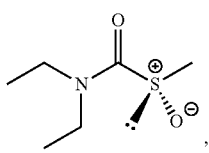

Formula I-a

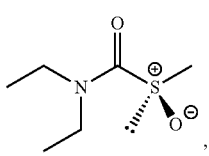

Formula I-b

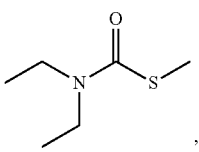

Formula II

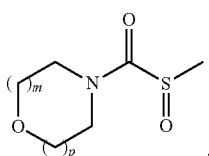

Formula III

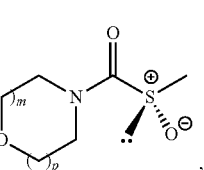

Formula III-a

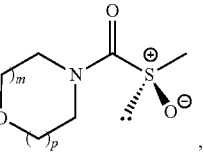

Formula III-b

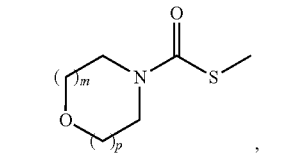

Formula VI

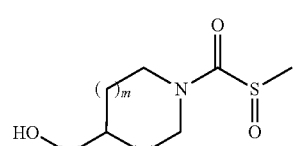

Formula IV

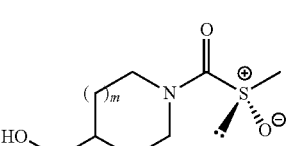

Formula IV-a

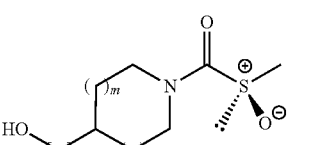

Formula IV-b

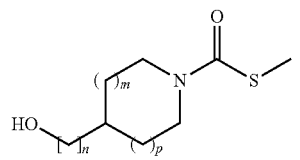

, or

Formula V wherein n is 0-6, m is 0-6, and p is 0-6;

and a coformer, wherein the coformer is urea, 3,5-dihydroxybenzoic acid, trimesic acid, ellagic acid, $MgCl_2$, or $CaCl_2$), or any combination thereof, wherein the process comprises co-crystallizing the compound and the coformer to form the co-crystalline form of the compound and the coformer.

17. The process of claim 16, wherein the process comprises dry grinding the compound and the coformer to form the co-crystalline form therefrom.

18. The process of claim 16, wherein the process comprises slurrying the compound and the coformer in an organic solvent to form the co-crystalline form therefrom.

19. The process of claim 18, wherein the organic solvent is selected from the group consisting of acetonitrile, ethyl acetate, cyclohexane, toluene, methanol, and any combination thereof.

20. The process of claim 19, wherein the organic solvent is ethyl acetate.

21. The process of claim 16, wherein the process comprises isolating the co-crystalline form of the compound and the coformer.

* * * * *